US012580051B2

(12) United States Patent
Melton et al.

(10) Patent No.: US 12,580,051 B2
(45) Date of Patent: Mar. 17, 2026

(54) IDENTIFYING METHYLATION PATTERNS THAT DISCRIMINATE OR INDICATE A CANCER CONDITION

(71) Applicant: GRAIL, Inc., Menlo Park, CA (US)

(72) Inventors: Collin Melton, Menlo Park, CA (US); Earl Hubbell, Palo Alto, CA (US); Oliver Claude Venn, San Francisco, CA (US)

(73) Assignee: GRAIL, Inc., Menlo Park, CA (US)

( * ) Notice: Subject to any disclaimer, the term of this patent is extended or adjusted under 35 U.S.C. 154(b) by 1245 days.

(21) Appl. No.: 17/187,319

(22) Filed: Feb. 26, 2021

(65) Prior Publication Data

US 2021/0292845 A1      Sep. 23, 2021

Related U.S. Application Data

(60) Provisional application No. 62/983,443, filed on Feb. 28, 2020.

(51) Int. Cl.

| | |
|---|---|
| *G16B 40/20* | (2019.01) |
| *C12Q 1/6886* | (2018.01) |
| *G06F 18/2415* | (2023.01) |
| *G16B 20/00* | (2019.01) |
| *G16B 45/00* | (2019.01) |

(52) U.S. Cl.
CPC .......... *G16B 40/20* (2019.02); *C12Q 1/6886* (2013.01); *G06F 18/24155* (2023.01); *G16B 20/00* (2019.02); *G16B 45/00* (2019.02); *C12Q 2600/154* (2013.01)

(58) Field of Classification Search
CPC ......... G16B 20/00; G16B 30/00; G16B 45/00
See application file for complete search history.

(56) References Cited

U.S. PATENT DOCUMENTS

| | | | | |
|---|---|---|---|---|
| 7,601,499 | B2 | 10/2009 | Berka et al. | |
| 11,168,356 | B2 * | 11/2021 | Lo ........................ | C12Q 1/6886 |
| 11,410,750 | B2 * | 8/2022 | Gross ................... | C12Q 1/6869 |
| 11,482,303 | B2 * | 10/2022 | Nicula ................... | G16B 25/10 |
| 11,581,062 | B2 * | 2/2023 | Maher .................... | G16B 20/20 |
| 11,685,958 | B2 * | 6/2023 | Gross ................... | C12Q 1/6869 |
| | | | | 435/6.11 |
| 11,725,251 | B2 * | 8/2023 | Gross ................... | C12Q 1/6827 |
| | | | | 702/19 |
| 11,773,450 | B2 * | 10/2023 | Yip ...................... | C12Q 1/6886 |
| | | | | 702/19 |
| 11,783,915 | B2 * | 10/2023 | Nicula ................... | G16H 50/20 |
| | | | | 706/20 |
| 11,795,513 | B2 * | 10/2023 | Gross ................... | C12Q 1/6869 |
| 12,024,750 | B2 * | 7/2024 | Gross ...................... | C40B 40/06 |
| 2016/0017419 | A1 | 1/2016 | Chiu et al. | |
| 2017/0212428 | A1 | 7/2017 | Roos et al. | |
| 2018/0237863 | A1 | 8/2018 | Namsaraev et al. | |
| 2019/0177792 | A1 | 6/2019 | Liu et al. | |

| | | | |
|---|---|---|---|
| 2019/0287649 | A1 | 9/2019 | Filippova et al. |
| 2019/0287652 | A1 | 9/2019 | Gross et al. |
| 2020/0005899 | A1 | 1/2020 | Nicula et al. |
| 2020/0340064 | A1 | 10/2020 | Gross et al. |
| 2020/0365229 | A1 | 11/2020 | Fields et al. |
| 2020/0385813 | A1 | 12/2020 | Venn |
| 2021/0065842 | A1 | 3/2021 | Valouev et al. |
| 2021/0285042 | A1 | 9/2021 | Singh et al. |
| 2021/0292845 | A1 | 9/2021 | Melton et al. |
| 2021/0313006 | A1 | 10/2021 | Gross et al. |
| 2021/0327534 | A1 | 10/2021 | Nicula et al. |
| 2021/0358626 | A1 | 11/2021 | Nicula et al. |

FOREIGN PATENT DOCUMENTS

| | | |
|---|---|---|
| WO | WO 2014/043763 | 3/2014 |
| WO | WO 2017/212428 | 12/2017 |
| WO | WO 2018/081130 A1 | 5/2018 |
| WO | WO 2019/195268 A2 | 10/2019 |
| WO | WO 2019/204360 A1 | 10/2019 |
| WO | WO 2019/209954 | 10/2019 |
| WO | WO 2020/069350 A1 | 2/2020 |
| WO | WO 2020/132148 A1 | 6/2020 |
| WO | WO 2020/154682 A3 | 7/2020 |
| WO | WO 2020/237184 | 11/2020 |

OTHER PUBLICATIONS

Doerge et al. (2002) Mapping and analysis of quantitative trait loci in experimental populations. Nature reviews genetics, vol. 3, p. 43-53. (Year: 2002).*
Bian, 2018, "Comparing the performance of selected variant callers using synthetic data and genome segmentation," BMC Bioinformatics 19:429.
Chaudhary et al., 2017, Journal of Clinical Oncology, 35(15), suppl.e14529.
Grunau et al., 2001, "MethDB—a public database for DNA methylation data," Nucleic Acids Research 29(1), 270-274.

(Continued)

*Primary Examiner* — Mary K Zeman
(74) *Attorney, Agent, or Firm* — Bookoff McAndrews, PLLC

(57) ABSTRACT

Systems and methods of identifying methylation patterns discriminating or indicating a cancer condition are provided. First and second datasets are obtained. Each dataset comprises a plurality of fragment methylation patterns determined by methylation sequencing of nucleic acids obtained from a first or second set of subjects and comprising a methylation state of each CpG site in a corresponding plurality of CpG sites. Each plurality of subjects has a respective first or second state of the cancer condition. First and second interval maps are generated for each respective dataset, each comprising a plurality of nodes characterized by a start methylation site, an end methylation site, a representation of each different fragment methylation pattern and a count of fragments. The first and second interval maps are scanned for qualifying methylation patterns within a predetermined range of CpG sites, satisfying one or more selection criteria, thereby identifying methylation patterns discriminating a cancer condition.

15 Claims, 26 Drawing Sheets

(56) References Cited

OTHER PUBLICATIONS

Huang et al., 2021, "MethHC 2.0: information repository of DNA methylation and gene expression in human cancer," Nucleic Acids Research 49(D1), D1268-D1275.

Hachiya et al., 2017, "Genome-wide identification of inter-individually variable DNA methylation sites improves the efficacy of epigenetic association studies," NPJ Genom Med. 2017. 2:11.

Karczewski et al., 2019, "Variation across 141,456 human exomes and genomes reveals the spectrum of loss-of-function intolerance across human protein-coding genes," bioRxiv doi.org/10.1101/531210.

Ongenaert et al., "PubMeth: a cancer methylation database combining text-mining and expert annotation," Nucleic Acids Research: doi:10.1093/nar/gkm788.

Sherry et al., 2001, "dbSNP: the NCBI database of genetic variation" Nuc. Acids. Res. 29, 308-311.

U.S. Appl. No. 62/847,223, filed May 13, 2019, Fields et al.

U.S. Appl. No. 62/985,258, filed Mar. 4, 2020, Nicula et al.

U.S. Appl. No. 62/877,755, filed Jul. 23, 2019, Valouev et al.

U.S. Appl. No. 63/003,087, filed Mar. 31, 2020, Gross et al.

U.S. Appl. No. 16/839,469, filed Apr. 3, 2020, Yip et al.

International Search Report and Written Opinion dated May 31, 2021 for PCT Application No. PCT/US2020/066217. 23 pages.

Invitation to Pay Additional Fees and Partial International Search Report dated Apr. 8, 2021 for PCT Application No. PCT/US2020/066217. 16 pages.

Agresti. An Introduction to Categorical Data Analysis. John Wiley & Son, New York. 1996; Chapter 5, pp. 103-144.

Boser, et al. A training algorithm for optimal margin classifiers. Proceedings of the 5th Annual ACM Workshop on Computational Learning Theory, ACM Press, Pittsburgh, PA. 1992; 142-152.

Breiman. Random Forests—Random Features. Technical Report 567, Statistics Department, U.C. Berkeley. 1999. 29 pages.

Casadio, et al. Urine cell-free DNA integrity as a marker for early bladder cancer diagnosis: preliminary data. Urol Oncol. 2013; 31(8):1744-1750.

Cavalcante and Santor. annotatr: genomicBreiman regions in context. Bioinformatics. 2017; 33(15):2381-2383.

Chan, et al. Cell-free nucleic acids in plasma, serum and urine: a new tool in molecular diagnosis. Ann Clin Biochem. 2003; 40(Pt 2):122-130.

Cristianini and Shawe-Taylor. An Introduction to Support Vector Machines. Chapter 6, Cambridge University Press, Cambridge. 2000; pp. 93-124.

De Mattos-Arruda, et al. Cell-free circulating tumour DNA as a liquid biopsy in breast cancer. Mol Oncol. 2016; 10(3):464-474.

Duda. Pattern Classification. Second Edition, John Wiley & Sons, Inc. 2001; pp. 259, 262-265.

Duda, et al. Pattern Classification and Scene Analysis. John Wiley & Sons, Inc., New York. 1973.

Everitt. Cluster analysis (3d ed.). Wiley, New York, N.Y. 1993.

Fernandes, et al. Transfer Learning with Partial Observability Applied to Cervical Cancer Screening. Pattern Recognition and Image Analysis: 8th Iberian Conference Proceedings. 2017. pp. 243-250.

Frenel, et al. Serial next-generation sequencing of circulating cell-free DNA evaluating tumor clone response to molecularly targeted drug administration. Clin Cancer Res. 2015; 21(20): 4586-4596.

Furey, et al. Support vector machine classification and validation of cancer tissue samples using microarray expression data. Bioinformatics. 2000; 16:906-914.

Goessl, et al. Fluorescent methylation-specific polymerase chain reaction for DNA based detection of prostate cancer in bodily fluids. Cancer Res. 2000; 60(21):5941-5845.

Hao, et al. Circulating cell-free DNA in serum as a biomarker for diagnosis and prognostic prediction of colorectal cancer. Br J Cancer. 2014; 111(8):1482-1489.

Hassoun. Adaptive Multilayer Neural Networks I. Fundamentals of Artificial Neural Networks, Chapter 5, Massachusetts Institute of Technology. 1995. 87 pages.

Hastie, et al. Additive Models, Trees, and Related Models. The Elements of Statistical Learning, Second Edition, Springer Science+ Business Media, LLC. 2009; 295-336.

Heitzer, et al. Circulating tumor DNA as a liquid biopsy for cancer. Clin Chem. 2015; 61(1):112-123.

Heitzer, et al. Establishment of tumorspecific copy No. alterations from plasma DNA of patients with cancer. Int J Cancer. 2013; 133(2):346-356.

Jensen, et al. High-Throughput Massively Parallel Sequencing for Fetal Aneuploidy Detection from Maternal Plasma. PLoS One. 2013. 8; e57381.

Kaufman, et al. Finding Groups in Data: An Introduction to Cluster Analysis. Wiley, New York, N.Y. 1990.

Kim, et al. Circulating cell-free DNA as a promising biomarker in patients with gastric cancer: diagnostic validity and significant reduction of cfDNA after surgical resection. Ann Surg Treat Res. 2014; 86(3):136-142.

Langmead, et al. Fast gapped-read alignment with Bowtie 2. Nat Methods. 2012; 9:357-359.

Larochelle, et al. Exploring strategies for training deep neural networks. J Mach Learn Res. 2009; 10:1-40.

Li, et al. Fast and accurate short read alignment with Burrows-Wheeler transform. Bioinformatics. 2009; 25(14):1754-1760.

Li, et al. Mappability and read length. Frontiers In Genetics. 2014; 5(381):1-7.

Lo, et al. Maternal Plasma DNA Sequencing Reveals the Genome-Wide Genetic and Mutational Profile of the Fetus. Science Translational Medicine, 2010; vol. 2, Issue 61, 14 pages, [online], retrieved from the internet URL: www.stm.sciencemag.org.

Raptis, et al. Quantitation and characterization of plasma DNA ins normals and patients with systemic lupus erythematosu. J Clin Invest. 1980; 66(6): 1391-1399.

Salvi, et al. Cell-free DNA as a diagnostic marker for cancer: current insights. Onco Targets Ther. 2016; 9: 6549-6559.

Shao, et al. Quantitative analysis of cell-free DNA in ovarian cancer. Oncol Lett. 2015; 10(6):3478-3482.

Shapiro, et al. Determination of circulating DNA levels in patients with benign or malignant gastrointestinal disease. Cancer. 1983; 51(11): 2116-2120.

Smith, et al. Evaluating alignment and variant-calling software for mutation identification in C. elegans by whole-genome sequencing. PLOS ONE. 2017, doi.org/10.1371/journal.pone.0174446.

Song. Comparison of co-expression measures: mutual information, correlation, and model based indices. BMC bioinformatics. 2012; 13.1; 1-21.

Sozzi. Quantification of free circulating DNA as a diagnostic marker in lung cancer. J Clin Oncol. 2003; 21(21): 3902-3908.

Stroun, et al. Neoplastic characteristics of the DNA found in the plasma of cancer patients. Oncology. 1989; 46(5): 318-322.

Swanton, et al. Phylogenetic ctDNA analysis depicts early stage lung cancer evolution. Nature 2017; 545(7655):446-451.

Vapnik. Perceptrons and Their Generalizations. Statistical Learning Theory, Chapter 9, Wiley, New York. 1998; 375-400.

Vincent, et al. Stacked denoising autoencoders: Learning useful representations in a deep network with a local denoising criterion. J Mach Learn Res. 2010; 11:3371-3408.

Yang, et al. DistAI: An Inter-pattern Distance-based Constructive Learning Algorithm. Intelligent Data Analysis. 1999; 3(1):55-73.

Yoon. Hidden Markov Models and their Applications in Biological Sequence Analysis. Curr. Genomics. 2009; 10(6):402-415.

Zonta, et al. Assessment of DNA integrity, applications for cancer research. Adv Clin Chem. 2015; 70:197-246.

Chan, et al. Noninvasive detection of cancer-associated genome-wide hypomethylation and copy number aberrations by plasma DNA bisulfite sequencing. PNAS. Nov. 19, 2013; vol. 110, No. 47, 18761-18768.

Fan, et al. Methods for genome-wide DNA methylation analysis in human cancer. Briefings in Functional Genomics. 2016; 15(6): 432-442.

(56) References Cited

OTHER PUBLICATIONS

Lapin, et al. Fragment size and level of cell-free DNA provide prognostic information in patientes with advanced pancreatic cancer. J Translational Medicine. 2018; 16(300).

Lee, et al. Analyzing the cancer methylome through targeted bisulfite sequencing. Cancer Letters. 2013; vol. 340: 171-178.

Liu, et al. Bisulfite-free direct detection of 5- methylcytosine and 5-hydroxymethylcytosine at base resolution. Nature Biotechnology. 2019; 37:424-429.

International Search Report and Written Opinion dated Jun. 18, 2021 for PCT Application No. PCT/US2021/020012. 16 pages.

Anonymous. Intervalmap.pkg.go.dec. Published Nov. 11, 2019. Retrieved from https://pkg.go.dev/github.com/grailbio/base@v0.0.6/intervalmap. 6 pages.

Du et al., 2010, BMC Bioinformatics 11:587.

Gross, S. et al., U.S. Appl. No. 62/642,480, filed Mar. 13, 2018.

Gross, S. et al., U.S. Appl. No. 62/972,375, filed Feb. 10, 2020.

Jones, 2002, Oncogene 21:5358-5360.

Kang, Shuli et al., "CancerLocator: non-invasive cancer diagnosis and tissue-of-origin prediction using methylation profiles of cell-free DNA", Genome Biology, vol. 18, No. 1.

Klein et al., 2018, "Development of a comprehensive cell-free DNA (cfDNA) assay for early detection of multiple tumor types: The Circulating Cell-free Genome Atlas (CCGA) study," J. Clin. Oncology 36(15), 12021-12021.

Lee et al., 2013, "MatchTree: Flexible, scalable, and fault-tolerant wide-area resource discovery with distributed matchmaking and aggregation," Fut Gen Comp Sys 29, 1596-1610.

Liu et al., 2019, "Genome-wide cell-free DNA (cfDNA) methylation signatures and effect on tissue of origin (TOO) performance," J. Clin. Oncology 37(15), 3049-3049.

Masser et al., 2015, "Targeted DNA Methylation Analysis by Next-generation Sequencing," J. Vis. Exp. (96).

Newman, J., et al., U.S. Appl. No. 62/834,904, filed Apr. 16, 2019.

Nicula, V., et al., U.S. Appl. No. 62/948,129, filed Dec. 13, 2019.

Paska, et al., 2015, Biochemia Medica 25(2):161-176.

Wang et al., 2015, "Syntax-based Deep Matching of Short Texts," arXiv: 1503.02427v6[cs.CL].

Warton, et al., 2015, Front Mol Biosci, 2(13).

Wald, 2007, "On Fast Construction of SAH-based Bounding vol. Hierarchies," IEEE, doi:10.1109/RT.2007.4342588.

Venn, Oliver Claud, U.S. Appl. No. 62/781,549, filed Dec. 18, 2018.

Ziller et al., 2015, "Coverage recommendations for methylation analysis by whole-genome bisulfite sequencing," Nature Methods. 12(3):230-232.

* cited by examiner

Figure 2A:
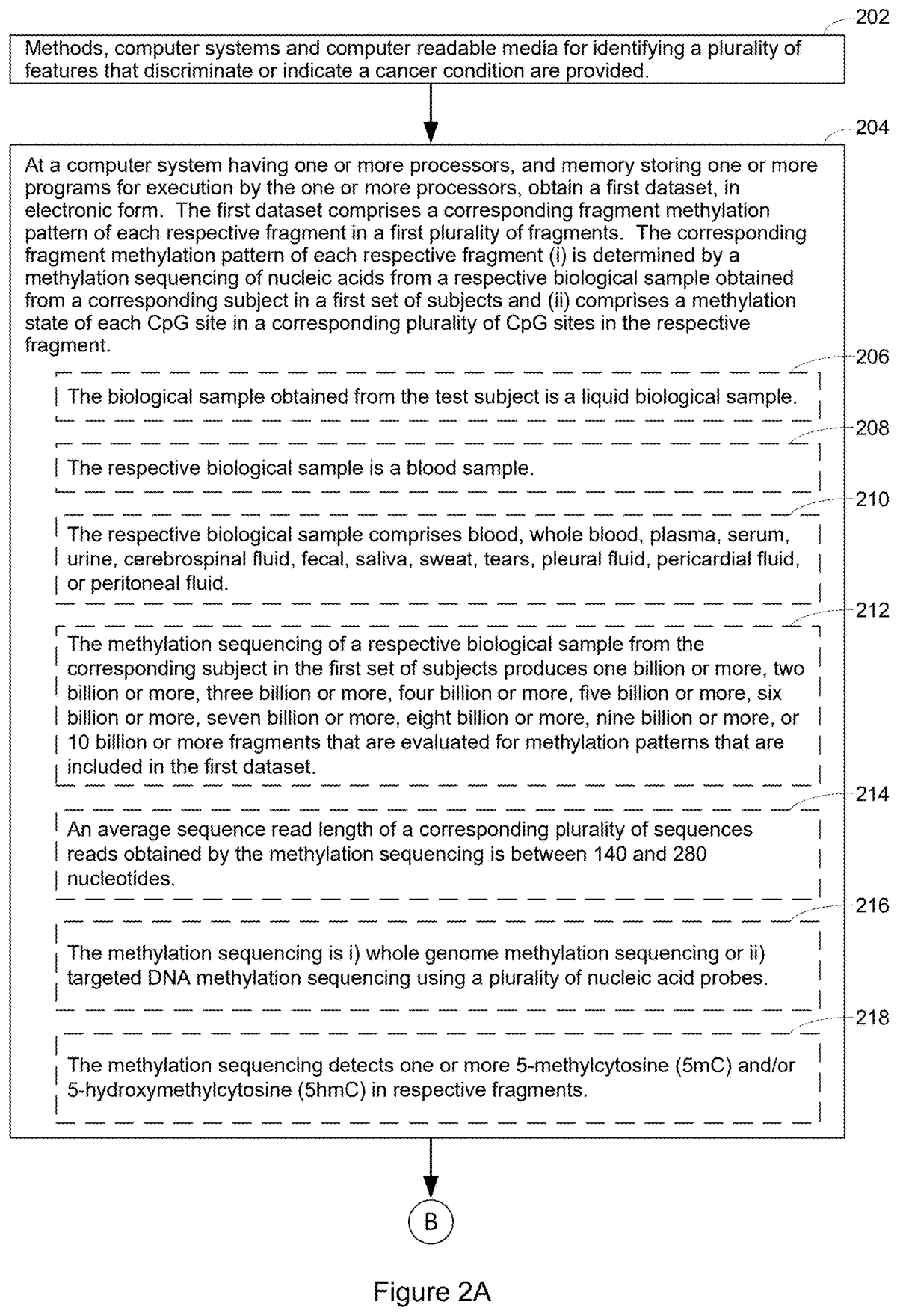

202

Methods, computer systems and computer readable media for identifying a plurality of features that discriminate or indicate a cancer condition are provided.

204

At a computer system having one or more processors, and memory storing one or more programs for execution by the one or more processors, obtain a first dataset, in electronic form. The first dataset comprises a corresponding fragment methylation pattern of each respective fragment in a first plurality of fragments. The corresponding fragment methylation pattern of each respective fragment (i) is determined by a methylation sequencing of nucleic acids from a respective biological sample obtained from a corresponding subject in a first set of subjects and (ii) comprises a methylation state of each CpG site in a corresponding plurality of CpG sites in the respective fragment.

206

The biological sample obtained from the test subject is a liquid biological sample.

208

The respective biological sample is a blood sample.

210

The respective biological sample comprises blood, whole blood, plasma, serum, urine, cerebrospinal fluid, fecal, saliva, sweat, tears, pleural fluid, pericardial fluid, or peritoneal fluid.

212

The methylation sequencing of a respective biological sample from the corresponding subject in the first set of subjects produces one billion or more, two billion or more, three billion or more, four billion or more, five billion or more, six billion or more, seven billion or more, eight billion or more, nine billion or more, or 10 billion or more fragments that are evaluated for methylation patterns that are included in the first dataset.

214

An average sequence read length of a corresponding plurality of sequences reads obtained by the methylation sequencing is between 140 and 280 nucleotides.

216

The methylation sequencing is i) whole genome methylation sequencing or ii) targeted DNA methylation sequencing using a plurality of nucleic acid probes.

218

The methylation sequencing detects one or more 5-methylcytosine (5mC) and/or 5-hydroxymethylcytosine (5hmC) in respective fragments.

232

Generate one or more first state interval maps for one or more corresponding genomic regions using the first dataset. Each first state interval map in the one or more first state interval maps comprises a corresponding independent plurality of nodes. Each respective node in each corresponding independent plurality of nodes in the one or more first state interval maps is characterized by a corresponding start methylation site, a corresponding end methylation site, and for each different fragment methylation pattern observed across the first plurality of fragments in the first dataset between the corresponding start methylation site and the corresponding end methylation site of the respective node, a representation of the different fragment methylation pattern and a count of fragments in the first dataset whose fragment methylation pattern begins at the corresponding start methylation site and ends at the corresponding end methylation site and has the different fragment methylation pattern.

234

There are more than 10,000 CpG sites, more than 25,000 CpG sites, more than 50,000 CpG sites, or more than 80,000 CpG sites across the one or more corresponding genomic regions.

236

Each genomic region in the one or more corresponding genomic regions represents between 500 base pairs and 10,000 base pairs of a human genome reference sequence.

238

Each genomic region in the one or more corresponding genomic regions represents between 500 base pairs and 2,000 base pairs of a human genome reference sequence.

240

Each genomic region in the one or more corresponding genomic regions represents a different portion of a human genome reference sequence.

Figure 2C

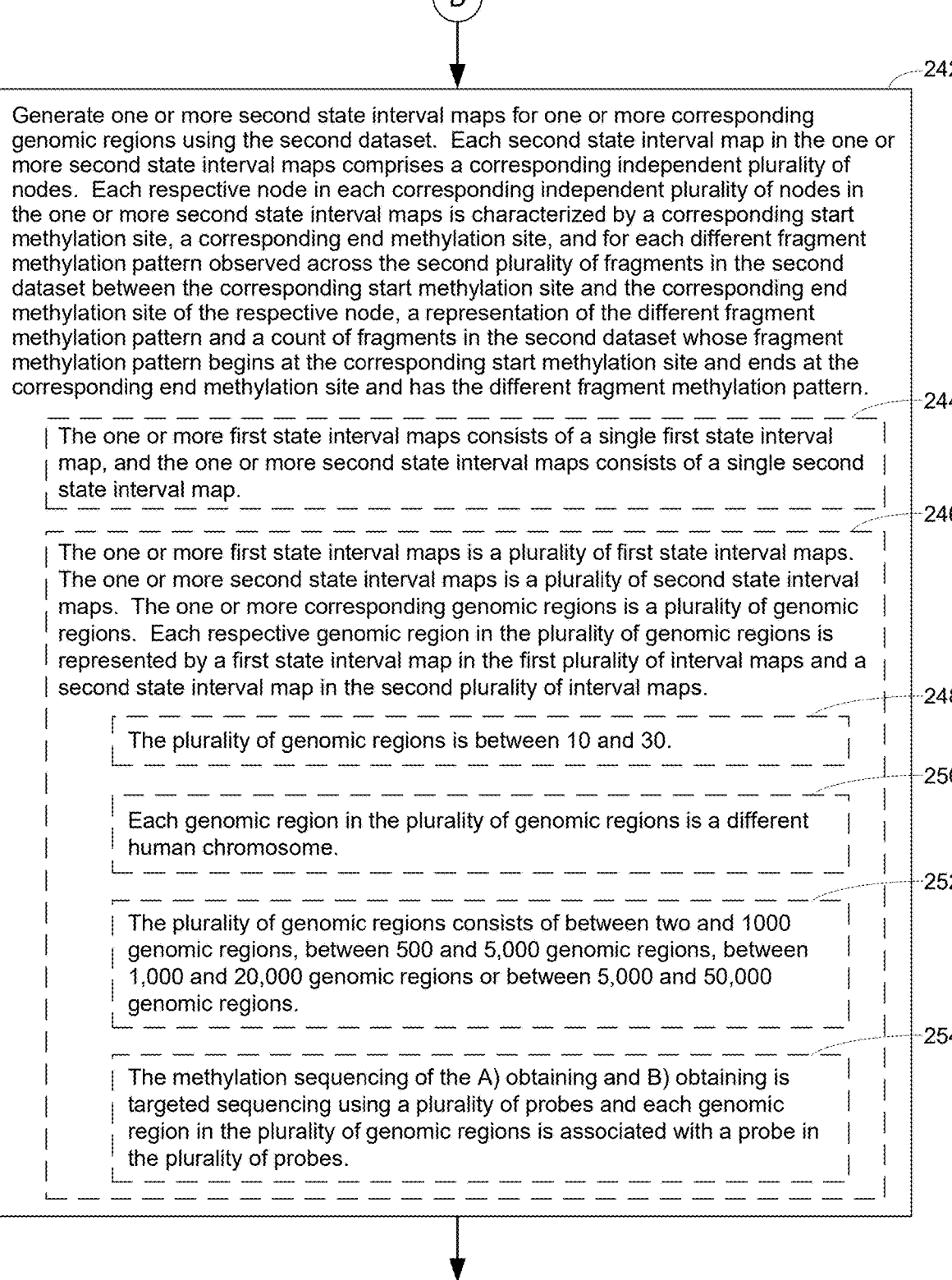

D

242

Generate one or more second state interval maps for one or more corresponding genomic regions using the second dataset. Each second state interval map in the one or more second state interval maps comprises a corresponding independent plurality of nodes. Each respective node in each corresponding independent plurality of nodes in the one or more second state interval maps is characterized by a corresponding start methylation site, a corresponding end methylation site, and for each different fragment methylation pattern observed across the second plurality of fragments in the second dataset between the corresponding start methylation site and the corresponding end methylation site of the respective node, a representation of the different fragment methylation pattern and a count of fragments in the second dataset whose fragment methylation pattern begins at the corresponding start methylation site and ends at the corresponding end methylation site and has the different fragment methylation pattern.

244

The one or more first state interval maps consists of a single first state interval map, and the one or more second state interval maps consists of a single second state interval map.

246

The one or more first state interval maps is a plurality of first state interval maps. The one or more second state interval maps is a plurality of second state interval maps. The one or more corresponding genomic regions is a plurality of genomic regions. Each respective genomic region in the plurality of genomic regions is represented by a first state interval map in the first plurality of interval maps and a second state interval map in the second plurality of interval maps.

248

The plurality of genomic regions is between 10 and 30.

250

Each genomic region in the plurality of genomic regions is a different human chromosome.

252

The plurality of genomic regions consists of between two and 1000 genomic regions, between 500 and 5,000 genomic regions, between 1,000 and 20,000 genomic regions or between 5,000 and 50,000 genomic regions.

254

The methylation sequencing of the A) obtaining and B) obtaining is targeted sequencing using a plurality of probes and each genomic region in the plurality of genomic regions is associated with a probe in the plurality of probes.

256

Identify a plurality of qualifying methylation patterns that discriminates or indicates a cancer condition by scanning the one or more first interval maps and the one or more second interval maps for a plurality of qualifying methylation patterns. Each qualifying methylation pattern in the plurality of qualifying methylation patterns: (i) has a length that is in a predetermined CpG site number range, within the fragment methylation patterns of the one or more first interval maps and the one or more second interval maps, (ii) satisfies one or more selection criteria, and (iii) spans a corresponding CpG interval between a corresponding initial CpG site and a corresponding final CpG site.

258

The one or more selection criterion specifies that a methylation pattern (i) is represented in the one or more first interval maps with a first frequency that satisfies a first frequency threshold, (ii) is represented in the one or more first interval maps with a coverage that satisfies a first state depth threshold, and (iii) is represented in the one or more second interval maps with a second frequency that satisfies a second frequency threshold.

260

The methylation pattern is represented in the one or more first interval maps with a first frequency that satisfies a first frequency threshold when the frequency of the methylation pattern in the one or more first interval maps exceeds the first frequency threshold. The methylation pattern is represented in the one or more first interval maps with a coverage that satisfies the first state depth threshold when the coverage of the methylation pattern in the one or more first interval maps exceeds the first state depth threshold. The methylation pattern is represented in the one or more second interval maps with a second frequency that satisfies the second frequency threshold when the frequency of the methylation pattern in the one or more second interval maps is less than the second frequency threshold.

262

The first frequency threshold is 0.2, the first state depth threshold is 10, and the second frequency threshold is 0.001.

264

A respective methylation pattern satisfies the one or more selection criterion when the expression $-\log_{10}((\text{second count})/(\text{second state depth threshold}))$ for the methylation pattern exceeds 3, 4, 5 or 6. Second count = a count of the respective methylation pattern in the one or more second state interval maps. Second state depth threshold = a coverage in the region of genome represented by the respective methylation pattern in the one or more second state interval maps.

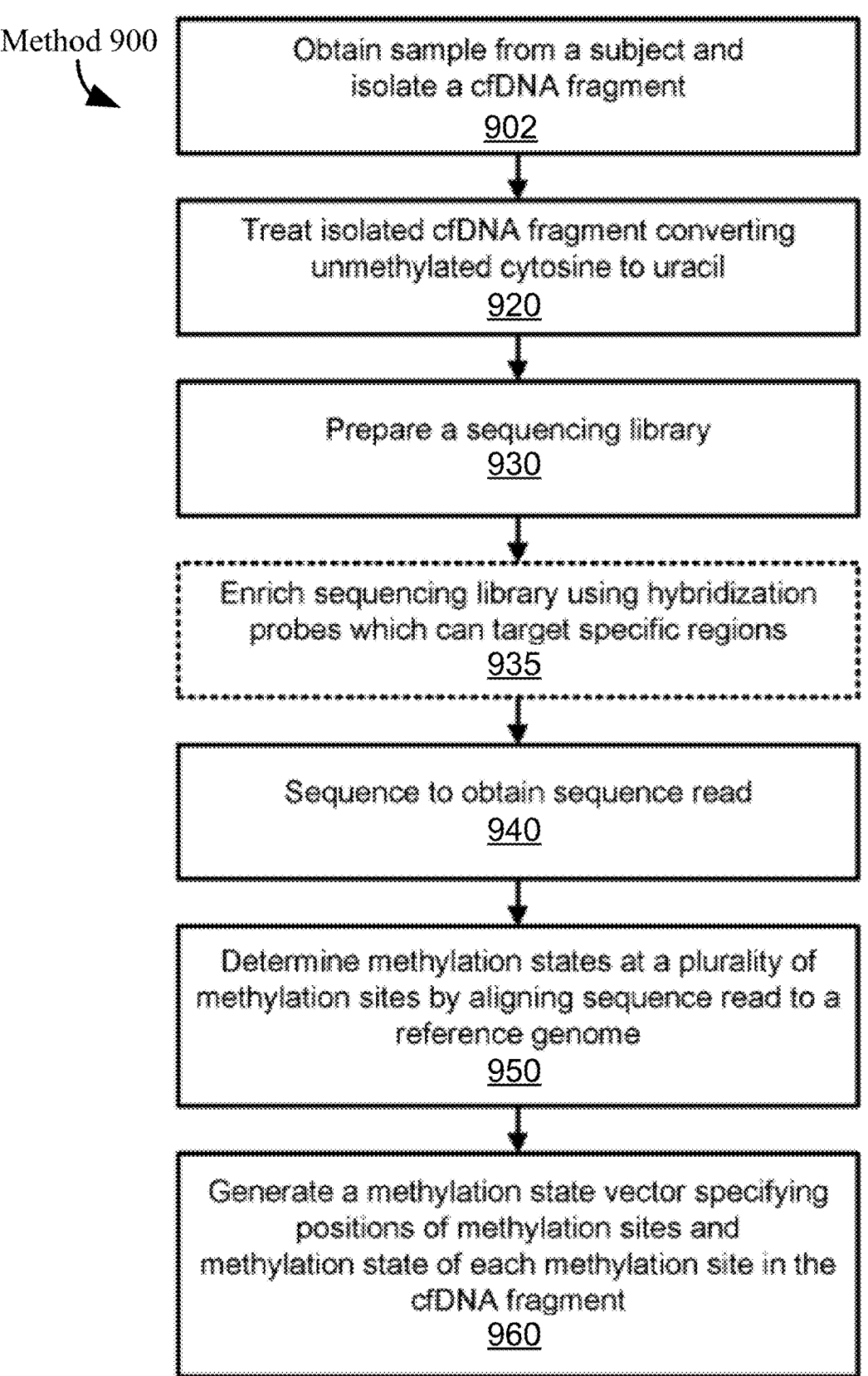

Method 900

Obtain sample from a subject and
isolate a cfDNA fragment
902

Treat isolated cfDNA fragment converting
unmethylated cytosine to uracil
920

Prepare a sequencing library
930

Enrich sequencing library using hybridization
probes which can target specific regions
935

Sequence to obtain sequence read
940

Determine methylation states at a plurality of
methylation sites by aligning sequence read to a
reference genome
950

Generate a methylation state vector specifying
positions of methylation sites and
methylation state of each methylation site in the
cfDNA fragment
960

Figure 9

| browser_range | states | tumor_alt | tumor_depth | normal_alt | normal_depth | sample_alt | sample_depth |
|---|---|---|---|---|---|---|---|
| chr19:58038923-58038968 | MMMM | 6 | 13 | 2 | 82581 | 99 | 240 |

| browser_range | states | tumor_alt | tumor_depth | normal_alt | normal_depth | sample_alt | sample_depth |
|---|---|---|---|---|---|---|---|
| chr15:94774205-94774289 | MMMM | 5 | 21 | 0 | 30448 | 23 | 106 |

Matched cfDNA

Biopsy

| browser_range | states | tumor_alt | tumor_depth | normal_alt | normal_depth | sample_alt | sample_depth |
|---|---|---|---|---|---|---|---|
| chr15:63674135-63674216 | MUMMM | 2 | 10 | 0 | 11716 | 4 | 85 |

Matched cfDNA

Biopsy

| browser_range | states | tumor_alt | tumor_depth | normal_alt | normal_depth | sample_alt | sample_depth |
|---|---|---|---|---|---|---|---|
| chr12:14134320-14134435 | MMMM | 5 | 11 | 2 | 53221 | 34 | 167 |

Matched cfDNA

Biopsy

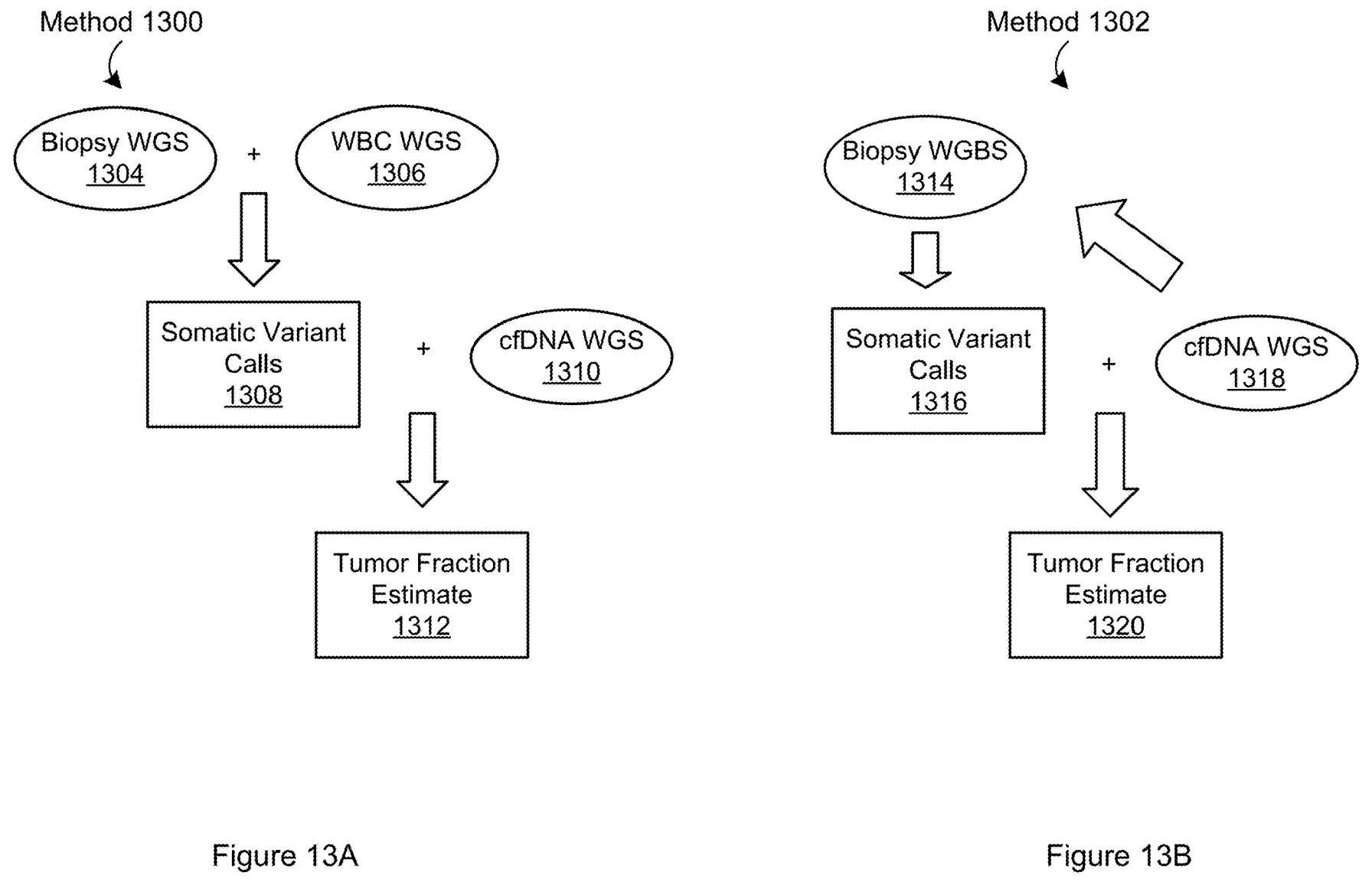

Method 1302 cfDNA WGS
1318

Biopsy WGBS
1314

Somatic Variant
Calls
1316

+

Tumor Fraction
Estimate
1320

Figure 13B

Method 1300

WBC WGS
1306

+

Biopsy WGS
1304

Somatic Variant
Calls
1308 cfDNA WGS
1310

+

Tumor Fraction
Estimate
1312

Figure 13A

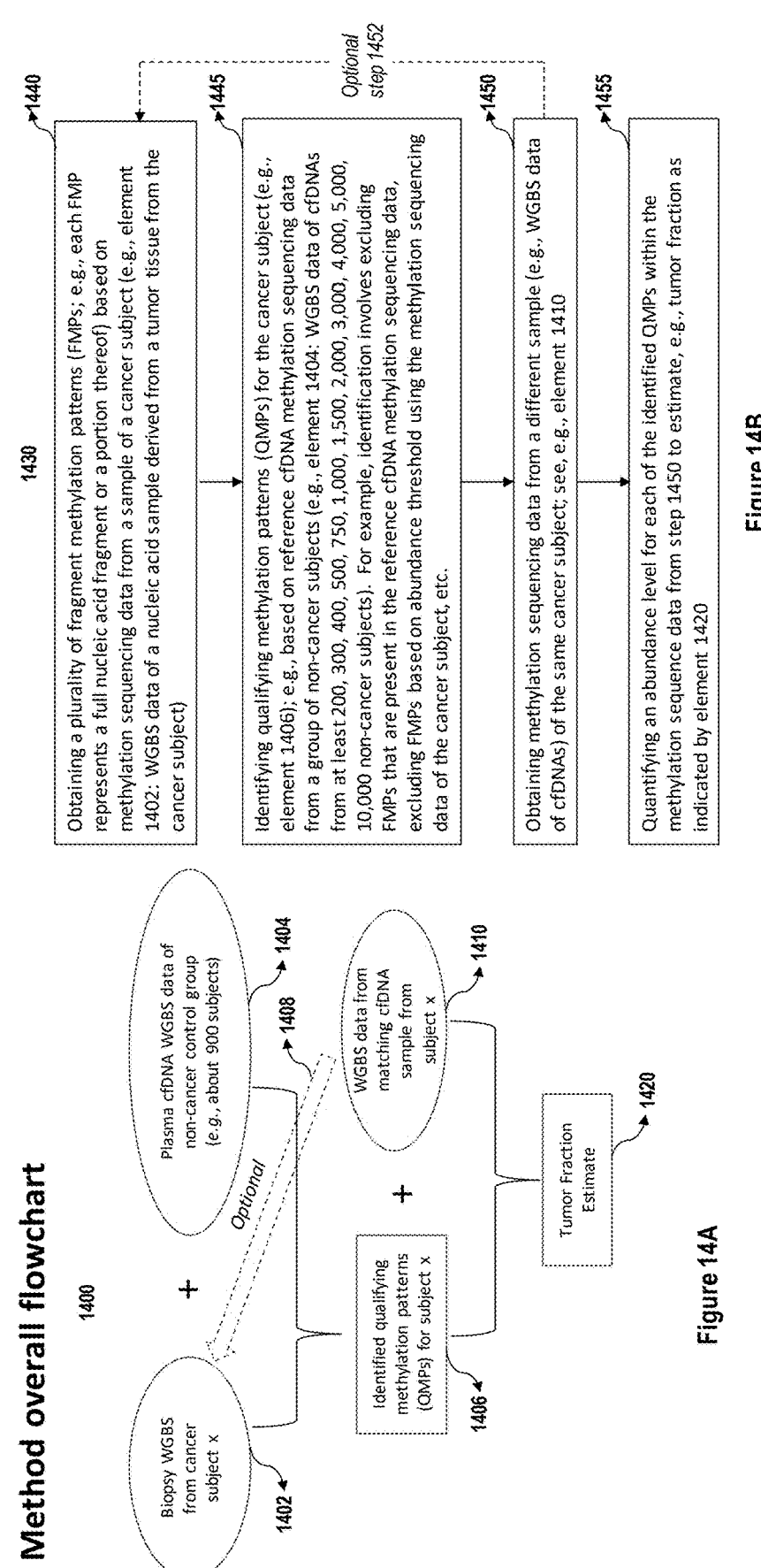

TF estimate based on qualifying methylation pattern using WGBS data

Method overall flowchart

1430

1440 — Obtaining a plurality of fragment methylation patterns (FMPs; e.g., each FMP represents a full nucleic acid fragment or a portion thereof) based on methylation sequencing data from a sample of a cancer subject (e.g., element 1402: WGBS data of a nucleic acid sample derived from a tumor tissue from the cancer subject)

1445 — Identifying qualifying methylation patterns (QMPs) for the cancer subject (e.g., element 1406); e.g., based on reference cfDNA methylation sequencing data from a group of non-cancer subjects (e.g., element 1404: WGBS data of cfDNAs from at least 200, 300, 400, 500, 750, 1,000, 1,500, 2,000, 3,000, 4,000, 5,000, 10,000 non-cancer subjects). For example, identification involves excluding FMPs that are present in the reference cfDNA methylation sequencing data, excluding FMPs based on abundance threshold using the methylation sequencing data of the cancer subject, etc.

*Optional step 1452*

1450 — Obtaining methylation sequencing data from a different sample (e.g., WGBS data of cfDNAs) of the same cancer subject; see, e.g., element 1410

1455 — Quantifying an abundance level for each of the identified QMPs within the methylation sequence data from step 1450 to estimate, e.g., tumor fraction as indicated by element 1420

Figure 14B

Biopsy WGBS from cancer subject x — 1402

+

Plasma cfDNA WGBS data of non-cancer control group (e.g., about 900 subjects) — 1404

1408

*Optional*

WGBS data from matching cfDNA sample from subject x — 1410

Identified qualifying methylation patterns (QMPs) for subject x — 1406

+

Tumor Fraction Estimate — 1420

TF estimate based on qualifying methylation pattern using TM data

Method overall flowchart

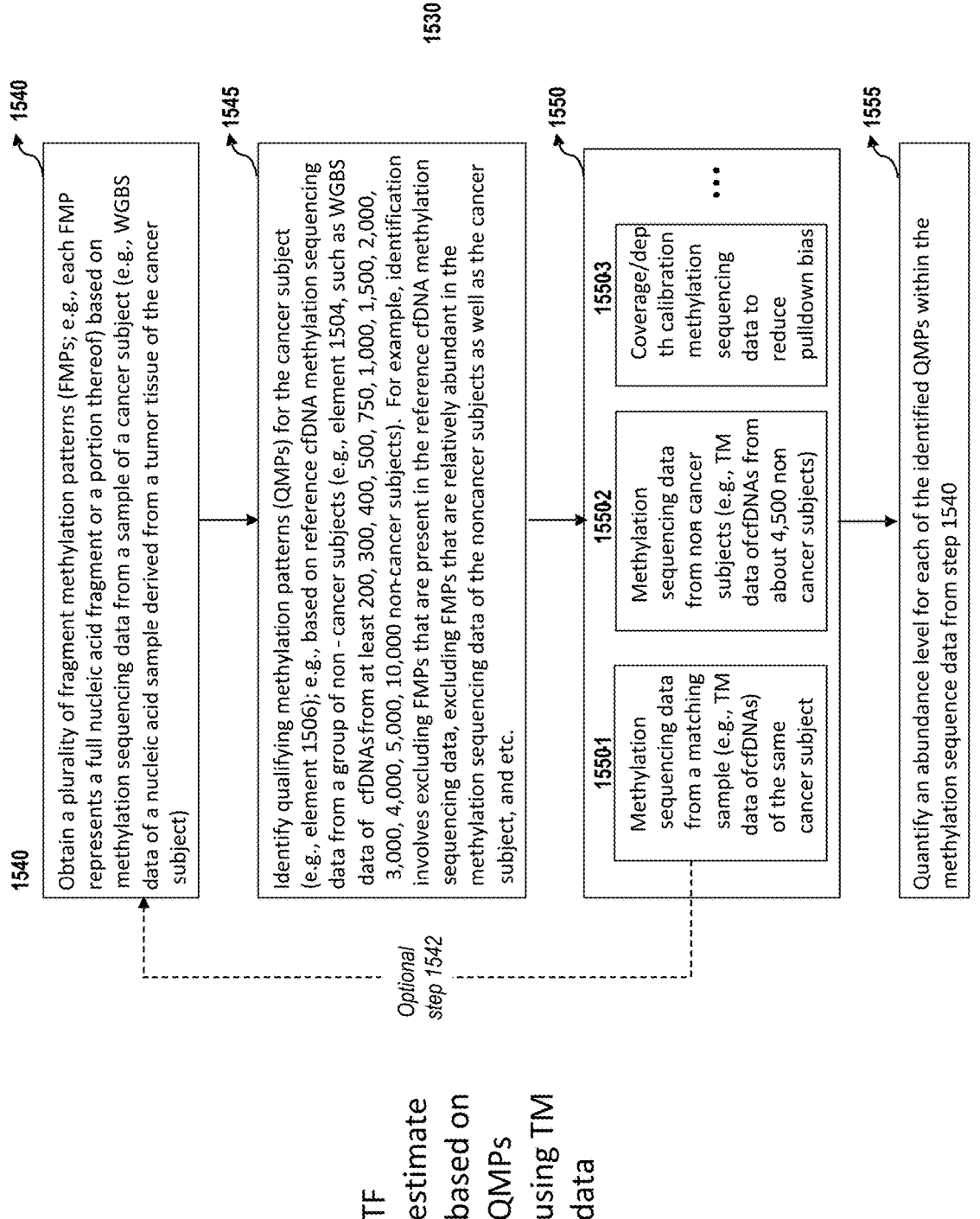

1530

1540

Obtain a plurality of fragment methylation patterns (FMPs; e.g., each FMP represents a full nucleic acid fragment or a portion thereof) based on methylation sequencing data from a sample of a cancer subject (e.g., WGBS data of a nucleic acid sample derived from a tumor tissue of the cancer subject)

1545

Identify qualifying methylation patterns (QMPs) for the cancer subject (e.g., element 1506); e.g., based on reference cfDNA methylation sequencing data from a group of non - cancer subjects (e.g., element 1504, such as WGBS data of cfDNAs from at least 200, 300, 400, 500, 750, 1,000, 1,500, 2,000, 3,000, 4,000, 5,000, 10,000 non-cancer subjects). For example, identification involves excluding FMPs that are present in the reference cfDNA methylation sequencing data, excluding FMPs that are relatively abundant in the methylation sequencing data of the noncancer subjects as well as the cancer subject, and etc.

1550

15501

Methylation sequencing data from a matching sample (e.g., TM data of cfDNAs) of the same cancer subject

15502

Methylation sequencing data from non cancer subjects (e.g., TM data of cfDNAs from about 4,500 non cancer subjects)

15503

Coverage/dep th calibration methylation sequencing data to reduce pulldown bias

...

1555

Quantify an abundance level for each of the identified QMPs within the methylation sequence data from step 1540

Optional step 1542

TF estimate based on QMPs using TM data

Figure 15B

IDENTIFYING METHYLATION PATTERNS THAT DISCRIMINATE OR INDICATE A CANCER CONDITION

CROSS REFERENCE TO RELATED APPLICATION

This application claims priority to U.S. Provisional Patent Application No. 62/983,443 entitled "Identifying Methylation Patterns that Discriminate or Indicate A Cancer Condition," filed Feb. 28, 2020, which is hereby incorporated by reference.

TECHNICAL FIELD

This specification relates generally to using methylation patterns in biological samples to identify methylation patterns that discriminate or indicate a cancer condition.

BACKGROUND

Earlier detection of cancer is one of the most humane ways to improve cancer outcomes. Status quo treatments—the combination of surgery, chemotherapy and radiation for solid tumors, or chemo and bone marrow transplants for liquid ones—have drawbacks including unsatisfactory survival rates. Treatments often leave patients in pain, while providing an unsatisfactory amount of survival time. New immunotherapies also have drawbacks. Patients have to be treated in intensive care units, and there are often deadly side effects. All such treatments are more effective when cancer is detected early.

In order to develop better cures and cancer diagnostics, resources have been invested in the hunt for single mutations in cancers. This practice has evolved into a popular medical effort known as "precision oncology" in which tumors are sequenced to identify the key druggable mutations responsible for the uncontrolled growth of cells. For instance, a clinical-trial initiative spearheaded by the National Cancer Institute called the Molecular Analysis for Therapy Choice, or MATCH, started in 2015. There are more than 30 arms of this trial. Among the more common tumors tested in this trial, "actionable" mutations addressable by existing drugs were found in 15% of cases at best. A bigger disappointment is that even pairing a mutation to a drug did not guarantee results—only a third of the matched patients responded to the treatment, and half of those responses faded within six months. Though the pursuit of precision oncology is ongoing, the results to date indicate that most cancers are far too complex to be addressed with such a reductionism approach.

In fact, most common cancers are far more confounding—up to 95% of cancer drugs in clinical trials fail to win Food and Drug Administration approval. And among the other 5%, many improve survival by only a few months and for a fraction of the treated cases.

The above drawbacks again highlight the need for early detection. However, current screening tests are unsatisfactory. Monitoring methods such as mammography, colonoscopy, Pap smears and testing for prostate specific antigen (PSA) have been in use for decades, but not all are uniformly successful. Some cancers progress so slowly that a patient is more likely to die of something else, while some dangerous tumors are not detectable until it is too late to cure them. Moreover, to date, no satisfactory screening test is available for numerous cancers, including lung cancer.

To develop such screening tests, then, there is a need to define "biomarkers" of cancerous cells. These can be almost anything—such as a strand of genetic material—that the cancer cells release. The National Cancer Institute is supporting large initiatives with the hope that such biomarkers will not only provide the earliest footprints of cancer but also help to separate aggressive tumors from non-life-threatening ones. Advances in biomolecule sequencing, in particular with respect to nucleic acid samples, have revolutionized the fields of cellular and molecular biology and provide a promising technology for discovering such biomarkers. Facilitated by the development of automated sequencing systems, it is now possible to sequence whole genomes.

One particular approach to finding biomarkers is to use such sequencing to identify aberrant DNA methylation patterns. DNA methylation plays an important role in regulating gene expression. Aberrant DNA methylation has been implicated in many disease processes, including cancer, and specific patterns of methylation have been determined to be associated with particular cancer conditions. See, e.g., Jones, 2002, Oncogene 21:5358-5360; Paska and Hudler, 2015, Biochemia Medica 25 (2): 161-176, and Du et al., 2010, BMC Bioinformatics 11:587, doi: 10.1186/1471-2105-11-587, each of which is hereby incorporated herein by reference in its entirety. Moreover, methylation patterns can be used to classify cancer conditions in subjects (e.g., type of cancer, stage of cancer, absence or presence of cancer). DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions and/or allele specific methylation patterns may be useful as molecular markers for non-invasive diagnostics using circulating cell-free DNA. See, e.g., Warton and Samimi, 2015, Front Mol Biosci, 2 (13) doi: 10.3389/fmolb.2015.00013.

While new sequencing technologies have made large scale sequencing, including methylation sequencing, possible, there have also been a commensurate increase in the number and complexity of the genomes that are being sequenced with these new sequencing technologies. Although large quantities of high-fidelity nucleic acid sequences can now be obtained, there remain many issues with leveraging these sequences to gain biological insight and inform disease detection and diagnosis.

Given the above background, there is a need in the art for improved approaches for identifying biomarkers using increasingly complex and large-scale nucleic acid sequencing data. Further, there is a need in the art for improved methods to use such biomarkers to model and infer complex biological patterns and non-linearities across the genome and thus develop tests for the detection, diagnosis, and/or monitoring of diseases, such as cancer.

SUMMARY

The present disclosure addresses the shortcomings identified in the background by providing robust techniques for identifying a plurality of qualifying methylation patterns that discriminate or indicate a cancer condition (e.g., a plurality of qualifying methylation patterns, of a length that is a predetermined number of CpG sites, or CpG number range, that satisfy one or more selection criterion) in biological samples obtained from a subject using nucleic acid samples. The combination of methylation data with whole-genome, or targeted genome, sequencing data, and the use of interval maps comprising nodes to represent methylation patterns corresponding to specific genomic regions provides additional diagnostic and analytical power beyond previous identification methods.

Technical solutions (e.g., computing systems, methods, and non-transitory computer-readable storage mediums) for addressing the above-identified problems with identifying methylation patterns that discriminate or indicate a cancer condition are provided in the present disclosure.

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

One aspect of the present disclosure provides a method of identifying a plurality of qualifying methylation patterns that discriminate or indicate a cancer condition, at a computer system having one or more processors, and memory storing one or more programs for execution by the one or more processors. The method comprises obtaining a first dataset, in electronic form, where the first dataset comprises a corresponding fragment methylation pattern of each respective fragment in a first plurality of fragments. The corresponding fragment methylation pattern of each respective fragment is determined by a methylation sequencing of nucleic acids from a respective biological sample obtained from a corresponding subject in a first set of one or more subjects and comprises a methylation state of each CpG site in a corresponding plurality of CpG sites in the respective fragment. In some embodiments the first plurality of fragments comprises more than 100 fragments, more than 500 fragment, more than 1000 fragments, more than 10,000 fragments, more than 100,000 fragments, more than 500,000 fragments, more than 1 million fragments, more than 10 million fragments, or more than 100 million fragments.

The method further comprises obtaining a second dataset, in electronic form, where the second dataset comprises a corresponding fragment methylation pattern of each respective fragment in a second plurality of fragments. The corresponding fragment methylation pattern of each respective fragment is determined by a methylation sequencing of nucleic acids from a respective biological sample obtained from a corresponding subject in a second set of subjects and comprises a methylation state of each CpG site in a corresponding plurality of CpG sites in the respective fragment. Each subject in the first set of one or more subjects has a first state of the cancer condition and each subject in the second set of subjects has a second state of the cancer condition. In some embodiments the second plurality of fragments comprises more than 100 fragments, more than 500 fragment, more than 1000 fragments, more than 10,000 fragments, more than 100,000 fragments, more than 500,000 fragments, more than 1 million fragments, more than 10 million fragments, or more than 100 million fragments.

The method further comprises generating one or more first state interval maps for one or more corresponding genomic regions using the first dataset. Each first state interval map in the one or more first state interval maps comprises a corresponding independent plurality of nodes. In some embodiments the corresponding independent plurality of nodes comprises more than 50 nodes, more than 100 nodes, more than 500 node, more than 1000 nodes, more than 10,000 nodes, more than 100,000 nodes, more than 1 million nodes or more than 1 million nodes. Each respective node in each corresponding independent plurality of nodes in the one or more first state interval maps is characterized by a corresponding start methylation site, a corresponding end methylation site and, for each different fragment methylation pattern observed across the first plurality of fragments in the first dataset between the corresponding start methylation site and the corresponding end methylation site of the respective node, a representation of the different fragment methylation pattern and a count of fragments in the first dataset whose fragment methylation pattern begins at the corresponding start methylation site and ends at the corresponding end methylation site and has the different fragment methylation pattern.

The method further comprises generating one or more second state interval maps for one or more corresponding genomic regions using the second dataset. Each second state interval map in the one or more second state interval maps comprises a corresponding independent plurality of nodes. In some embodiments the corresponding independent plurality of nodes comprises more than 50 nodes, more than 100 nodes, more than 500 node, more than 1000 nodes, more than 10,000 nodes, more than 100,000 nodes, more than 1 million nodes or more than 1 million nodes. Each respective node in each corresponding independent plurality of nodes in the one or more second state interval maps is characterized by a corresponding start methylation site, a corresponding end methylation site and, for each different fragment methylation pattern observed across the second plurality of fragments in the second dataset between the corresponding start methylation site and the corresponding end methylation site of the respective node, a representation of the different fragment methylation pattern and a count of fragments in the second dataset whose fragment methylation pattern begins at the corresponding start methylation site and ends at the corresponding end methylation site and has the different fragment methylation pattern.

The method further comprises scanning the one or more first interval maps and the one or more second interval maps for a plurality of qualifying methylation patterns (or QMPs), each such methylation pattern having a length that is in a predetermined CpG site number range (e.g., a length of 5 refers to 5 CpG sites, preferably contiguous on the same nucleic acid fragment; a typical qualifying methylation pattern disclosed herein contains between 5 CpG and 20 CpG sites), within the fragment methylation patterns of the one or more first interval maps and the one or more second interval maps. In some embodiments, the predetermined CpG site number range includes a set of different lengths of qualifying methylation patterns (or QMPs), for example, a length in the set can include between three CpG sites and 50 CpG sites, between four CpG sites and thirty CpG sites, or between five CpG sites and twenty-five CpG sites. In some embodiments, the predetermined CpG site number ranges is a single CpG number (e.g, 1, the length of the CpG interval/ between a corresponding initial CpG site and a corresponding final CpG site, which can often be the number of CpG sites starting at the initial CpG site and ending at the final CpG site). In some embodiments, each qualifying methylation pattern in the plurality of qualifying methylation patterns spans a corresponding length/between a corresponding initial CpG site and a corresponding final CpG site. In this way, the plurality of qualifying methylation patterns that discriminates or indicates a cancer condition is identified. In some embodiments, the plurality of qualifying methylation patterns further satisfies one or more selection criteria (e.g., in addition to the length requirement.).

In some embodiments, the one or more selection criteria specifies that a methylation pattern is represented in the one or more first interval maps with a first frequency that satisfies a first frequency threshold, is represented in the one or more first interval maps with a coverage that satisfies a first state depth threshold, and is represented in the one or more second interval maps with a second frequency that satisfies a second frequency threshold.

In some such embodiments, the methylation pattern is represented in the one or more first interval maps with a first frequency that satisfies a first frequency threshold when the frequency of the methylation pattern in the one or more first interval maps exceeds the first frequency threshold, the methylation pattern is represented in the one or more first interval maps with a coverage that satisfies the first state depth threshold when the coverage of the methylation pattern in the one or more first interval maps exceeds the first state depth threshold, and the methylation pattern is represented in the one or more second interval maps with a second frequency that satisfies the second frequency threshold when the frequency of the methylation pattern in the one or more second interval maps is less than the second frequency threshold.

In some such embodiments, the first frequency threshold is 0.2, the first state depth threshold is 10, and the second frequency threshold is 0.001.

In some embodiments, a respective methylation pattern satisfies the one or more selection criteria when the expression:

$$-\log_{10}\left(\frac{\text{second count}}{\text{second state depth}}\right)$$

for the methylation pattern exceeds 3, 4, 5 or 6, where second count is a count of the respective methylation pattern in the one or more second state interval maps, and second state depth is a coverage by the second dataset in the region of genome represented by the respective methylation pattern in the one or more second state interval maps.

In some embodiments, the method further comprises training a classifier to discriminate or indicate a state of the cancer condition using methylation pattern information associated with the plurality of qualifying methylation patterns in the first and second datasets. In some such embodiments, the training may include using additional datasets such as cell-free nucleic acid methylation data from individual subjects, each having the first or second state, that have been individually matched to a tumor biopsy in order to screen out germline mutations from the cell-free nucleic acid methylation data. In other embodiments, the training may include an additional dataset, such as cell-free nucleic acid methylation data from individual subjects, each having the first or second state, that have not been individually matched to a tumor biopsy and therefore germline mutations have not been screened out based on tumor matching.

In some embodiments, the method further comprises training a classifier to discriminate a state of the cancer condition using methylation pattern information associated with the plurality of qualifying methylation patterns in the first and second datasets.

In some such embodiments, the classifier is logistic regression. In some embodiments, the classifier is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

In some embodiments, the method further comprises obtaining a third dataset, in electronic form, where the third dataset comprises a corresponding fragment methylation pattern of each respective fragment in a third plurality of fragments. The corresponding fragment methylation pattern of each respective fragment is determined by a methylation sequencing of nucleic acids from a biological sample obtained from a test subject and comprises a methylation state of each CpG site in a corresponding plurality of CpG sites in the respective fragment. The method further comprises applying the fragment methylation pattern of each respective fragment in the third plurality of fragments in the third dataset that encompasses or corresponds to a qualifying methylation pattern in the plurality of qualifying methylation patterns to the classifier to thereby determine the state of the cancer condition in the test subject.

In some embodiments, the state of cancer condition is tumor fraction, the first state of the cancer condition is a first range of tumor fraction, and the second state of the cancer condition is a second range of tumor fraction.

In some such embodiments, the first range is greater than 0.001 and the second range is less than 0.001.

In some alternative embodiments, the state of cancer condition is tumor fraction; and the obtaining and applying using the third dataset is repeated on a recurring basis over time.

In some embodiments, the state of the cancer condition is absence or presence of a cancer. In some embodiments, the state of the cancer condition is a stage of cancer.

In some of the disclosed embodiments, the cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the biological sample obtained from the test subject is a liquid biological sample. In some such embodiments, the third plurality of fragments is cell-free nucleic acids.

In some embodiments, the first and second plurality of fragments are cell-free nucleic acids.

In some embodiments, the one or more first state interval maps consist of a single first state interval map; and the one or more second state interval maps consist of a single second state interval map.

In some embodiments, the one or more first state interval maps include or are a plurality of first state interval maps; the one or more second state interval maps include or are a plurality of second state interval maps; the one or more corresponding genomic regions include or are a plurality of genomic regions. For example, each respective genomic region in the plurality of genomic regions is represented by a first state interval map in the first plurality of interval maps and a second state interval map in the second plurality of interval maps. In some embodiments, the plurality of genomic regions is between 10 and 30. In some embodiments, each genomic region in the plurality of genomic regions is a different human chromosome. In some embodiments, the plurality of genomic regions consists of between two and 1000 genomic regions, between 500 and 5,000 genomic regions, between 1,000 and 20,000 genomic regions or between 5,000 and 50,000 genomic regions. In some embodiments, the methylation sequencing of the obtaining the first dataset and the obtaining the second dataset is targeted sequencing using a plurality of probes and each genomic region in the plurality of genomic regions is associated with a probe in the plurality of probes.

In some embodiments, the corresponding independent plurality of nodes of each respective interval map in the one or more first interval maps is arranged as a corresponding tree that represents a corresponding region in the one or more corresponding genomic regions, and each respective node in the corresponding independent plurality of nodes for the respective interval map represents a sub-region of the corresponding genomic region.

In some such embodiments, each corresponding tree arranges the corresponding independent plurality of nodes into a corresponding plurality of leaves in which a parent node for each leaf in the corresponding plurality of leaves references one or more child nodes, the scanning generates a plurality of queries, each respective query in the plurality of queries is for a different candidate methylation pattern of the length l, and each respective query in the plurality of queries is used to perform a matchmaking with the respective query at each respective node in the corresponding independent plurality of nodes of a corresponding tree, further propagate the query to the child nodes of the respective node for further matchmaking of the respective query against the child nodes of the respective node and deliver a result of each matchmaking to a parent node of the respective node. In some such embodiments, the tree is a one-dimensional version of a Kd tree with a randomized surface-area heuristic. In some such embodiments, each possible methylation pattern of length/is sampled by the plurality of queries.

In some embodiments the predetermined CpG site number range is a single predetermined number of CpG sites. In some embodiments the single predetermined number of CpG sites is 3, 4, 5, 6, 7, 8, 9, 10, 11, 12, 13, 14, 15, 16, 17, 18, 19, 20, 25, 30, 40, or up to 50 CpG sites. In some embodiments, the predetermined CpG site number range is for contiguous CpG sites. In some embodiments, the predetermined CpG site number range is a single predetermined number of contiguous CpG sites. In some embodiments the predetermined number of contiguous CpG sites is 3, 4, 5, 6, 7, 8, 9, 10, 11, 12, 13, 14, 15, 16, 17, 18, 19, 20, 25, 30, 40, or up 50 contiguous CpG sites. In some embodiments, the predetermined CpG site number range is between 2 and 100 contiguous CpG sites in a human reference genome.

In some embodiments, the methylation sequencing of a respective biological sample from the corresponding subject in the first set of one or more subjects produces one billion or more, two billion or more, three billion or more, four billion or more, five billion or more, six billion or more, seven billion or more, eight billion or more, nine billion or more, or 10 billion or more fragments that are evaluated for methylation patterns that are included in the first dataset. In some embodiments, the methylation sequencing of a respective biological sample from the corresponding subject in the first set of one or more subjects produces less than one billion fragments or less than 10,000 fragments that are evaluated for methylation patterns that are included in the first dataset.

In some embodiments, there are more than 10,000 CpG sites, more than 25,000 CpG sites, more than 50,000 CpG sites, more than 80,000 CpG sites, more than 100,000 CpG sites, more than 150,000 CpG sites, more than 200,000 CpG sites, more than 300,000 CpG sites, more than 400,000 CpG sites, more than 500,000 CpG sites, more than 600,000 CpG sites, more than 700,000 CpG sites, more than 800,000 CpG sites, more than 900,000 CpG sites, more than 1,000,000 CpG sites, more than 1,200,000 CpG sites, more than 1,800,000 CpG sites, more than 1,800,000 CpG sites, or more than 2,000,000 CpG sites across the one or more corresponding genomic regions. In some embodiments, there are less than 10,000 CpG sites, less than 25,000 CpG sites, less than 50,000 CpG sites, less than 80,000 CpG sites, less than 100,000 CpG sites, less than 150,000 CpG sites, less than 200,000 CpG sites, less than 300,000 CpG sites, less than 400,000 CpG sites, less than 500,000 CpG sites, less than 600,000 CpG sites, less than 700,000 CpG sites, less than 800,000 CpG sites, less than 900,000 CpG sites, less than 1,000,000 CpG sites, less than 1,200,000 CpG sites, less than 1,500,000 CpG sites, less than 1,800,000 CpG sites, or less than 2,000,000 CpG sites across the one or more corresponding genomic regions.

In some embodiments, an average sequence read length of a corresponding plurality of sequence reads obtained by the methylation sequencing for a respective fragment is between 100 and 300 nucleotides; for example, between 140 and 280 nucleotides.

In some embodiments, each genomic region in the one or more corresponding genomic regions represents between 500 base pairs and 10,000 base pairs of a human genome reference sequence. In some embodiments, each genomic region in the one or more corresponding genomic regions represents between 500 base pairs and 2,000 base pairs of a human genome reference sequence. In some embodiments, each genomic region in the one or more corresponding genomic regions represents a different portion of a human genome reference sequence. In some embodiments, the one or more corresponding genomic regions collectively cover up to 1 million base pair (Mb), 2 Mb, 3 Mb, 5 Mb, 8 Mb, 10 Mb, 12 Mb, 15 Mb, 20 Mb, 25 Mb, 30 Mb, 40 Mb, or 50 Mb of a human genome reference sequence.

In some embodiments, the methylation state of a CpG site in the corresponding plurality of CpG sites is methylated when the CpG site is determined by the methylation sequencing to be methylated, and unmethylated when the CpG site is determined by the methylation sequencing to not be methylated. In some embodiments, the methylation sequencing is whole-genome methylation sequencing or targeted DNA methylation sequencing using a plurality of nucleic acid probes. In some embodiments, the methylation sequencing detects one or more 5-methylcytosine (5 mC) and/or 5-hydroxymethylcytosine (5 hmC) in respective fragments. In some embodiments, the methylation sequencing comprises the conversion of one or more unmethylated cytosines or one or more methylated cytosines to a corresponding one or more uracils. In some embodiments, the one or more uracils are detected during the methylation sequencing as one or more corresponding thymines. In some embodiments, the conversion of one or more unmethylated cytosines or one or more methylated cytosines comprises a chemical conversion, an enzymatic conversion, or combinations thereof.

In some embodiments, the respective biological sample is a blood sample. In some embodiments, the respective biological sample comprises blood, whole blood, plasma, serum, urine, cerebrospinal fluid, fecal, saliva, sweat, tears, pleural fluid, pericardial fluid, or peritoneal fluid.

In some embodiments, the cancer condition is a tumor fraction in a test subject, the first set of subjects consists of the test subject, the first state of the cancer condition is the tumor fraction in the test subject, the second state of the cancer condition is absence of cancer, and the second set of cancer subjects is a plurality of cancer-free subjects. In some embodiments, the method further comprises using the plurality of qualifying methylation patterns to determine the tumor fraction in the test subject. In some embodiments, the method further comprises treating the test subject based on the tumor fraction determined for the test subject. In some embodiments, the method further comprises adjusting an ongoing treatment regimen of the test subject based on the tumor fraction determined for the test subject.

In some embodiments, the first state of the cancer condition is unique to a test subject, the first set of subjects consists of the test subject, the second state of the cancer condition is absence of cancer, and the second set of cancer subjects is a plurality of cancer-free subjects. In some embodiments, the method further comprises using the plurality of qualifying methylation patterns to quantify the first state of the cancer condition in the test subject. In some embodiments, the method further comprises treating the test subject based on the quantification of the first state of the cancer condition in the test subject. In some embodiments, method further comprises adjusting an ongoing treatment regimen of the test subject based on the quantification of the first state of the cancer condition in the test subject. In some embodiments, the test subject has adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, or leukemia.

In some embodiments, the cancer condition is an absence or presence of a cancer, the first set of subjects comprises a first plurality of subjects, the first state of the cancer condition is presence of the cancer, the second state of the cancer condition is absence of the cancer, and the second set of cancer subjects is a second plurality of cancer subjects. In some embodiments, the cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, or leukemia, In some embodiments, the cancer condition is an origin of a cancer, the first set of subjects comprises a first plurality of subjects, the first state of the cancer condition is a first origin of a cancer, the second state of the cancer condition is a second origin of a cancer, and the second set of cancer subjects is a second plurality of cancer subjects. In some embodiments, the first origin is one of adrenal, biliary, bladder, bone/bone marrow, brain, breast, cervical, colorectal, esophagus, gastric, head/neck, hepatobiliary, kidney, liver, lung, ovarian, pancreatic, pelvis, pleura, prostate, renal, skin, stomach, testis, thymus, thyroid, uterine, lymphoma, melanoma, multiple myeloma, or leukemia, and the second origin is other than the first origin and is one of adrenal, biliary, bladder, bone/bone marrow, brain, breast, cervical, colorectal, esophagus, gastric, head/neck, hepatobiliary, kidney, liver, lung, ovarian, pancreatic, pelvis, pleura, prostate, renal, skin, stomach, testis, thymus, thyroid, uterine, lymphoma, melanoma, multiple myeloma, or leukemia.

In some embodiments, the cancer condition is a stage of a cancer, the first set of subjects comprises a first plurality of subjects, the first state of the cancer condition is a first stage of the first cancer, the second state of the cancer condition is a second stage of the first cancer, and the second set of cancer subjects is a second plurality of cancer subjects. In some embodiments, the cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, or leukemia, the first stage is stage I, II, III, or IV of the cancer, and the second stage is other than the first stage and is stage I, II, III, or IV of the cancer.

Another aspect of the present disclosure provides a computer system for identifying a plurality of qualifying methylation patterns that discriminate or indicate a cancer condition, the computer system comprising at least one processor and a memory storing at least one program for execution by the at least one processor, the at least one program comprising instructions for identifying a plurality of qualifying methylation patterns that discriminate or indicate a cancer condition. In some embodiments, the at least one program is configured for execution by a computer. In some embodiments, the at least one program comprises instructions for performing any of the methods and embodiments disclosed herein, and/or any combinations thereof as will be apparent to one skilled in the art.

Another aspect of the present disclosure provides a non-transitory computer-readable storage medium having stored thereon program code instructions that, when executed by a processor, cause the processor to perform a method for identifying a plurality of qualifying methylation patterns that discriminate or indicate a cancer condition. In some embodiments, the program code instructions are configured for execution by a computer. In some embodiments, the program code instructions comprise instructions for performing any of the methods and embodiments disclosed herein, and/or any combinations thereof as will be apparent to one skilled in the art.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 2A, 2B, 2C, 2D, 2E, and 2F collectively illustrate an example flowchart of a method of identifying methylation patterns that discriminate or indicate a cancer condition in which dashed boxes represent optional steps in accordance with some embodiments of the present disclosure.

FIG. 9 illustrates an example flowchart of a method for obtaining methylation information for the purposes of screening for a cancer condition in a test subject in accordance with some embodiments of the present disclosure.

FIGS. 13A and 13B illustrate example approaches based on the small variants in accordance with some embodiments of the present disclosure.

FIGS. 14A and 14B illustrate a WGBS example in which, instead of small variants, selected methylation patterns (e.g., qualifying methylation patterns or QMPs) are used as basis for estimating tumor fractions based on methylation sequencing data, for instance when small variant identification is compromised by factors such as bisulfite conversion, in accordance with the present disclosure.

FIGS. 15A and 15B illustrate a TM sequencing example in which, instead of small variants, selected methylation patterns (e.g., qualifying methylation patterns or QMPs) are used as basis for estimating tumor fractions based on methylation sequencing data, especially when small variant identification is compromised by factors such as bisulfite conversion, in accordance with the present disclosure.

DETAILED DESCRIPTION

Figure 1:
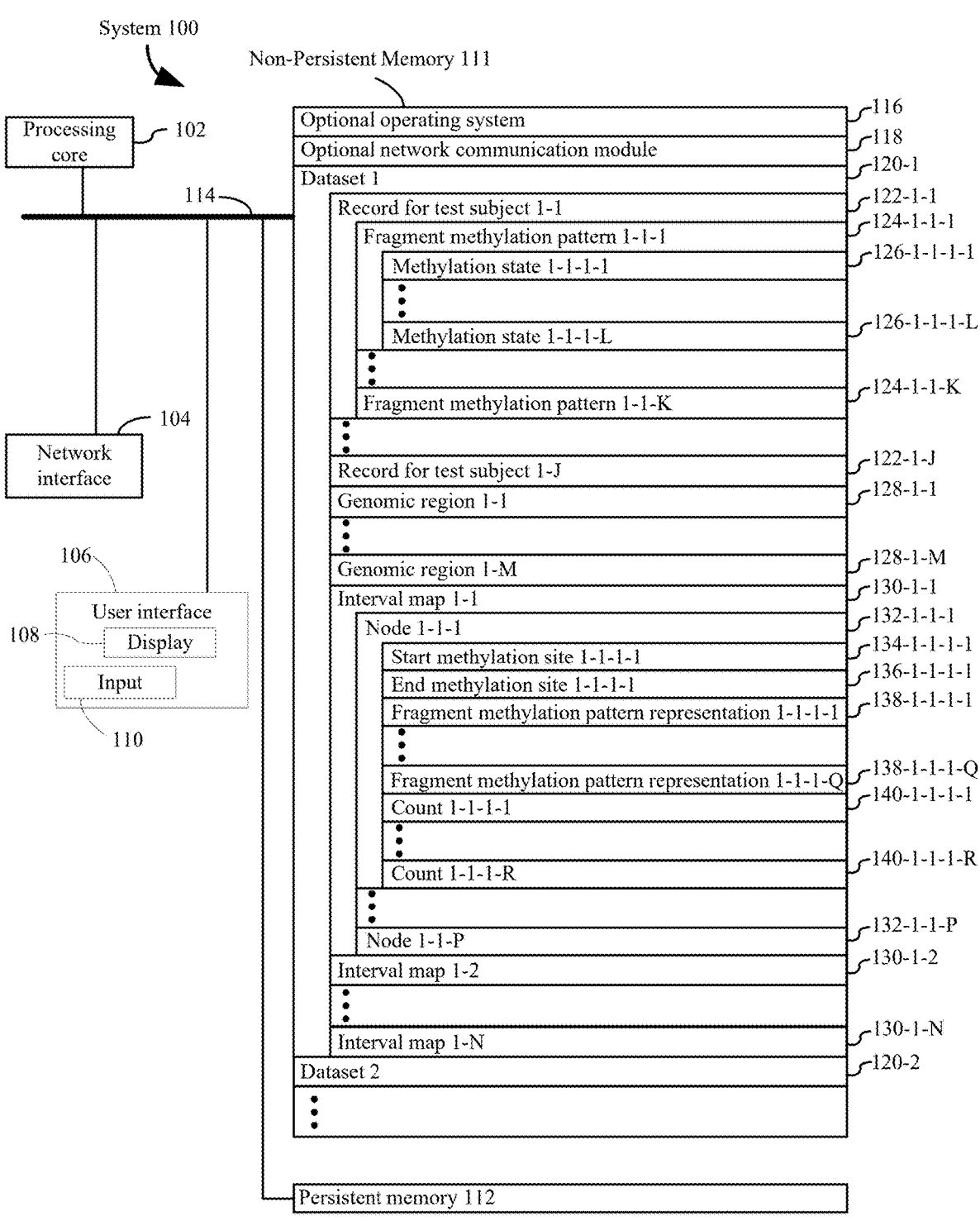
FIG. 1 illustrates an example block diagram illustrating a computing device in accordance with some embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions for identifying qualifying methylation patterns discriminating or indicating a cancer condition. Specifically, a first dataset and a second dataset are obtained (e.g., in electronic form). Each respective dataset comprises a corresponding fragment methylation pattern for each respective fragment in a respective first or second plurality of fragments. The corresponding methylation pattern of each respective fragment is determined by methylation sequencing of nucleic acids obtained from a respective first or second set of subjects and comprises a methylation state of each CpG site in a corresponding plurality of CpG sites. Each respective plurality of subjects has a respective first or second state of the cancer condition. A first interval map and a second interval map are generated for each respective dataset, comprising a plurality of nodes characterized by a start methylation site, an end methylation site, a representation of each different fragment methylation pattern and a count of fragments. The first and second interval maps are scanned for qualifying fragment methylation patterns in a predetermined CpG site number range, satisfying one or more selection criteria, thereby identifying fragment methylation patterns that discriminate or indicate a cancer condition.

Definitions.

As used herein, the terms "about" and "approximately" means within an acceptable error range for the particular value as determined by one of ordinary skill in the art, which depends in part on how the value is measured or determined, e.g., the limitations of the measurement system. For example, in some embodiments "about" mean within 1 or more than 1 standard deviation, per the practice in the art. In some embodiments, "about" means a range of ±20%, ±10%, ±5%, or ±1% of a given value. In some embodiments, the term "about" or "approximately" means within an order of magnitude, within 5-fold, or within 2-fold, of a value. Where particular values are described in the application and claims, unless otherwise stated the term "about" meaning within an acceptable error range for the particular value can be assumed. The term "about" can have the meaning as commonly understood by one of ordinary skill in the art. In some embodiments, the term "about" refers to ±10%. In some embodiments, the term "about" refers to ±5%.

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

As disclosed herein, the term "biological sample" refers to any sample taken from a subject, which can reflect a biological state associated with the subject, and that includes cell-free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As disclosed herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, super-coiled, single-stranded, double-stranded and the like). A nucleic acid in some embodiments can be from a single chromosome or fragment thereof (e.g., a nucleic acid sample may be from one chromosome of a sample obtained from a diploid organism). In certain embodiments, nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense," "plus" strand or "minus" strand, "forward" reading frame or "reverse" reading frame) and double-stranded polynucleotides. Deoxyribonucleotides include deoxyadenosine, deoxycytidine, deoxyguanosine, and deoxythymidine. For RNA, the base cytosine is replaced with uracil and the sugar 2' position includes a hydroxyl moiety. A nucleic acid may be prepared using a nucleic acid obtained from a subject as a template.

As disclosed herein, the terms "cell-free nucleic acid," "cell-free DNA," and "cfDNA" interchangeably refer to nucleic acid fragments that circulate in a subject's body (e.g., in a bodily fluid such as the bloodstream) and originate from one or more healthy cells and/or from one or more cancer cells. The cfDNA may be recovered from bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids are used interchangeably with circulating nucleic acids. Examples of the cell-free nucleic acids include but are not limited to RNA, mitochondrial DNA, or genomic DNA.

As disclosed herein, the term "circulating tumor DNA" or "ctDNA" refers to nucleic acid fragments that originate from aberrant tissue, such as the cells of a tumor or other types of cancer, which may be released into a subject's bloodstream as result of biological processes such as apoptosis or necrosis of dying cells or actively released by viable tumor cells.

As disclosed herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the online genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As disclosed herein, the term "regions of a reference genome," "genomic region," or "chromosomal region"

refers to any portion of a reference genome, contiguous or non-contiguous. It can also be referred to, for example, as a bin, a partition, a genomic portion, a portion of a reference genome, a portion of a chromosome and the like. In some embodiments, a genomic section is based on a particular length of genomic sequence. In some embodiments, a method can include analysis of multiple mapped sequence reads to a plurality of genomic regions. Genomic regions can be approximately the same length or the genomic sections can be different lengths. In some embodiments, genomic regions are of about equal length. In some embodiments, genomic regions of different lengths are adjusted or weighted. In some embodiments, a genomic region is about 10 kilobases (kb) to about 500 kb, about 20 kb to about 400 kb, about 30 kb to about 300 kb, about 40 kb to about 200 kb, and sometimes about 50 kb to about 100 kb. In some embodiments, a genomic region is about 100 kb to about 200 kb. A genomic region is not limited to contiguous runs of sequence. Thus, genomic regions can be made up of contiguous and/or non-contiguous sequences. A genomic region is not limited to a single chromosome. In some embodiments, a genomic region includes all or part of one chromosome or all or part of two or more chromosomes. In some embodiments, genomic regions may span one, two, or more entire chromosomes. In addition, the genomic regions may span joint or disjointed portions of multiple chromosomes.

As used herein, the terms "fragment" and "nucleic acid fragment," used interchangeably herein, refer to all or a portion of a polynucleotide sequence of at least three consecutive nucleotides. In the context of sequencing nucleic acid fragments found in a biological sample, the term "fragment" refers to a nucleic acid molecule (e.g., a DNA fragment) that is found in the biological sample or a representation thereof (e.g., an electronic representation of the sequence). Sequencing data (e.g., raw or corrected sequence reads from whole-genome sequencing, targeted sequencing, etc.) from a unique fragment (e.g., a cell-free nucleic acid) are used to determine a nucleic acid fragment sequence and/or a methylation pattern of the fragment. Such sequence reads, which in fact may be obtained from sequencing of PCR duplicates of the original fragment, therefore "represent" or "support" the fragment sequence. There may be a plurality of sequence reads that each represents or supports a particular fragment in a biological sample (e.g., PCR duplicates), however, there may be one fragment sequence, and one fragment methylation pattern, for the particular fragment. In some embodiments, duplicate sequence reads generated for the original fragment are combined or removed (e.g., collapsed into a single sequence, e.g., the nucleic acid fragment sequence). Accordingly, when determining metrics relating to a population of fragments, in a sample, that each encompass a particular locus (e.g., an abundance value for the locus or a metric based on a characteristic of the distribution of the fragment lengths), the nucleic acid fragment sequences for the population of fragments, rather than the supporting sequence reads (e.g., which may be generated from PCR duplicates of the nucleic acid fragments in the population) can be used to determine the metric. This is because, in such embodiments, one copy of the sequence is used to represent the original (e.g., unique) fragment (e.g., unique nucleic acid molecule). It is noted that the fragments for a population of fragments may include several identical sequences, with the same or different fragment methylation pattern, each of which represents a different original fragment, rather than duplicates of the same original fragment. In some embodiments, a cell-free nucleic acid is considered a fragment.

The terms "sequence reads" or "reads," used interchangeably herein, refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). In some embodiments, sequence reads (e.g., single-end or paired-end reads) can be generated from one or both strands of a targeted nucleic acid fragment. The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As disclosed herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

The terms "sequencing depth," "coverage" and "coverage rate" are used interchangeably herein to refer to the number of times a locus is covered by a consensus sequence read corresponding to a unique nucleic acid target molecule ("nucleic acid fragment") aligned to the locus; e.g., the sequencing depth is equal to the number of unique nucleic acid target fragments (excluding PCR sequencing duplicates) covering the locus. The locus can be as small as a nucleotide, or as large as a chromosome arm, or as large as an entire genome. Sequencing depth can be expressed as "YX", e.g., 50×, 100×, etc., where "Y" refers to the number of times a locus is covered with a sequence corresponding to a nucleic acid target; e.g., the number of times independent sequence information is obtained covering the particular locus. In some embodiments, the sequencing depth corresponds to the number of genomes that have been sequenced. Sequencing depth can also be applied to multiple loci, or the whole genome, in which case Y can refer to the mean or average number of times a loci or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As disclosed herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "methylation" refers to a modification of deoxyribonucleic acid (DNA) where a hydrogen atom on the pyrimidine ring of a cytosine base is converted to a methyl group, forming 5-methylcytosine. In particular, methylation tends to occur at dinucleotides of cytosine and guanine referred to herein as "CpG sites". In other instances, methylation may occur at a cytosine not part of a CpG site or at another nucleotide that's not cytosine; however, these are rarer occurrences. In this present disclosure, methylation is discussed in reference to CpG sites for the sake of clarity. Anomalous cfDNA methylation can be identified as hypermethylation or hypomethylation, both of which may be indicative of cancer status. As is well known in the art, DNA methylation anomalies (compared to healthy controls) can cause different effects, which may contribute to cancer.

Various challenges arise in the identification of anomalously methylated cfDNA fragments. First, determining a subject's cfDNA to be anomalously methylated only holds weight in comparison with a group of control subjects, such that if the control group is small in number, the determination loses confidence with the small control group. Additionally, among a group of control subjects' methylation status can vary which can be difficult to account for when determining a subject's cfDNA to be anomalously methylated. On another note, methylation of a cytosine at a CpG site causally influences methylation at a subsequent CpG site.

The principles described herein are equally applicable for the detection of methylation in a non-CpG context, including non-cytosine methylation. Further, the methylation state vectors may contain elements that are generally vectors of sites where methylation has or has not occurred (even if those sites are not CpG sites specifically). With that substitution, the remainder of the processes described herein are the same, and consequently, the inventive concepts described herein are applicable to those other forms of methylation.

As used herein, the term "methylation profile" (also called methylation status) can include information related to DNA methylation for a region. Information related to DNA methylation can include a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes can refer to the addition of a methyl group to position 5 of the heterocyclic ring of cytosine (e.g., to produce 5-methylcytosine) among CpG dinucleotides. Methylation of cytosine can occur in cytosines in other sequence contexts, for example, 5'-CHG-3' and 5'-CHH-3', where His adenine, cytosine or thymine. Cytosine methylation can also be in the form of 5-hydroxymethylcytosine. Methylation of DNA can include methylation of non-cytosine nucleotides, such as N6-methyladenine.

As used herein a "methylome" can be a measure of an amount of DNA methylation at a plurality of sites or loci in a genome. The methylome can correspond to all of a genome, a substantial part of a genome, or relatively small portion(s) of a genome. A "tumor methylome" can be a methylome of a tumor of a subject (e.g., a human). A tumor methylome can be determined using tumor tissue or cell-free tumor DNA in plasma. A tumor methylome can be one example of a methylome of interest. A methylome of interest can be a methylome of an organ that can contribute nucleic acid, e.g., DNA into a bodily fluid (e.g., a methylome of brain cells, a bone, lungs, heart, muscles, kidneys, etc.). The organ can be a transplanted organ.

As used herein the term "methylation index" for each genomic site (e.g., a CpG site, a region of DNA where a cytosine nucleotide is followed by a guanine nucleotide in the linear sequence of bases along its 5'→3' direction) can refer to the proportion of sequence reads showing methylation at the site over the total number of reads covering that site. The "methylation density" of a region can be the number of reads at sites within a region showing methylation divided by the total number of reads covering the sites in the region. The sites can have specific characteristics, (e.g., the sites can be CpG sites). The "CpG methylation density" of a region can be the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of unconverted cytosines (which can correspond to methylated cytosine) at CpG sites as a proportion of all CpG sites covered by sequence reads mapped to the 100-kb region. In some embodiments, this analysis is performed for other bin sizes, e.g., 50-kb or 1-Mb, etc. In some embodiments, a region is an entire genome or a chromosome or part of a chromosome (e.g., a chromosomal arm). A methylation index of a CpG site can be the same as the methylation density for a region when the region only includes that CpG site. The "proportion of methylated cytosines" can refer the number of cytosine sites, "C's," that are shown to be methylated (for example unconverted after bisulfite conversion) over the total number of analyzed cytosine residues, e.g., including cytosines outside of the CpG context, in the region. The methylation index, methylation density and proportion of methylated cytosines are examples of "methylation levels."

As used herein, a "plasma methylome" can be the methylome determined from plasma or serum of an animal (e.g., a human). A plasma methylome can be an example of a cell-free methylome since plasma and serum can include cell-free DNA. A plasma methylome can be an example of a mixed methylome since it can be a mixture of tumor/patient methylome. A "cellular methylome" can be a methylome determined from cells (e.g., blood cells or tumor cells) of a subject, e.g., a patient. A methylome of blood cells can be called a blood cell methylome (or blood methylome).

As used herein, the term "relative abundance" can refer to a ratio of a first amount of nucleic acid fragments having a particular characteristic (e.g., a specified length, ending at one or more specified coordinates/ending positions, aligning to a particular region of the genome, or having a particular methylation status) to a second amount nucleic acid fragments having a particular characteristic (e.g., a specified length, ending at one or more specified coordinates/ending positions, or aligning to a particular region of the genome). In one example, relative abundance may refer to a ratio of the number of DNA fragments ending at a first set of genomic positions to the number of DNA fragments ending at a second set of genomic positions. In some aspects, a "relative abundance" can be a type of separation value that relates an amount (one value) of cell-free DNA molecules ending within one window of genomic position to an amount (other value) of cell-free DNA molecules ending within another window of genomic positions. The two windows can overlap, but can be of different sizes. In other embodiments, the two windows cannot overlap. Further, in some embodiments, the windows are of a width of one nucleotide, and therefore are equivalent to one genomic position.

As used herein, the term "methylation pattern" refers to a sequence of methylation states for one or more CpG sites. Methylation states include, but are not limited to, methylated (e.g., represented as "M") and unmethylated (e.g., represented as "U"). For example, a methylation pattern spanning 5 CpG sites may be represented as "MMMMM" or "UUUUU," where each discrete symbol represents a methylation state at a single CpG site. A methylation pattern may or may not correspond to a specific genomic location and/or a specific one or more CpG sites in a reference genome.

As used herein, the term "fragment methylation pattern" refers to a methylation pattern of a fragment (e.g., of a nucleic acid sample) or a portion of a fragment. In the disclosure, the term "fragment methylation pattern" is used interchangeably with the term "FMP" unless otherwise noted. The fragment methylation pattern may be obtained by methylation sequencing of a respective nucleic acid sample. In some embodiments, one or more fragments obtained from a nucleic acid sample are aligned to a reference genome, such that each respective fragment methylation pattern comprises one or more CpG sites (e.g., a span or interval of CpG sites), where each respective CpG site comprises a respective methylation state and is indexed to a specific site in a reference genome. Thus, the one or more CpG sites in a respective fragment methylation pattern corresponds to a specific location in a reference genome, and a fragment methylation pattern refers to a sequence of methylation states for one or more CpG sites corresponding to a specific location in a reference genome. In some embodiments, each fragment in a plurality of fragments has a corresponding fragment methylation pattern. A fragment methylation pattern can be represented by a representation of a sequence of methylation states (e.g., "MMMMM" or "UUUUU"). In some embodiments, a plurality of fragment methylation patterns for a respective plurality of fragments is represented by an interval map comprising representations of each fragment methylation pattern (e.g., nodes) in the plurality of fragment methylation patterns for the respective plurality of fragments.

As used herein, the term "query methylation pattern" refers to a sequence of methylation states that is in a predetermined CpG site number range. A query methylation pattern can be a representation of a sequence of methylation states (e.g., "MMMMM" or "UUUUU") that are used for querying representations of methylation patterns (e.g., for a plurality of fragment methylation patterns represented by an interval map). In some embodiments, a query methylation pattern corresponds to one or more CpG sites (e.g., a span or interval of CpG sites) indexed to a respective one or more specific sites in a reference genome. In some embodiments, a query methylation pattern does not correspond to either a specific CpG site or a specific location in a reference genome (for example, where a query methylation pattern is a representation of a sequence of methylation states to be queried across all locations within a genomic region and/or reference genome). In some instances, the predetermined CpG site number range is user defined (e.g., the range 5 CpG sites to 20 CpG sites). In some instances, the predetermined CpG site number range is a single number meaning, in such instances, that the query methylation pattern is a fixed CpG number length (e.g., 5 CpG sites). In some embodiments, a fragment methylation pattern/FMP or a portion thereof can be used as a query methylation pattern. In some embodiments, query methylation patterns from a previously generated query library can used. In some embodiments, one or more query libraries can be generated for a specific disease condition such as a specific type of cancer.

As used herein, the term "qualifying methylation pattern" refers to a methylation pattern that is in a predetermined CpG site number range, satisfying one or more selection criteria. In the disclosure, the term "qualifying methylation pattern" is used interchangeably with the term "QMP" unless otherwise specified. In some embodiments, a qualifying methylation pattern corresponds to one or more CpG sites (e.g., a span or interval of CpG sites) indexed to a respective one or more specific sites in a reference genome. For example, where a qualifying methylation pattern is identified in a respective one or more fragments in a plurality of fragments aligned to a reference genome, the qualifying methylation pattern comprises one or more CpG sites, where each respective CpG site comprises a respective methylation state and is indexed to a specific site in a reference genome. Thus, in some such embodiments, a qualifying methylation pattern refers to a specific sequence of methylation states at a specific location in a reference genome that satisfies the one or more selection criteria. A qualifying methylation pattern (e.g., a representation of a respective sequence of methylation states for the qualifying methylation pattern such as "MMMMM" or "UUUUU") may be identified in a respective one or more fragments in a plurality of fragments aligned to a reference genome, where the respective fragment methylation patterns for the plurality of fragments are represented by an interval map, by matching query methylation patterns to representations of each fragment methylation pattern in each node in the interval map, and determining whether the matched methylation patterns satisfy the one or more selection criteria. In some embodiments, a qualifying methylation pattern does not correspond to either a specific CpG site or a specific location in a reference genome (e.g., if the genomic location of the one or more CpG sites in the qualifying methylation is unknown and/or if the sequence of methylation states in the qualifying methylation pattern occurs at multiple locations throughout a reference genome).

As disclosed herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale, and shark. The terms "subject" and "patient" are used interchangeably herein and refer to a human or non-human animal who is known to have, or potentially has, a medical condition or disorder, such as, e.g., a cancer. In some embodiments, a subject is a male or female of any stage (e.g., a man, a women or a child).

A subject from whom a sample is taken, or is treated by any of the methods or compositions described herein can be of any age and can be an adult, infant or child. In some cases, the subject, e.g., patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old). A particular class of subjects, e.g., patients that can benefit from a method of the present disclosure is subjects, e.g., patients over the age of 40.

Another particular class of subjects, e.g., patients that can benefit from a method of the present disclosure is pediatric patients, who can be at higher risk of chronic heart symptoms. Furthermore, a subject, e.g., patient from whom a sample is taken, or is treated by any of the methods or compositions described herein, can be male or female.

The term "normalize" as used herein means transforming a value or a set of values to a common frame of reference for comparison purposes. For example, when a diagnostic ctDNA level is "normalized" with a baseline ctDNA level, the diagnostic ctDNA level is compared to the baseline ctDNA level so that the amount by which the diagnostic ctDNA level differs from the baseline ctDNA level can be determined.

As used herein the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: a degree of cellular differentiation including morphology and functionality, rate of growth, local invasion and metastasis. A "benign" tumor can be well-differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

As used herein, the term "cancer condition" refers to a condition of a sample relative to cancer, where each potential characteristic and/or measure of the condition refers to a "state" of the cancer condition. For example, a sample can have a cancer condition that is "cancer" or "non-cancer." Moreover, a cancer condition can be a state that affects the prognosis of a cancer, such as the absence/presence of particular mutations known to affect a cancer condition, covariates such as smoking/non-smoking, age, gender, and/or hematopoietic status, etc. Alternatively, a cancer condition can be a primary site of origin or a tissue-of-origin, such as healthy breast, lung, prostate, colorectal, renal, uterine, pancreatic, esophageal, lymph, head/neck, ovarian, liver, cervical, epidermal, thyroid, bladder, gastric, or a combination thereof, or breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, gastric cancer, or a combination thereof. A cancer condition can be a cancer type or a tumor of a certain cancer type, or a fraction thereof, such as an adrenocortical carcinoma, a childhood adrenocortical carcinoma, a tumor of an AIDS-related cancer, kaposi sarcoma, a tumor associated with anal cancer, a tumor associated with an appendix cancer, an astrocytoma, a childhood (brain cancer) tumor, an atypical teratoid/rhabdoid tumor, a central nervous system (brain cancer) tumor, a basal cell carcinoma of the skin, a tumor associated with bile duct cancer, a bladder cancer tumor, a childhood bladder cancer tumor, a bone cancer (e.g., ewing sarcoma and osteosarcoma and malignant fibrous histiocytoma) tissue, a brain tumor, breast cancer tissue, childhood breast cancer tissue, a childhood bronchial tumor, burkitt lymphoma tissue, a carcinoid tumor (gastrointestinal), a childhood carcinoid tumor, a carcinoma of unknown primary, a childhood carcinoma of unknown primary, a childhood cardiac (heart) tumor, a central nervous system (e.g., brain cancer such as childhood atypical teratoid/rhabdoid) tumor, a childhood embryonal tumor, a childhood germ cell tumor, cervical cancer tissue, childhood cervical cancer tissue, cholangiocarcinoma tissue, childhood chordoma tissue, a chronic myeloproliferative neoplasm, a colorectal cancer tumor, a childhood colorectal cancer tumor, childhood craniopharyngioma tissue, a ductal carcinoma in situ (DCIS), a childhood embryonal tumor, endometrial cancer (uterine cancer) tissue, childhood ependymoma tissue, esophageal cancer tissue, childhood esophageal cancer tissue, esthesioneuroblastoma (head and neck cancer) tissue, a childhood extracranial germ cell tumor, an extragonadal germ cell tumor, eye cancer tissue, an intraocular melanoma, a retinoblastoma, fallopian tube cancer tissue, gallbladder cancer tissue, gastric (stomach) cancer tissue, childhood gastric (stomach) cancer tissue, a gastrointestinal carcinoid tumor, a gastrointestinal stromal tumor (GIST), a childhood gastrointestinal stromal tumor, a germ cell tumor (e.g., a childhood central nervous system germ cell tumor, a childhood extracranial germ cell tumor, an extragonadal germ cell tumor, an ovarian germ cell tumor, or testicular cancer tissue), head and neck cancer tissue, a childhood heart tumor, hepatocellular cancer (HCC) tissue, an islet cell tumor (pancreatic neuroendocrine tumors), kidney or renal cell cancer (RCC) tissue, laryngeal cancer tissue, leukemia, liver cancer tissue, lung cancer (non-small cell and small cell) tissue, childhood lung cancer tissue, male breast cancer tissue, a malignant fibrous histiocytoma of bone and osteosarcoma, a melanoma, a childhood melanoma, an intraocular melanoma, a childhood intraocular melanoma, a merkel cell carcinoma, a malignant mesothelioma, a childhood mesothelioma, metastatic cancer tissue, metastatic squamous neck cancer with occult primary tissue, a midline tract carcinoma with NUT gene changes, mouth cancer (head and neck cancer) tissue, multiple endocrine neoplasia syndrome tissue, a multiple myeloma/plasma cell neoplasm, myelodysplastic syndrome tissue, a myelodysplastic/myeloproliferative neoplasm, a chronic myeloproliferative neoplasm, nasal cavity and paranasal sinus cancer tissue, nasopharyngeal cancer (NPC) tissue, neuroblastoma tissue, non-small cell lung cancer tissue, oral cancer tissue, lip and oral cavity cancer and oropharyngeal cancer tissue, osteosarcoma and malignant fibrous histiocytoma of bone tissue, ovarian cancer tissue, childhood ovarian cancer tissue, pancreatic cancer tissue, childhood pancreatic cancer tissue, papillomatosis (childhood laryngeal) tissue, paraganglioma tissue, childhood paraganglioma tissue, paranasal sinus and nasal cavity cancer tissue, parathyroid cancer tissue, penile cancer tissue, pharyngeal cancer tissue, pheochromocytoma tissue, childhood pheochromocytoma tissue, a pituitary tumor, a plasma cell neoplasm/multiple myeloma, a pleuropulmonary blastoma, a primary central nervous system (CNS) lymphoma, primary peritoneal cancer tissue, prostate cancer tissue, rectal cancer tissue, a retinoblastoma, a childhood rhabdomyosarcoma, salivary gland cancer tissue, a sarcoma (e.g., a childhood vascular tumor, osteosarcoma, uterine sarcoma, etc.), Sezary syndrome (lymphoma) tissue, skin cancer tissue, childhood skin cancer tissue, small cell lung cancer tissue, small intestine cancer tissue, a squamous cell carcinoma of the skin, a squamous neck cancer with occult primary, a cutaneous t-cell lymphoma, testicular cancer tissue, childhood testicular cancer tissue, throat cancer (e.g., nasopharyngeal cancer, oropharyngeal cancer, hypopharyngeal cancer) tissue, a thymoma or thymic carcinoma, thyroid cancer tissue, transitional cell cancer of the renal pelvis and ureter tissue, unknown primary carcinoma tissue, ureter or renal pelvis tissue, transitional cell cancer (kidney (renal cell) cancer tissue, urethral cancer tissue, endometrial uterine cancer tissue, uterine sarcoma tissue, vaginal cancer tissue, childhood vaginal cancer tissue, a vascular tumor, vulvar cancer tissue, a Wilms tumor or other childhood kidney tumor. A cancer condition can be a stage of cancer, such as a stage of a breast cancer, a stage of a lung cancer, a stage of a prostate cancer, a stage of a colorectal cancer, a stage of a renal cancer, a stage of a uterine cancer, a stage of a pancreatic cancer, a stage of a cancer of the esophagus, a stage of a lymphoma, a stage of a head/neck cancer, a stage of a ovarian cancer, a stage of a hepatobiliary cancer, a stage of a melanoma, a stage of a cervical cancer, a stage of a multiple myeloma, a stage of a leukemia, a stage of a thyroid cancer, a stage of a bladder cancer, or a stage of a gastric cancer. Multiple samples from a single subject can have different cancer conditions or the same cancer condition. Multiple subjects can have different cancer conditions or the same cancer condition.

The terms "cancer load," "tumor load," "cancer burden", "tumor burden", or "tumor fraction" are used interchangeably herein to refer to the fraction of nucleic acids in a test sample that are tumor derived. For instance, in the case of cell-free nucleic acid, the "tumor fraction" can refer to the fraction of the cell-free nucleic acid that is tumor derived. As such, the terms "cancer load," "tumor load," "cancer burden," "tumor burden," and "tumor fraction" are non-limiting examples of a cell source fraction in a biological sample.

As used herein, the term "tissue" corresponds to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein the term "untrained classifier" refers to a classifier that has not been trained on a target dataset. Thus, in some embodiments, "training a classifier" refers to the process of training an untrained classifier. For instance, consider the case of a first canonical set of methylation state vectors and a second canonical set of methylation state vectors discussed below. The respective canonical sets of methylation state vectors are applied as collective input to an untrained classifier, in conjunction with the cell source of each respective reference subject represented by the first canonical set of methylation state vectors (hereinafter "primary training dataset") to train the untrained classifier on cell source thereby obtaining a trained classifier. Moreover, it will be appreciated that the term "untrained classifier" does not exclude the possibility that transfer learning techniques are used in such training of the untrained classifier. For instance, Fernandes et al., 2017, "Transfer Learning with Partial Observability Applied to Cervical Cancer Screening," Pattern Recognition and Image Analysis: 8th Iberian Conference Proceedings, 243-250, which is hereby incorporated by reference, provides non-limiting examples of such transfer learning. In instances where transfer learning is used, the untrained classifier described above is provided with additional data over and beyond that of the primary training dataset. That is, in non-limiting examples of transfer learning embodiments, the untrained classifier receives (i) canonical sets of methylation state vectors and the cell source labels of each of the reference subjects represented by canonical sets of methylation state vectors ("primary training dataset") and (ii) additional data. Typically, this additional data is in the form of coefficients (e.g., regression coefficients) that were learned from another, auxiliary training dataset. Moreover, while a description of a single auxiliary training dataset has been disclosed, it will be appreciated that there is no limit on the number of auxiliary training datasets that may be used to complement the primary training dataset in training the untrained classifier in the present disclosure. For instance, in some embodiments, two or more auxiliary training datasets, three or more auxiliary training datasets, four or more auxiliary training datasets or five or more auxiliary training datasets are used to complement the primary training dataset through transfer learning, where each such auxiliary dataset is different than the primary training dataset. Any manner of transfer learning may be used in such embodiments. For instance, consider the case where there is a first auxiliary training dataset and a second auxiliary training dataset in addition to the primary training dataset. The coefficients learned from the first auxiliary training dataset (by application of a classifier such as regression to the first auxiliary training dataset) may be applied to the second auxiliary training dataset using transfer learning techniques (e.g., the above described two-dimensional matrix multiplication), which in turn may result in a trained intermediate classifier whose coefficients are then applied to the primary training dataset and this, in conjunction with the primary training dataset itself, is applied to the untrained classifier. Alternatively, a first set of coefficients learned from the first auxiliary training dataset (by application of a classifier such as regression to the first auxiliary training dataset) and a second set of coefficients learned from the second auxiliary training dataset (by application of a classifier such as regression to the second auxiliary training dataset) may each individually be applied to a separate instance of the primary training dataset (e.g., by separate independent matrix multiplications) and both such applications of the coefficients to separate instances of the primary training dataset in conjunction with the primary training dataset itself (or some reduced form of the primary training dataset such as principal components or regression coefficients learned from the primary training set) may then be applied to the untrained classifier in order to train the untrained classifier. In either example, knowledge regarding cell source (e.g., cancer type, etc.) derived from the first and second auxiliary training datasets is used, in conjunction with the cell source labeled primary training dataset), to train the untrained classifier.

The term "classification" can refer to any number(s) or other characters(s) that are associated with a particular property of a sample. For example, a "+" symbol (or the word "positive") can signify that a sample is classified as having deletions or amplifications. In another example, the term "classification" refers to an amount of tumor tissue in the subject and/or sample, a size of the tumor in the subject and/or sample, a stage of the tumor in the subject, a tumor load in the subject and/or sample, and presence of tumor metastasis in the subject. In some embodiments, the classification is binary (e.g., positive or negative) or has more levels of classification (e.g., a scale from 1 to 10 or 0 to 1). In some embodiments, the terms "cutoff" and "threshold" refer to predetermined numbers used in an operation. In one example, a cutoff size refers to a size above which fragments are excluded. In some embodiments, a threshold value is a value above or below which a particular classification applies. Either of these terms can be used in either of these contexts.

As used herein, the term "cancer-associated changes" or "cancer-specific changes" can include cancer-derived mutations (including single nucleotide mutations, deletions or insertions of nucleotides, deletions of genetic or chromosomal segments, translocations, inversions), amplification of genes, virus-associated sequences (e.g., viral episomes, viral insertions, viral DNA that enters a cell (e.g., via viral infection) and is subsequently released by the cell, and circulating or cell-free viral DNA), aberrant methylation profiles or tumor-specific methylation signatures, aberrant cell-free nucleic acid (e.g., DNA) size profiles, aberrant histone modification marks and other epigenetic modifications, and locations of the ends of cell-free DNA fragments that are cancer-associated or cancer-specific.

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of a constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

Details of an exemplary system are now described in conjunction with FIG. 1. FIG. 1 is a block diagram illustrating system 100 in accordance with some implementations. System 100 in some implementations includes one or more processing units CPU(s) 102 (also referred to as processors or processing core), one or more network interfaces 104, user interface 106 comprising a display 108 and input module 110, non-persistent memory 111, persistent memory 112, and one or more communication buses 114 for interconnecting these components. One or more communication buses 114 optionally include circuitry (sometimes called a chipset) that interconnects and controls communications between system components. Non-persistent memory 111 typically includes high-speed random access memory, such as DRAM, SRAM, DDR RAM, ROM, EEPROM, flash memory, whereas persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid-state storage devices. Persistent memory 112 optionally includes one or more storage devices remotely located from the CPU(s) 102. Persistent memory 112, and the non-volatile memory device(s) within non-persistent memory 112, comprise non-transitory computer-readable storage medium. In some implementations, non-persistent memory 111 or alternatively non-transitory computer-readable storage medium stores the following programs, modules, and data structures, or a subset thereof, sometimes in conjunction with persistent memory 112:

optional instructions, programs, data, or information associated with optional operating system 116, which includes procedures for handling various basic system services and for performing hardware dependent tasks;

optional instructions, programs, data, or information associated with optional network communication module (or instructions) 118 for connecting the system 100 with other devices, or a communication network;

instructions, programs, data, or information associated with a plurality of datasets (e.g., datasets 1 and 2) 120-1 and 120-2, each dataset comprising:

instructions, programs, data, or information associated with a record 122 for each subject in a plurality of test subjects 122-1-1, . . . , 122-1-J (where J is a positive integer), each test subject comprising a plurality of fragment methylation patterns 124-1-1-1, . . . , 124-1-1-K (where K is a positive integer) from one or more nucleic acid samples in a respective biological sample obtained from the corresponding test subject, where each fragment methylation pattern is determined by methylation sequencing of the one or more nucleic acid samples and comprises a methylation state 126-1-1-1, ..., 126-1-1-1-L, (where L is a positive integer) for each CpG site in a corresponding plurality of CpG sites in the respective fragment;

instructions, programs, data, or information associated with one or more genomic regions 128-1-1, ..., 128-1-M (where M is a positive integer) for the respective dataset; and instructions, programs, data, or information associated with one or more state interval maps 130-1-1, 130-1-2, ..., 130-1-N(where N is a positive integer) for the one or more corresponding genomic regions using the respective dataset, where each state interval map comprises a corresponding independent plurality of nodes 132-1-1-1, ..., 132-1-1-P (where P is a positive integer), and each respective node in the plurality of nodes is characterized by a corresponding start methylation site 134-1-1-1-1, a corresponding end methylation site 136-1-1-1-1, and for each different fragment methylation pattern observed across the respective dataset between the corresponding start methylation site and the corresponding end methylation site of the respective node, a representation of the different fragment methylation pattern 138-1-1-1-1, ..., 138-1-1-1-Q (where Q is a positive integer) observed across the respective dataset and a count 140-1-1-1-1, ..., 140-1-1-1-R (where R is a positive integer) of fragments whose fragment methylation pattern begins at the corresponding start methylation site and ends at the corresponding end methylation site and has the different fragment methylation pattern.

In some implementations, one or more of the above-identified elements are stored in one or more of the previously mentioned memory devices, and correspond to a set of instructions for performing a function described above. The above-identified modules, data, or programs (e.g., sets of instructions) may not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above-identified elements is stored in a computer system, other than that of system 100, that is addressable by system 100 so that system 100 may retrieve all or a portion of such data.

Although FIG. 1 depicts a "system 100," the figure is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

Specific Embodiments of the Disclosure

While a system in accordance with the present disclosure has been disclosed with reference to FIG. 1, methods in accordance with the present disclosure are now detailed with reference to FIG. 2. Any of the disclosed methods can make use of any of the assays or algorithms disclosed in U.S. patent application Ser. No. 15/793,830, filed Oct. 25, 2017, International Patent Publication No. WO 2018/081130, entitled "Methods and Systems for Tumor Detection," and/or United States Patent Publication No. 2020-0385813 A1, entitled "Systems and Methods for Estimating Cell Source Fractions Using Methylation Information," each of which is hereby incorporated herein by reference in its entirety, in order to determine a cancer condition in a test subject or a likelihood that the subject has the cancer condition. For instance, any of the disclosed methods can work in conjunction with any of the disclosed methods or algorithms disclosed in U.S. patent application Ser. No. 15/793,830, filed Oct. 25, 2017, International Patent Publication No. WO 2018/081130, United States Patent Publication No. 2020-0385813 A1, and/or U.S. Provisional Patent Application No. 62/781,549, entitled "Systems and Methods for Estimating Cell Source Fractions Using Methylation Information," filed Dec. 18, 2018.

Referring to FIG. 2, one aspect of the present disclosure provides a method of identifying a plurality of methylation patterns that discriminate or indicate a cancer condition (block 202).

Obtaining Datasets.

Referring to block 204 of FIG. 2A, the present disclosure provides systems, methods, and computer readable media for identifying a plurality of qualifying methylation patterns that discriminate or indicate a cancer condition. In such embodiments, a first dataset is obtained (e.g., in electronic form). The first dataset comprises a corresponding fragment methylation pattern of each respective fragment in a first plurality of fragments. In some embodiments, the corresponding fragment methylation pattern of each respective fragment (i) is determined by methylation sequencing of nucleic acids from a respective biological sample obtained from a corresponding subject in a first set of one or more subjects and (ii) comprises a methylation state of each CpG site in a corresponding plurality of CpG sites in the respective fragment. In some embodiments, the first plurality of fragments comprises 100 or more cell-free nucleic acid fragments, 1000 or more cell-free nucleic acid fragments, 10,000 or more cell-free nucleic acid fragments, 100,000 or more cell-free nucleic acid fragments, 1,000,000 or more cell-free nucleic acid fragments, or 10,000,000 or more nucleic acid fragments.

The number of subjects in the first set of one or more subjects is application dependent. For example, if the cancer condition is tissue of origin (e.g., identifying qualifying methylation patterns that aid in discriminating the origin of a cancer condition), the number of subjects in the first set of one or more subjects is typically a plurality of cancer subjects that have a particular origin of cancer (e.g., they all have lung cancer, they all have liver cancer, etc.). In some such embodiments, the plurality of cancer subjects is 5 or more subjects, 10 or more subjects, 20 or more subjects, 30 or more subjects, 40 or more subjects, 50 or more subjects, 100 or more subjects, 200 or more subjects, 500 or more subjects, 1000 or more subjects, between 10 and 10,000 subjects, or fewer than 25,000 subjects that that have a particular origin of cancer. In some such embodiments, the plurality of subjects all have the same stage of cancer. In alternative embodiments, the plurality of subjects have varying stages of the cancer. In some embodiments, the plurality of subjects have cancer that has metastasized. In some embodiments, the plurality of subjects have cancer that has not metastasized.

As another example, if the cancer condition is absence or presence of cancer (e.g., identifying qualifying methylation patterns that aid in determining the absence or presence of a cancer condition), again the number of subjects in the first set of one or more subjects is typically a plurality of cancer subjects that have cancer (e.g., they all have cancer, they all have a particular cancer under study, etc.). In some such embodiments, the plurality of cancer subjects is 5 or more subjects, 10 or more subjects, 20 or more subjects, 30 or more subjects, 40 or more subjects, 50 or more subjects, 100 or more subjects, 200 or more subjects, 500 or more subjects, 1000 or more subjects, between 10 and 10,000 subjects, or fewer than 25,000 subjects. In some such embodiments, the plurality of subjects all have the same stage of cancer. In alternative embodiments, the plurality of subjects have varying stages of the cancer. In some embodiments, the plurality of subjects have cancer that has metastasized. In some embodiments, the plurality of subjects have cancer that has not metastasized.

As still another example, if the cancer condition is stage of a particular cancer (e.g., identifying qualifying methylation patterns that aid in determining whether a subject has a particular stage of a particular cancer condition), yet again the number of subjects in the first set of one or more subjects is typically a plurality of cancer subjects that have the stage of the cancer condition (e.g., they all have stage II breast cancer, etc.).

On the other hand, if there is an expectation that the cancer condition generates fragment methylation patterns that are private (unique) to a particular subject's cancer condition, then the number of subjects in the first set of one or more subjects is a single subject. A nonlimiting example where an expectation that the cancer condition generates fragment methylation patterns that are private (unique) to a particular subject's cancer condition is the case where the cancer condition is tumor fraction. Another nonlimiting example where an expectation that the cancer condition generates fragment methylation patterns that are private (unique) to a particular subject's cancer condition is the case where the cancer condition is affected by the hematopoietic status of a particular subject. In instances where there is an expectation that the cancer condition generates fragment methylation patterns that are private (unique) to a particular subject's cancer condition, the first set of one or more subjects is a single subject under study and a second set of one or more subjects, discussed in further detail below, is a reference population, such as a cohort of healthy subjects.

In some embodiments, the first set of subjects is a single subject and the second set of subjects is a plurality of subjects, and the QMPs that are identified using the disclosed methods are used to inspect or evaluate a downstream cancer condition classifier. For instance, a subject that is afflicted with a cancer could constitute the first set of subjects, the second set of subjects can be subjects that do not have a cancer condition, and the contribution of the QMPs identified using the disclosed methods can be inspected in a downstream classifier. For example, the classifier can be rebuilt (retrained) to include or not include some or all of the identified QMPs and its performance evaluated using a training cohort of subjects that have and do not have the cancer condition.

Test Subjects.

In some embodiments, each subject under study is any of the examples of subjects as defined above (see, Definitions). In some embodiments, a subject is a human. In some embodiments, subjects the second set of subjects is a study group, and the first set of one or more subjects is a single test subject that is also a participant in a plurality of participants in the study group. For example, in some embodiments, the second set of subjects is plurality of subjects that are each participants from a CCGA study (see, e.g., Example 1 below).

Biological Samples.

In some embodiments, the biological samples used in the present disclosure are any of the examples of biological samples as defined above (See, Definitions). For example, in some embodiments, the biological sample is a tissue (e.g., a tumor biopsy). Referring to blocks 206-210 of FIG. 2A, in some embodiments, the biological sample obtained from a subject (e.g., a test subject) is a liquid biological sample. For example, in some embodiments, the respective biological sample is a blood sample (e.g., plasma, cell-free DNA, and/or white blood cells). In some embodiments, the respective biological sample comprises blood, whole blood, plasma, serum, urine, cerebrospinal fluid, fecal, saliva, sweat, tears, pleural fluid, pericardial fluid, or peritoneal fluid. In some embodiments, the biological sample is derived from a cell source. In some such embodiments, the cell source is any one of the example cell sources described in detail in the Examples (see, e.g., Example 7 below).

In some embodiments, the biological sample is obtained from a subject (e.g., a test subject) having cancer or from a healthy (e.g., non-cancer) subject. In some embodiments, the biological sample is obtained from tumor tissue (e.g., cancer) or from healthy tissue (e.g., non-cancer). In some embodiments, the biological sample is obtained from an archived sample (e.g., a frozen, desiccated, or alternatively stored tissue biopsy or blood sample).

Figure 7:
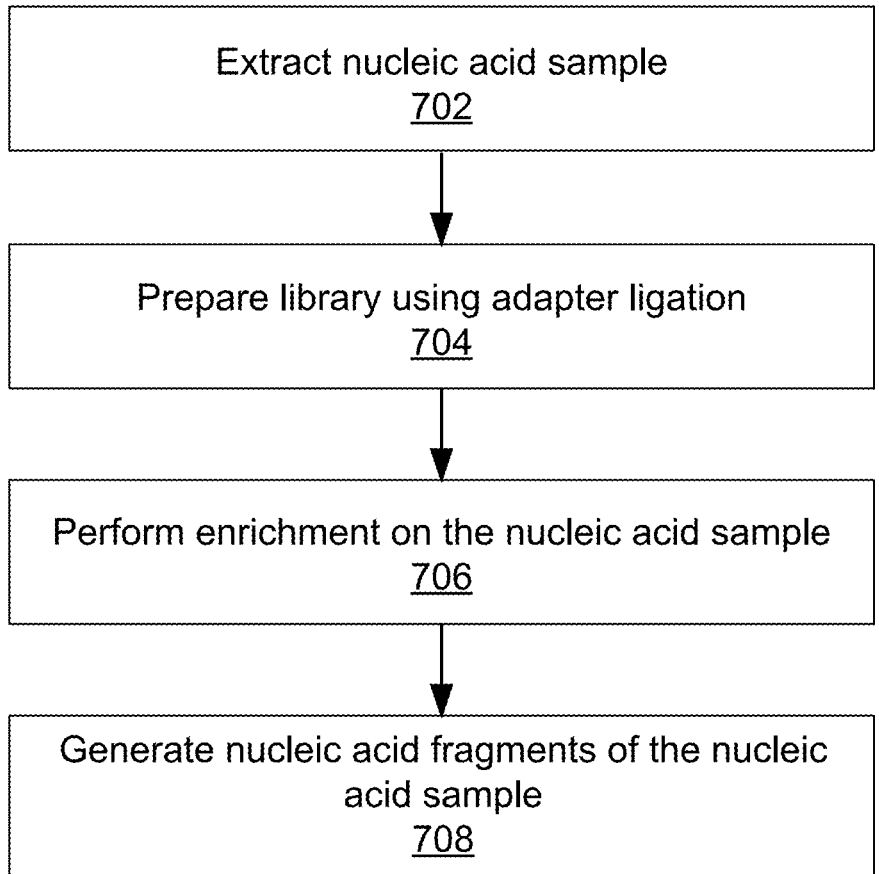
FIG. 7 illustrates a flowchart of a method for preparing a nucleic acid sample for sequencing in accordance with some embodiments of the present disclosure.

In some embodiments, the biological sample is a plurality of biological samples (e.g., a pooled sample comprising a plurality of samples). A plurality of biological samples can be pooled at any point prior to obtaining the first dataset. For example, in some embodiments, pooling the plurality of biological samples occurs prior to nucleic acid extraction (e.g., pooling a plurality of tissue and/or liquid biological samples), after nucleic acid extraction but before methylation sequencing (e.g., pooling a plurality of nucleic acid samples), or after methylation sequencing (e.g., pooling sequencing data from a plurality of sequencing assays). FIGS. 7 and 9 illustrate example flowcharts of methods for preparing nucleic acid samples for sequencing and for obtaining methylation sequencing data from biological samples, in accordance with some embodiments of the present disclosure (see, e.g., Examples 2 and 3 below).

Data Obtained from Methylation Sequencing.

In some embodiments, a dataset 120 can be of any size and comprise any number of corresponding fragment methylation patterns 124 for each respective fragment in the plurality of fragments and/or any number of fragments in the plurality of fragments, depending on the method, coverage, and depth of methylation sequencing used. For example, referring to block 212, in some embodiments, the methylation sequencing of a respective biological sample from a corresponding subject in the first set of subjects (where the first set of subjects consists of a single subject or comprises a plurality of subject) produces 500 million or more, one billion or more, two billion or more, three billion or more, four billion or more, five billion or more, six billion or more, seven billion or more, eight billion or more, nine billion or more, or 10 billion or more nucleic acid fragments that are evaluated for methylation patterns by inclusion in the first dataset. In some alternative embodiments, the methylation sequencing of a respective biological sample from the corresponding subject in the first set of subjects produces less than one billion fragments or less than 10,000 fragments that are evaluated for methylation patterns by inclusion in the first dataset (dataset 120).

In some embodiments, a corresponding fragment methylation pattern of a respective fragment is determined by a methylation sequencing, where the methylation sequencing produces one or more sequence reads corresponding to the respective fragment. In some embodiments, the plurality of fragments are cell-free nucleic acids. In some embodiments, the one or more sequence reads corresponding to a respective fragment are paired-end sequence reads. In some embodiments, the one or more sequence reads corresponding to a respective fragment are single-end sequence reads.

Referring to block 214 of FIG. 2A, in some embodiments, an average sequence read length of a corresponding plurality of sequence reads obtained by the methylation sequencing is between 140 and 280 nucleotides.

Referring to block 216, in some embodiments, the methylation sequencing is i) whole-genome methylation sequencing or ii) targeted DNA methylation sequencing using a plurality of nucleic acid probes. In some embodiments, the methylation sequencing is whole-genome bisulfite sequencing (WGBS).

Referring to blocks 218-224, in some embodiments, the methylation sequencing detects one or more 5-methylcytosine (5 mC) and/or 5-hydroxymethylcytosine (5 hmC) in respective fragments. In some embodiments, the methylation sequencing comprises conversion of one or more unmethylated cytosines or one or more methylated cytosines to a corresponding one or more uracils. In some such embodiments, the one or more uracils are detected during the methylation sequencing as one or more corresponding thymines. In some such embodiments, the conversion of one or more unmethylated cytosines or one or more methylated cytosines comprises a chemical conversion, an enzymatic conversion, or combinations thereof.

Referring to block 226 of FIG. 2A, in some embodiments the methylation state of a CpG site in the corresponding plurality of CpG sites is methylated when the CpG site is determined by the methylation sequencing to be methylated, and unmethylated when the CpG site is determined by the methylation sequencing to not be methylated. In some embodiments, a methylated state is represented as "M", and an unmethylated state is represented as "U". For example, in some embodiments, the methylation state can include but is not limited to: unmethylated, methylated, ambiguous (e.g., meaning the underlying CpG is not covered by any reads in the pair of sequence reads), variant (e.g., meaning that the read is not consistent with a CpG occurring in its expected position based on the reference sequence and can be caused by a real variant at the site or a sequence error), or conflict (e.g., when the two reads both overlap a CpG but are not consistent). See, e.g., U.S. patent application Ser. No. 17/119,606, entitled "Cancer classification using patch convolutional neural networks," filed Dec. 11, 2020, which is hereby incorporated herein by reference in its entirety.

In some embodiments, the methylation sequencing (e.g., WGBS) produces a coverage (e.g., sequencing depth) of at least 1×, 2×, 3×, 4×, 5×, 6×, 7×, 8×, 9×, 10×, at least 20×, at least 30×, or at least 40× across all or a portion of the genome of the test subject.

In some embodiments, the methylation sequencing (e.g., WGBS) produces an average coverage (e.g., sequencing depth) of at least 1×, 2×, 3×, 4×, 5×, 6×, 7×, 8×, 9×, 10×, at least 20×, at least 30×, or at least 40× across the plurality of fragments. In some embodiments, the methylation sequencing (e.g., WGBS) produces an average coverage (e.g., sequencing depth) of at least 1×, 2×, 3×, 4×, 5×, 6×, 7×, 8×, 9×, 10×, at least 20×, at least 30×, or at least 40× across the fragments represented in the dataset 120.

In some embodiments, the methylation sequencing (e.g., targeted methylation or TM sequencing) has a coverage including but not limited to up to 1,000×, 2,000×, 3,000×, 5,000, 10,000×, 15,000×, 20,000×, or about 30,000×.

In some embodiments, the methylation sequencing (e.g., targeted methylation or TM sequencing) has an average coverage including but not limited to up to 1,000×, 2,000×, 3,000×, 5,000, 10,000×, 15,000×, 20,000×, or about 30,000× across the plurality of fragments.

In some embodiments, the methylation sequencing (e.g., WGBS) produces an average coverage (e.g., sequencing depth) of up to 1,000×, 2,000×, 3,000×, 5,000, 10,000×, 15,000×, 20,000×, or about 30,000× across the fragments represented in the dataset 120.

In some embodiments, the methylation sequencing has a coverage that is greater than 30,000×, e.g., at least 40,000× or 50,000×. See, Ziller et al., 2015, "Coverage recommendations for methylation analysis by whole-genome bisulfite sequencing," Nature Methods. 12 (3): 230-232, doi: 10.1038/nmeth.3152, and Masser et al., 2015, "Targeted DNA Methylation Analysis by Next-generation Sequencing," J. Vis. Exp. (96), e52488, doi: 10.3791/52488, which are hereby incorporated herein by reference in their entirety.

In some embodiments, the methylation sequencing is paired-end sequencing or single-end sequencing.

In some embodiments, the methylation sequencing is binary. In some embodiments, the methylation sequencing is semi-binary. As used herein, binary methylation sequencing refers to sequencing CpG sites that are fully methylated and/or fully unmethylated using hybridization probes that are specific to both methylated and unmethylated sites. Alternatively, as used herein, semi-binary methylation sequencing refers to sequencing CpG sites that are either methylated or unmethylated, using hybridization probes specific to either methylated or unmethylated sites.

Methylation sequencing performed using binary probes can provide improved depth of coverage and reduce bias in methylation sequencing datasets. Thus, in some embodiments, WGBS is performed using binary probes. In some alternative embodiments, targeted methylation (TM) sequencing is performed using binary and/or semi-binary probes. In some such embodiments, the overall depth of coverage is improved by removing (e.g., filtering) from the dataset the corresponding fragment methylation patterns of any fragments that are targeted by semi-binary probes (e.g., the sequencing reads corresponding to fragments sequenced using semi-binary probes are filtered). Alternatively, in some embodiments, the one or more fragments that are sequenced using semi-binary probes are not removed from the dataset, and a depth cutoff is applied to the first dataset such that the corresponding fragment methylation patterns of any fragments overlapping a region (e.g., of a reference genome) having a sequencing depth below a depth cutoff are removed from the dataset. For example, where binary sequencing provides a higher depth of coverage and semi-binary sequencing provides a lower depth of coverage, applying the depth cutoff efficiently ensures that any remaining regions in the dataset comprise at least a minimum depth of coverage thereby reducing overall bias in the dataset. In some embodiments, the depth cutoff is an estimate of the minimum coverage depth provided by binary sequencing and/or an estimate of the maximum coverage depth provided by semi-binary sequencing.

In some embodiments, the methylation sequencing (e.g., WGBS and/or TM sequencing) is performed using tissue (e.g., a tumor biopsy) or a blood sample (e.g., plasma, cell-free DNA, and/or white blood cells).

In some embodiments, the plurality of fragment methylation patterns for the plurality of fragments is determined by a plurality of methylation sequencings of nucleic acids from a respective biological sample obtained from a corresponding subject in a set of subjects. For example, in some such embodiments, a plurality of fragment methylation patterns is obtained from a respective biological sample using both WGBS and targeted DNA methylation sequencing.

In some embodiments, the method further comprises obtaining a dataset comprising sequencing data for each respective fragment in the plurality of fragments, where the sequencing data is determined by one or more sequencing assays (e.g., WGS, targeted sequencing) of nucleic acids from the respective biological sample obtained from the corresponding subject. For example, in some such embodiments, one or more fragment methylation patterns and one or more sequencing datasets are obtained from a respective biological sample using, e.g., WGBS, targeted methylation (TM) sequencing, WGS, targeted sequencing, and/or any combination thereof. Comparisons of multiple sequencing and/or methylation sequencing datasets are described below in Example 5 and FIG. 11.

For further details regarding methylation sequencing (e.g., WGBS and/or targeted methylation sequencing), see, e.g., United States Patent Publication No. US 2019-0287652 A1, entitled "Methylation Fragment Anomaly Detection," filed Mar. 13, 2019, and United States Patent Publication No. 2020-0385813 A1, entitled "Systems and Methods for Estimating Cell Source Fractions Using Methylation Information," each of which is hereby incorporated by reference. Other methods for methylation sequencing, including those disclosed herein and/or any modifications, substitutions, or combinations thereof, can be used to obtain fragment methylation patterns, as will be apparent to one skilled in the art. Fragments.

In some embodiments, each respective fragment in the plurality of fragments comprises a start position, an end position, and one or more methylation sites (e.g., CpG sites) located within the respective fragment between the start and the end position, as determined by any of the methylation sequencing methods disclosed herein. In some embodiments, the start and/or end position is a methylation site or a position in a reference genome. In some embodiments, each respective fragment in the plurality of fragments is aligned to a reference genome. Thus, in some such embodiments, each methylation site in each respective fragment in the plurality of fragments is indexed to a specific site in the reference genome. Similarly, where a respective fragment in the plurality of fragments comprises a start and/or end position that is a methylation site, and/or one or more methylation sites located within the respective fragment between the start and end position, each methylation site in the respective fragment can be indexed to a specific site in a reference genome.

In some embodiments, unique fragments are determined by the respective start and end positions and/or the sequence of methylation states of the one or more methylation sites of the respective fragment (e.g., the fragment methylation pattern). For example, in some embodiments, two fragments with different start and end positions are considered unique, regardless of whether the fragment methylation pattern is the same or different. In some embodiments, two fragments can be considered unique even if one of the start or end positions is shared between the two fragments (e.g., two fragments having the same start position but different end positions, such that the two fragments are of different lengths). In some alternative embodiments, two fragments with the same start and end positions, but with different fragment methylation patterns, are considered unique (e.g., two fragments aligned to the same region of a reference genome but having different methylation states for one or more CpG sites within the span of CpG sites, such as "MMMMM" and "UMMMM").

In some embodiments, the corresponding fragment methylation pattern of each respective fragment comprises a methylation state of less than all of the CpG sites in the corresponding plurality of CpG sites in the respective fragment, where one or more CpG sites in a respective one or more fragments is considered to be "unreliable." For example, in some embodiments, "unreliable" CpG sites comprise CpG sites having variant, ambiguous, or conflicted methylation states, and/or CpG sites known to result in poor methylation sequencing output. In some such embodiments, the respective one or more unreliable CpG sites are removed (e.g., deleted) from the plurality of fragments for all subsequent analyses and processes. For example, in some embodiments, the deletion is performed by removing the respective one or more CpG sites (as represented by a respective one or more methylation states of the respective one or more CpG sites) from the corresponding fragment methylation pattern of each respective fragment in the respective plurality of fragments in the respective dataset. In some alternative embodiments, the respective one or more unreliable CpG sites are not removed from the plurality of fragments, but are otherwise bypassed for all subsequent analyses and processes. For example, in some embodiments, the bypassing is performed, for each respective unreliable CpG site, by inserting a placeholder or substitute representation in place of the methylation state representation at the respective CpG site in the corresponding fragment methylation pattern of each respective fragment in the respective plurality of fragments in the respective dataset. In some embodiments, a placeholder or substitute representation is, e.g., a wildcard or null character.

In some embodiments, the plurality of fragments is filtered. In some embodiments, the plurality of fragments is filtered for, e.g., depth, minimum mapping quality (MAPQ), duplicate fragments, uncalled fragments, unconverted fragments, ambiguous calls, variant calls, conflicted calls, and/or p-value.

In some embodiments, the plurality of fragments is filtered for fragments comprising overlapping CpG sites. In some embodiments, the plurality of fragments is filtered for fragments that share read support with alternative sequencing methods. For example, in some embodiments where one or more methylation sequencing datasets and one or more sequencing datasets are obtained from a respective biological sample using, e.g., WGBS, TM sequencing, WGS, and/or targeted sequencing, the respective datasets are compared and the one or more methylation sequencing datasets are filtered to remove fragments that do not also include small variants, known biomarkers, and/or regions associated with a cancer condition as determined using the one or more sequencing datasets.

First and Second Datasets.

Figure 2B:
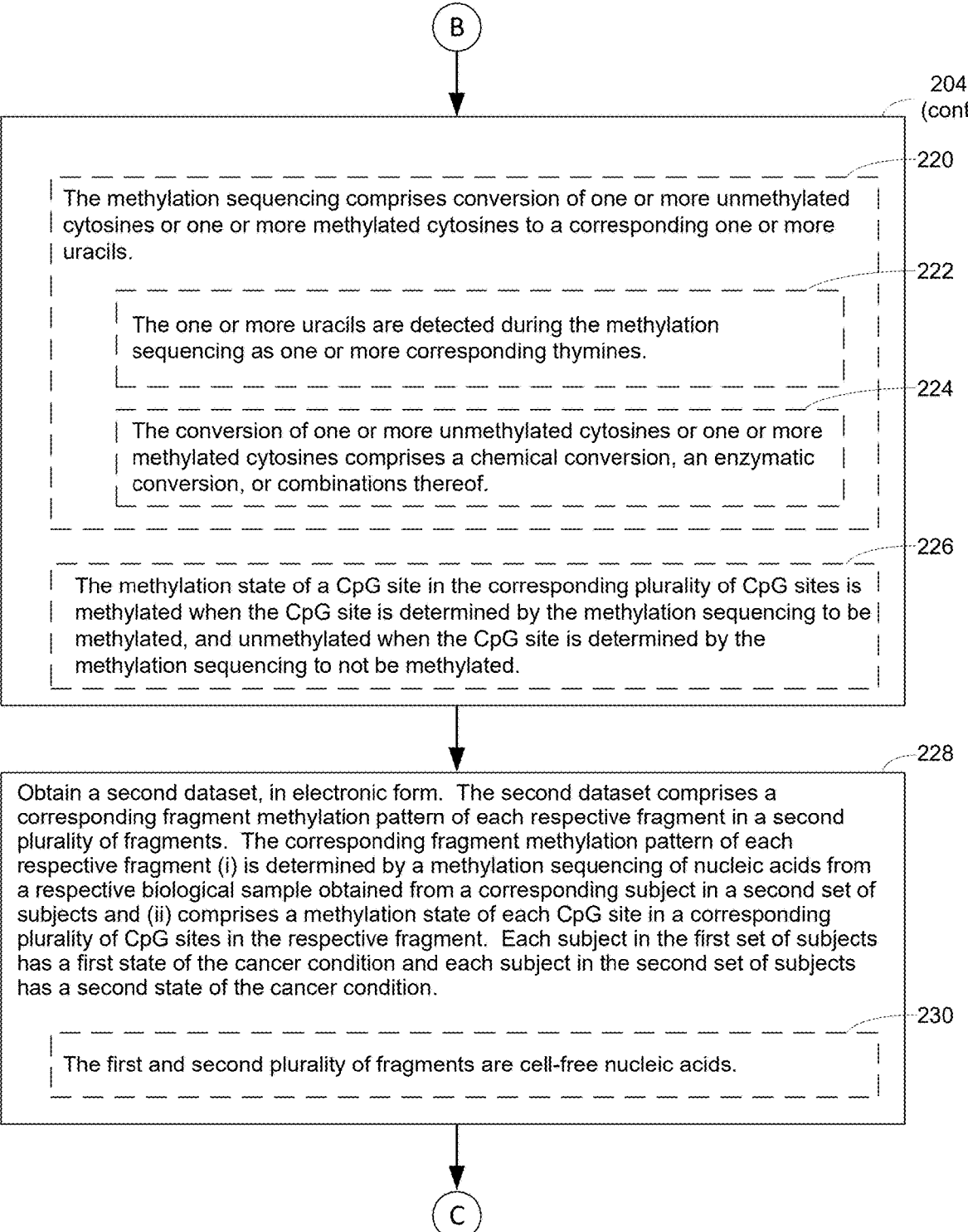

Referring to block 228 of FIG. 2B, in some embodiments a second dataset is obtained in electronic form. The second dataset comprises a corresponding fragment methylation pattern of each respective fragment in a second plurality of fragments. The corresponding fragment methylation pattern of each respective fragment (i) is determined by methylation sequencing of nucleic acids from a respective biological sample obtained from a corresponding subject in a second set of subjects and (ii) comprises a methylation state of each CpG site in a corresponding plurality of CpG sites in the respective fragment. In typical embodiments, the second set of subjects comprises a plurality of subjects (e.g., 2 or more subjects, 3 or more subjects, 5 or more subject, 50 or more subjects, 100 or more subjects, 500 or more subjects or 1000 or more subjects). In some embodiments, the second plurality of fragments comprises 100 or more cell-free nucleic acid fragments, 1000 or more cell-free nucleic acid fragments, 10,000 or more cell-free nucleic acid fragments, 100,000 or more cell-free nucleic acid fragments, 1,000,000 or more cell-free nucleic acid fragments, or 10,000,000 or more nucleic acid fragments.

In some embodiments, the second dataset is obtained using any of the methods disclosed herein (e.g., using any of the methods and/or embodiments described for the first dataset). Referring to block 230 of FIG. 2B, in some embodiments, the first plurality of fragments (of the first data set) and the second plurality of fragments (of the second data set) are cell-free nucleic acids.

Referring again to block 228 of FIG. 2B, in some embodiments each subject in the first set of subjects (of the first dataset) has a first state of the cancer condition and each subject in the second set of subjects (of the second dataset) has a second state of the cancer condition. As defined above, in various embodiments, a state of a cancer condition is application dependent. In some embodiments a state of a cancer condition is whether or not a cancer exists (e.g., presence or absence) in a subject. In some embodiments, a state of a cancer condition is a stage of a cancer, a size of tumor, presence or absence of metastasis, the total tumor burden (e.g., tumor fraction) of the body, and/or another measure of a severity of a cancer (e.g., recurrence of cancer). In some embodiments, a first state of the cancer condition is a sample condition (e.g., a cancerous sample), and a second state of the cancer condition is a reference sample (e.g., a healthy sample). In some embodiments, a first state of the cancer condition and a second state of the cancer condition are an early time point and a later time point, respectively, at which a biological sample was collected. In some embodiments, a cancer condition is tumor fraction of a test subject (e.g., a subject in the first set of one or more subjects. In some embodiments, a cancer condition is cancer origin (e.g., lung, colorectal, breast, etc.).

Generating State Interval Maps.

Referring to block 232 of FIG. 2C, in some embodiments one or more first state interval maps are generated for one or more corresponding genomic regions using the first dataset. Each first state interval map in the one or more first state interval maps comprises a corresponding independent plurality of nodes. In some embodiments, there is only one state interval map for the first set of subjects and this state interval map represents the entirety of the regions of the genome under study (e.g., all or a portion of the genome). In other embodiments, there are several state interval maps for the first set of one or more subjects. In such an instance, typically, each respective state interval map represents a different region of the genome. For instance, in some embodiments, each state interval map represents a different chromosome. In some embodiments, two, three, four, five, six, seven, eight, nine, ten, between 2 and 30, or more than 30 state interval maps are generated using the methylation data in the first dataset. In typical embodiments, each such state interval map represents a different portion of a reference genome. For instance, in some embodiments, each such state interval map represents a different chromosome.

Regardless of whether there is only a single state interval map or several state interval maps generated, each respective node in each corresponding independent plurality of nodes in the one or more first state interval maps is characterized by a corresponding start methylation site, a corresponding end methylation site, and for each different fragment methylation pattern observed across the first plurality of fragments in the first dataset between the corresponding start methylation site and the corresponding end methylation site of the respective node, (i) a representation of the different fragment methylation pattern and (ii) a count of fragments in the first dataset whose fragment methylation pattern begins at the corresponding start methylation site and ends at the corresponding end methylation site and has the different fragment methylation pattern.

Genomic Regions Represented by Interval Maps.

In some embodiments, each respective interval map in the one or more first state interval maps corresponds to a genomic region (e.g., in a reference genome). Thus, for a respective interval map corresponding to a respective genomic region, each respective fragment in the first plurality of fragments in the first dataset having a fragment methylation pattern that is represented in the respective interval map also corresponds to the same respective genomic region (e.g., the fragments are aligned to the same region of the reference genome corresponding to the interval map).

In some embodiments, one or more first state interval maps correspond to one or more unique genomic regions and/or one or more overlapping genomic regions. In some embodiments, one or more first state interval maps correspond to the same genomic region. In some embodiments, the one or more first state interval maps is a plurality of first state interval maps, the one or more corresponding genomic regions is a plurality of genomic regions, and each respective genomic region in the plurality of genomic regions is represented by a first state interval map in the plurality of first state interval maps. In some embodiments, the plurality of genomic regions is between 10 and 30. In some such embodiments, the plurality of genomic regions consists of between two and 1000 genomic regions, between 500 and 5,000 genomic regions, between 1,000 and 20,000 genomic regions or between 5,000 and 50,000 genomic regions.

In some embodiments, one or more first state interval maps correspond to genomic regions of the same size or different sizes, numbers or amounts (for instance represented as, e.g., a length that is a number of CpG sites and/or a number of base pairs). For example, referring to blocks 234-238, in some embodiments, there are more than 10,000 CpG sites, more than 25,000 CpG sites, more than 50,000 CpG sites, or more than 80,000 CpG sites across the one or more corresponding genomic regions. In some alternative embodiments, there are less than 10,000 CpG sites, less than 25,000 CpG sites, less than 50,000 CpG sites, or less than 80,000 CpG sites across the one or more corresponding genomic regions. In some embodiments, each genomic region in the one or more corresponding genomic regions represents between 500 base pairs and 10,000 base pairs of a human genome reference sequence. In some embodiments, an interval map represents all the known CpG sites in a predetermined region of a reference genome. In some embodiments, an interval map represents only a subset of the known CpG sites in a predetermined region of a reference genome. In some embodiments, each genomic region in the one or more corresponding genomic regions for a particular interval map represents between 500 base pairs and 2,000 base pairs of a human genome reference sequence. In some alternative embodiments, each genomic region in the one or more corresponding genomic regions for a particular interval map represents less than 500 base pairs or more than 10,000 base pairs of a human genome reference sequence.

Referring to block 240 of FIG. 2C, in some embodiments, each genomic region in the one or more corresponding genomic regions for a particular interval map represents a different portion of a human genome reference sequence. For example, in some such embodiments, each genomic region in the one or more corresponding genomic regions for a particular interval map is a different human chromosome. In some embodiments, each portion of a human genome reference sequence is represented by a respective one or more interval maps.

Node Construction.

As described above, each first state interval map in the one or more first state interval maps comprises an independent plurality of nodes. Each respective node is characterized by a corresponding start methylation site, a corresponding end methylation site, and representation and count of each different fragment methylation pattern in the plurality of fragments in the first dataset that start and end at the respective start and end methylation sites of the respective node. In some embodiments, the independent plurality of nodes comprises 2 or more nodes, 3 or more nodes, 4 or more nodes, 5 or more nodes, 10 or more nodes, 20 or more nodes, 50 or more nodes, or 100 or more nodes.

In some embodiments, the specific start and end methylation sites of each respective node in the independent plurality of nodes are indexed to a position in a reference genome (e.g., a location in a genomic region and/or a CpG site). Thus, in some preferred embodiments, a respective node in a respective first state interval map is constructed by grouping one or more fragments in the plurality of fragments in the first dataset, based on the start and end methylation sites of the respective one or more fragments (e.g., where fragments are aligned to a reference genome and each respective fragment comprises start and end methylation sites that are indexed to a position in a reference genome), such that each fragment included in a respective node is wholly contained within the node.

In some preferred embodiments, a fragment that does not comprise start and end methylation sites corresponding to the start and end methylation sites of a respective node (e.g., a fragment that is partially contained within or that overlaps the respective node, and/or a fragment that is smaller or larger than the respective node) is not represented in the respective node.

In such implementations as described herein, therefore, fragments are converted to fragment-level nodes comprising sequences of CpG sites, identified by, e.g., their genomic coordinates or position in an index of CpG sites.

In some embodiments, fragments that are considered "unique" (e.g., having different start and end methylation sites and/or different methylation patterns) are placed into different respective nodes.

In some embodiments, the status of each CpG site (e.g., methylated: "M", unmethylated: "U") in each fragment in a respective node is additionally represented by one or more different fragment methylation patterns included in the respective node. In some preferred implementations, each different fragment methylation pattern represented in each respective node corresponds to the entire fragment methylation pattern of a respective one or more fragments in the node (e.g., where each fragment begins and ends at the start and end positions of the node, the corresponding fragment methylation pattern is wholly contained in the node).

In some embodiments, a node is constructed by grouping one or more fragments based on the fragment methylation pattern of the respective fragments in the respective node.

In some embodiments, a node is constructed by grouping one or more fragments that have identical fragment methylation patterns between and/or including the corresponding start methylation site and the corresponding end methylation site of the respective node. For example, in some embodiments, a first set of fragments, each comprising a first start methylation site and a first end methylation site corresponding to a specific start and end position in a reference genome, is grouped into a first node. In some such embodiments, a second plurality of fragments, comprising a second start methylation site and a second end methylation site that correspond to the same positions in the reference genome as the first start methylation site and first end methylation site, respectively, is nonetheless grouped into a second node, if the fragment methylation patterns of the second plurality of fragments differ from the fragment methylation patterns of the first plurality of fragments at one or more CpG sites in the sequence of CpG sites. Thus, in some such embodiments, only fragments that start and end at the start methylation site and the end methylation site of the respective node, and that comprise a specific fragment methylation pattern, are populated into a node.

In some embodiments, a node is constructed by grouping one or more fragments that have different fragment methylation patterns between and/or including the corresponding start methylation site and the corresponding end methylation site of the respective node. In some such embodiments, a node is constructed by grouping one or more fragments that differ by 1, 2, 3, 4, 5, 6, 7, 8, 9, 10, or more than 10 CpG site states (e.g., that have different methylation states at one or more CpG sites). In some such embodiments, a node is constructed by grouping one or more fragments where the respective one or more fragment methylation patterns differ by 10%, 20%, 30%, 40%, 50%, 60%, 70%, 80%, 90%, or 100%.

In some embodiments, a node is constructed by grouping one or more fragments that have differing CpG states at one or more CpG sites, where the respective one or more CpG sites are located at positions that do not correspond across the respective one or more fragments. In some alternative embodiments, a node is constructed by grouping one or more fragments whose CpG states differ at one or more CpG sites, where the respective one or more CpG sites are located at corresponding positions across the respective one or more fragments. For example, in some such embodiments, one or more fragments can be included in a node regardless of the methylation state at, e.g., the first CpG site, whereas the methylation states at all remaining CpG sites must be identical. In some such embodiments, a CpG site that is allowed to differ across all fragments is represented by a placeholder or substitute representation in the interval map (e.g., a wildcard or null character).

In some embodiments, the independent plurality of nodes for a respective first state interval map also corresponds to the respective corresponding genomic region of the respective first state interval map. In some such embodiments, a respective independent plurality of nodes for a respective first state interval map is unique (e.g., independent) from any other independent plurality of nodes for any other first state interval map, as determined by the characteristics (e.g., start and end methylation site and/or represented fragment methylation patterns) of the respective independent plurality of nodes.

In some embodiments, a node represents a corresponding genomic region or sub-region that comprises one or more CpG sites. In some embodiments, a node represents a corresponding genomic region or sub-region that comprises 3, 4, 5, 6, 7, 8, 9, 10, 11, 12, 13, 14, 15, 16, 17, 18, 19, 20 or more than 20 CpG sites. In some embodiments, a node represents a corresponding genomic region or sub-region that comprises 3, 4, 5, 6, 7, 8, 9, 10, 11, 12, 13, 14, 15, 16, 17, 18, 19, 20 or more than 20 contiguous CpG sites. In some embodiments, a node represents a corresponding genomic region or sub-region that comprises between 2 and 100 contiguous CpG sites in a human reference genome.

Figure 12:
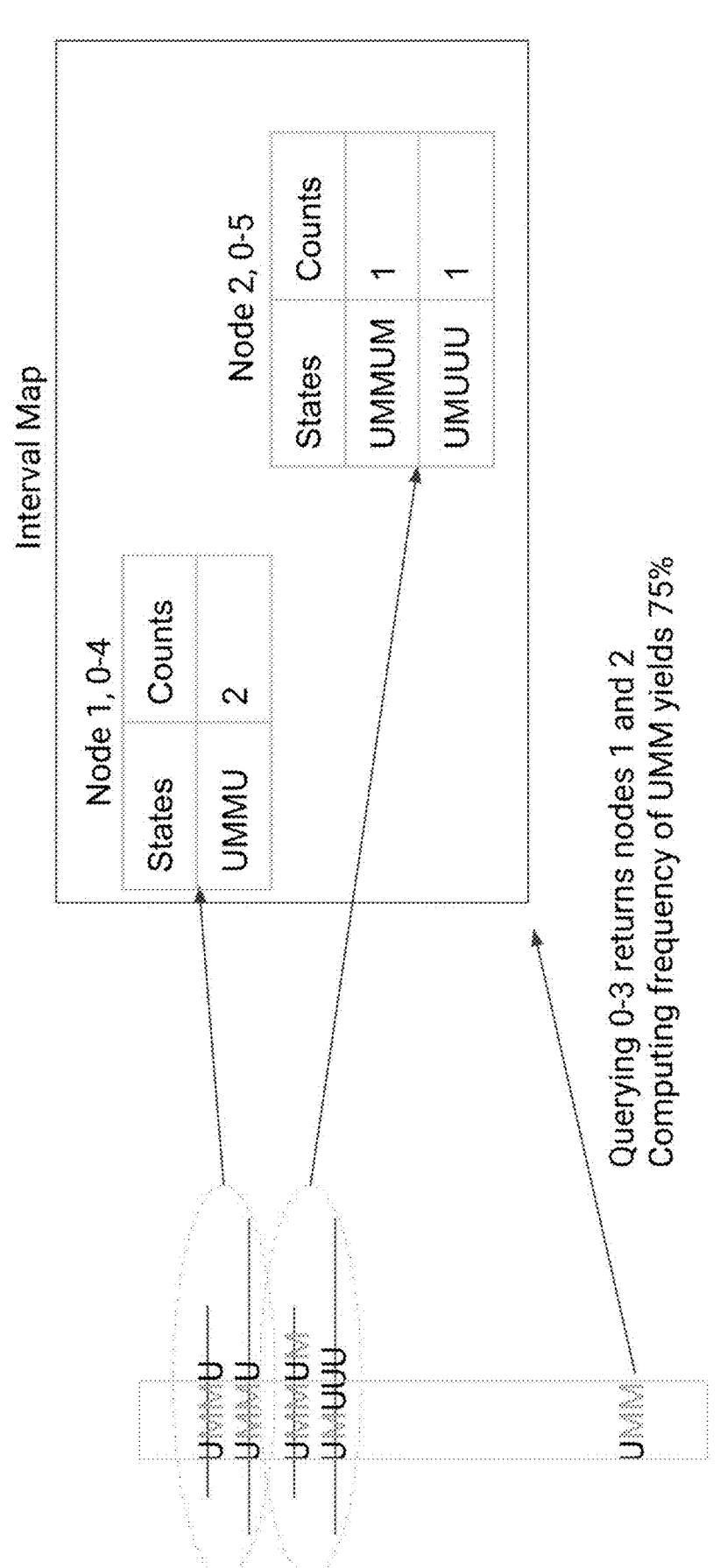
FIG. 12 illustrates an example method for generating interval maps, in accordance with some embodiments of the present disclosure.

FIG. 12 illustrates a respective interval map comprising two example nodes in accordance with some embodiments of the present disclosure. In FIG. 12, four independent fragments are organized into two nodes. Each node comprises a start methylation site and an end methylation site (e.g., Node 1: positions 0-4, Node 2: positions 0-5) and a representation of each methylation pattern observed in the dataset between the start and end positions for the respective fragments (e.g., Node 1: UMMU, UMMU; Node 2: UMMUM, UMUUU). In this example, the positions denoting the start and end methylation sites are represented as an interval [start, end), where the open bracket denotes inclusivity and the closed parenthesis denotes exclusivity. Thus, as depicted in FIG. 12, a node spanning positions [0,4) comprises CpG sites located at positions 0, 1, 2, and 3, where each of positions 0, 1, 2, and 3 has a corresponding genomic location. Similarly, a node spanning positions [0,5) comprises CpG sites located at positions 0, 1, 2, 3, and 4, where each of positions 0, 1, 2, 3, and 4 has a corresponding genomic location. In some embodiments, the genomic locations within a node correspond to locations of contiguous CpG sites.

Each fragment in Node 1 comprises the same start and end methylation sites (e.g., located at position 0 and position 3). Each fragment in Node 2 also comprises the same start and end methylation sites (e.g., located at position 0 and position 4). While each fragment in Node 1 comprises the same fragment methylation pattern (e.g., UMMU) in accordance with some embodiments, each fragment in Node 2 comprises different fragment methylation patterns (e.g., UMMUM and UMUUU), in accordance with some alternative embodiments of the present disclosure.

Each node further comprises a count of the fragments comprising each different fragment methylation pattern present in the node. For example, Node 1 comprises two fragments each comprising the same fragment methylation pattern (e.g., State: UMMU, Count: 2), and Node 2 comprises two fragments, each comprising a unique fragment methylation pattern (e.g., State: UMMUM, Count: 1; State: UMUUU, Count: 1). Each node in the interval map thus efficiently presents the methylation sequencing information in the dataset in a simplified and easily searchable format.

In some embodiments, each fragment in the first plurality of fragments in the first dataset is represented (e.g., as a representation of the fragment methylation pattern of the respective fragment) in a node in the one or more first state interval maps.

In some such embodiments, the one or more interval maps thus provides a reduced representation of a dataset (e.g., a methylation sequencing dataset) that is lossless with respect to the methylation states of all fragments in the plurality of fragments in the dataset. In some preferred embodiments, the one or more interval maps provide a reduced representation that is used for querying large datasets for resource discovery in a computationally tractable manner (e.g., text matching).

Methods for Generating Interval Maps.

While a description of constructing nodes for interval maps using fragment data from methylation sequencing datasets is provided above, multiple implementations for generating interval maps are possible.

For example, in some embodiments, the corresponding independent plurality of nodes of each respective interval map in the one or more first state interval maps is arranged as a corresponding tree that represents a corresponding region in the one or more corresponding genomic regions. Each respective node in the corresponding independent plurality of nodes for the respective interval map represents a sub-region of the corresponding genomic region.

In some embodiments, each corresponding tree arranges the corresponding independent plurality of nodes into a corresponding plurality of leaves in which a parent node for each leaf in the corresponding plurality of leaves references one or more child nodes.

In some embodiments, the independent plurality of nodes of each respective interval map is constructed using client/server resource discovery frameworks comprising a master node and a plurality of worker nodes, and/or structured or unstructured Peer-to-Peer resource discovery frameworks (e.g., MAAN, SWORD, Mercury, Brunet, Chord, CAN, and/or Pastry) that utilize a Distributed Hash Table (DHT) to manage object storage and lookup by mapping attribute values to DHT keys.

In some preferred embodiments, the tree is a one-dimensional version of a Kd tree with a randomized surface-area heuristic. See, e.g., Wald, 2007, "On Fast Construction of SAH-based Bounding Volume Hierarchies," IEEE, doi: 10.1109/RT.2007.4342588, which is hereby incorporated herein by reference in its entirety. In some embodiments, the tree is a self-organizing recursive-partitioning multicast tree.

In some embodiments, the tree is created using MatchTree. Match Tree is an unstructured, P2P-based resource discovery framework that creates a self-organizing tree for distributed query processing (e.g., text matching of intervals comprising methylation state patterns with genomic sequences and/or sequencing datasets) and aggregation of results (e.g., identification of intervals comprising the queried methylation state patterns). The tree structure minimizes failures of alternative methods that suffer from high administrative costs, scalability limitations, and loss of access to resources resulting from master node failure. Match Tree further provides advantages over structured P2P frameworks by supporting complex queries, partial string (e.g., substring) matching, and/or regular expression matching (e.g., wildcards), as well as guaranteeing query completeness (e.g., a thorough search of all available resources). See, e.g., Lee et al., 2013, "MatchTree: Flexible, scalable, and fault-tolerant wide-area resource discovery with distributed matchmaking and aggregation," Fut Gen Comp Sys 29, 1596-1610 which is hereby incorporated herein by reference in its entirety.

In some embodiments, interval maps are generated using any of the methods and embodiments described herein, or any modifications, substitutions, or combinations thereof as will be apparent to one skilled in the art. Notably, the use of interval maps for identification of methylation patterns provides advantages over conventional methods by improving both the sensitivity (e.g., query completeness) and the accuracy (e.g., matching) of methylation pattern identification.

Additionally, by reducing computational burden (e.g., where Match Tree requires less memory over alternative frameworks) interval maps can improve efficiency and reduce latency during the search for and identification of methylation patterns, thus providing critical benefits when handling large datasets (for example, when using large sequencing or methylation sequencing datasets generated by WGS and/or WGBS).

Propagating queries and aggregating results using interval maps (e.g., MatchTree) are discussed in detail in a later section of the present disclosure, and in e.g., Lee et al., 2013, "MatchTree: Flexible, scalable, and fault-tolerant wide-area resource discovery with distributed matchmaking and aggregation," Fut Gen Comp Sys 29, 1596-1610, which is hereby incorporated herein by reference in its entirety.

First and Second State Interval Maps.

Referring to block 242 of FIG. 2D, in some embodiments one or more second state interval maps are generated for one or more corresponding genomic regions using the second dataset. Each second state interval map in the one or more second state interval maps comprises a corresponding independent plurality of nodes. Each respective node in each corresponding independent plurality of nodes in the one or more second state interval maps is characterized by a corresponding start methylation site, a corresponding end methylation site, and for each different fragment methylation pattern observed across the second plurality of fragments in the second dataset between the corresponding start methylation site and the corresponding end methylation site of the respective node, (i) a representation of the different fragment methylation pattern and (ii) a count of fragments in the second dataset whose fragment methylation pattern begins at the corresponding start methylation site and ends at the corresponding end methylation site and has the different fragment methylation pattern.

In some embodiments, the one or more second state interval maps are generated using any of the methods disclosed herein (e.g., using any of the methods and/or embodiments described for the one or more first state interval maps).

In some embodiments, one or more first state interval maps and/or one or more second state interval maps represents one or more fragment methylation patterns in a respective plurality of fragments from a respective dataset, where the respective dataset is obtained from a cancer sample (e.g., one or more first and/or second interval maps are generated using a cancer dataset). In some embodiments, the one or more first state interval maps and/or the one or more second state interval maps represents one or more fragment methylation patterns in a respective plurality of fragments from a respective dataset, where the respective dataset is obtained from a non-cancer sample (e.g., one or more first and/or second interval maps are generated using a non-cancer dataset).

In some embodiments, one or more first state interval maps are generated using a cancer dataset, and one or more second state interval maps are generated using a non-cancer dataset. Alternatively, in some embodiments, one or more first state interval maps are generated using a non-cancer dataset, and one or more second state interval maps are generated using a cancer dataset. In some embodiments, one or more first state interval maps is generated using a dataset for a first cancer condition (e.g., cancer/non-cancer, cancer subtype, stage of cancer, and/or tissue-of-origin), and one or more second state interval maps is generated using a dataset for a second cancer condition that is different from the first cancer condition.

In some embodiments, each respective biological sample is represented by a respective one or more interval maps. In some embodiments, each respective test subject is represented by a respective one or more interval maps. In some alternative embodiments, a plurality of biological samples and/or a set of test subjects is represented by a respective one or more interval map (for example, where a plurality of biological samples and/or a set of test subjects in a study group are pooled).

For example, referring to block 244, in some embodiments, the one or more first state interval maps consist of a single first state interval map, and the one or more second state interval maps consists of a single second state interval map.

Referring to block 246, in some preferred embodiments, the one or more first state interval maps is a plurality of first state interval maps. Further, the one or more second state interval maps is a plurality of second state interval maps. Further still, the one or more corresponding genomic regions is a plurality of genomic regions. Each respective genomic region in the plurality of genomic regions is represented by a first state interval map in the first plurality of interval maps and a second state interval map in the second plurality of interval maps.

Referring to blocks 248-252 of FIG. 2D, in some such embodiments, the plurality of genomic regions is between 10 and 30 genomic regions. In some such embodiments, each genomic region in the plurality of genomic regions is a different human chromosome. In some such embodiments, the plurality of genomic regions consists of between two and 1000 genomic regions, between 500 and 5,000 genomic regions, between 1,000 and 20,000 genomic regions or between 5,000 and 50,000 genomic regions.

In some embodiments, the plurality of genomic regions corresponding to the plurality of first and/or second state interval maps is obtained using any of the methods for methylation sequencing disclosed herein. For example, referring to block 254 of FIG. 2D, in some preferred embodiments, the methylation sequencing of the obtaining the first dataset and obtaining the second dataset is targeted sequencing using a plurality of probes and each genomic region in the plurality of genomic regions is associated with a probe in the plurality of probes.

Identifying Qualifying Methylation Patterns.

Referring to block 256, in some embodiments the one or more first interval maps and the one or more second interval maps are scanned for a plurality of qualifying methylation patterns. Each such qualifying methylation pattern in the plurality of qualifying methylation patterns: (i) has a length that is in a predetermined CpG site number range, within the fragment methylation patterns of the one or more first interval maps and the one or more second interval maps, (ii) satisfies one or more selection criteria, and (iii) spans a corresponding CpG interval/between a corresponding initial CpG site and a corresponding final CpG site. As a result of this scanning, a plurality of qualifying methylation patterns that discriminates or indicates a cancer condition is identified. Detailed embodiments for identifying qualifying methylation patterns using selection criteria, query methylation patterns, and interval maps to identified methylation patters that discriminate or indicates a cancer condition are described below.

Selection Criteria for Qualifying Methylation Patterns.

In some embodiments, the identification of the plurality of qualifying methylation patterns that discriminates or indicates a cancer condition (e.g., that discriminates a first state of a cancer condition and a second state of a cancer condition) comprises identifying one or more methylation patterns that are differentially present between a first and a second cancer condition. In other words, in some embodiments, a qualifying methylation pattern comprises a sequence of CpG sites, corresponding to specific genomic regions or sub-regions, where one or more CpG sites in the sequence of CpG sites has a differential methylation state between a first and a second cancer condition. In some such embodiments, the extent to which a methylation pattern is differentially present between a first and a second cancer condition (e.g., the selection criteria) determines whether the methylation pattern is a qualifying methylation pattern.

For example, referring to block 258 of FIG. 2E, in some embodiments, the one or more selection criterion specifies that a methylation pattern (i) is represented in the one or more first interval maps with a first frequency that satisfies a first frequency threshold, (ii) is represented in the one or more first interval maps with a coverage that satisfies a first state depth, and (iii) is represented in the one or more second interval maps with a second frequency that satisfies a second frequency threshold.

Specifically, referring to block 260, in some such embodiments, (i) the methylation pattern is represented in the one or more first interval maps with a first frequency that satisfies a first frequency threshold when the frequency of the methylation pattern in the one or more first interval maps exceeds the first frequency threshold. Additionally, (ii) the methylation pattern is represented in the one or more first interval maps with a coverage that satisfies the first state depth when the coverage of the sequence reads encompassing the methylation pattern in the one or more first interval maps exceeds the first state depth. Finally, (iii) the methylation pattern is represented in the one or more second interval maps with a second frequency that satisfies the second frequency threshold when the frequency of the methylation pattern in the one or more second interval maps is less than the second frequency threshold.

For example, in some such embodiments, a methylation pattern must be present in the first plurality of fragments of the first dataset (e.g., as represented by the one or more first interval maps) at a frequency that is above a given first threshold, where the coverage depth (e.g., sequencing depth) of the first dataset at the genomic region corresponding to the respective methylation pattern (e.g., across the respective one or more CpG sites of the respective methylation pattern) is above a given depth. Conversely, the same methylation pattern must be present in the second plurality of fragments of the second dataset (e.g., as represented by the one or more second interval maps) at a frequency that is below a given second threshold. A methylation pattern that satisfies these constraints will, in some embodiments, be considered a qualifying methylation pattern.

In some embodiments, frequency is the number of times a methylation pattern is observed in a plurality of fragments in a respective dataset normalized by the number of fragments in the plurality of fragments comprising the respective methylation pattern (e.g., the coverage depth at the genomic region corresponding to the respective methylation pattern). In some embodiments, the frequency of a methylation pattern and/or the number of times a methylation pattern is observed in a respective dataset each is tallied by assigning each CpG site in the respective corresponding genomic region an identifier.

In certain exemplary embodiments, the above mentioned calculations are used to define the constraints for the selection criteria. For example, referring to block 262, in some embodiments the first frequency threshold is 0.2, the first state depth is 10, and the second frequency threshold is 0.001.

In some embodiments the first frequency threshold is a value between 0.05 and 0.40 (e.g., 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.39, or 0.40), the first state depth is between 2 and 100, and the second frequency threshold is less than 0.05 (e.g., less than 0.05, 0.04, 0.03, 0.02., 0.01, 0.0.005, 0.004, 0.001, 0.0001, etc.)

In some embodiments, the coverage depth of a first and/or second plurality of fragments in a respective first and/or second dataset is known. In some embodiments, a first and/or second plurality of fragments in a respective first and/or second dataset has a coverage depth that is a positive integer.

In some embodiments, referring to block 264, in some embodiments, a respective methylation pattern satisfies a selection criterion when the expression:

$$-\log_{10}\left(\frac{\text{second count}}{\text{second state depth}}\right)$$

for the methylation pattern exceeds 3, 4, 5 or 6, where second count is a count of the respective methylation pattern in the one or more second state interval maps, and second state depth is a coverage by the second dataset in the region, or regions, of the genome represented by the respective methylation pattern in the one or more second state interval maps.

In the case where there is a single second state interval map representing a single region of the genome bounded by a corresponding initial CpG site and a corresponding final CpG site, the second count is a count of the respective methylation pattern in the single second state interval map and the second state depth is the total number of fragments in the second dataset that span the corresponding initial CpG site and the corresponding final CpG site of the single second state interval map.

In the case where there are multiple second state interval maps, each representing a corresponding region of the genome bounded by a corresponding initial CpG site and a corresponding final CpG site, the second count is a summation of the count of the respective methylation pattern across the multiple single second state interval maps. Further, the second state depth is the total number of fragments in the second dataset that span the corresponding initial CpG site and the corresponding final CpG site associated with any second state interval map in the multiple second state interval maps.

In some embodiments, there is a single state interval map. In some embodiments, there are between two and one hundred state interval maps. In some embodiments there is a different state interval map for each different chromosome.

In some embodiments, e.g., when a first and/or second dataset comprises one or more pooled methylation sequencing datasets and/or an established control dataset with a fixed or otherwise non-limiting coverage depth, the coverage depth is not required to exceed a depth threshold for the methylation pattern to satisfy the selection criteria.

Other Characteristics of Qualifying Methylation Patterns.

In some embodiments, a qualifying methylation pattern is a differentially methylated sequence of non-contiguous CpG sites corresponding to a specific genomic region or sub-region (e.g., in a reference genome). In some embodiments, a qualifying methylation pattern is a differentially methylated sequence of contiguous CpG sites corresponding to a specific genomic region or sub-region.

In some embodiments, a qualifying methylation pattern is considered the equivalent of a variant allele. For example, in some embodiments, an interval of a defined length/of CpG sites corresponding to a specific genomic region or sub-region can have a plurality of distinct methylation patterns in one or more datasets. In some such embodiments, a variant allele is a first methylation pattern for a CpG interval/that differs from a second methylation pattern for the respective interval (e.g., at a specific locus). In some such embodiments, a first methylation pattern for a CpG interval 1 is defined as a reference allele, and a second methylation pattern for the same CpG interval 1, that is different from the first methylation pattern, is defined as a variant allele.

In some embodiments, three or more distinct methylation patterns (e.g., multiple variant alleles) are observed for a respective CpG interval/across the first and/or second datasets. In some such embodiments, where three or more methylation patterns are observed for a respective CpG interval 1, the stringency of the selection criteria is adjusted to select for only one qualifying methylation pattern at the respective CpG interval (e.g., the "rare variant"). In some embodiments, the stringency of the selection criteria is not adjusted and a plurality of qualifying methylation patterns is identified at the corresponding genomic region for the respective CpG interval, if each methylation pattern in the plurality of qualifying methylation patterns satisfies the selection criteria.

In some alternative embodiments, the plurality of methylation patterns satisfies the selection criteria when a methylation pattern is (i) represented in the one or more first interval maps with a first rate that satisfies a first rate threshold, (ii) represented in the one or more first interval maps with a coverage that satisfies a first state depth threshold, and (iii) represented in the one or more second interval maps with a second rate that satisfies a second rate threshold, where the rate is normalized by the coverage depth, pulldown bias, estimated tumor fraction, and position of the CpG interval at the specific locus (e.g., a Poisson rate). Query Methylation Patterns.

In some embodiments, scanning the one or more first interval maps and the one or more second interval maps for a plurality of qualifying methylation patterns comprises scanning for a plurality of query methylation patterns that each has a length that is in a predetermined CpG site number range and determining whether one or more query methylation patterns satisfy the one or more selection criteria. In some embodiments the predetermined CpG site number range is between five CpG sites and twenty CpG sites. In some embodiments the predetermined CpG site number range is a single CpG number (e.g., 5 CpG sites). Each query methylation pattern in the plurality of query methylation patterns comprises a sequence of methylation states within the predetermined CpG site number range, and scanning the one or more first interval maps and the one or more second interval maps for the plurality of query methylation patterns comprises identifying a methylation pattern, at a respective one or more genomic regions or sub-regions (e.g., at a specific locus or loci), that matches the query methylation pattern.

In some embodiments, a query methylation pattern comprises a representation of one or more methylation states. For example, in some embodiments, a query methylation pattern of length/=5 can be MMMMM, MMUMM or M/U in any combinations of M and U methylation states for the five methylation sites that make up a total length of 5 methylation sites (e.g., 5 CpG sites). In general, for a methylation pattern of length l, where l is a positive integer representing the number of unique methylation sites (e.g., CpG) in the methylation pattern, and where only methylation (M) versus unmethylation (U) is considered for each such methylation site, there are $2^l$ possible methylation patterns. Thus, for instance, for an eight methylation site (e.g., CpG) methylation pattern, there are $2\times2\times2\times2\times2\times2\times2\times2$ or 256 different possible methylation patterns.

In some preferred embodiments, scanning the one or more first interval maps and the one or more second interval maps comprises scanning for one or more query methylation patterns that are wholly contained in a plurality of fragment methylation patterns represented in a corresponding plurality of nodes. In some embodiments, a respective query methylation pattern comprises part of a respective fragment methylation pattern in a corresponding node. In some embodiments, a respective query methylation pattern consists of a respective fragment methylation pattern in a corresponding node.

In some alternative embodiments, each query methylation pattern in the plurality of query methylation patterns comprises a set of methylation states of length l, where l is a positive integer indicating the number of CpG sites and scanning the one or more first state interval maps and the one or more second state interval maps for the plurality of query methylation patterns comprises identifying a set of methylation states that matches the query set of methylation states. In some such embodiments, the set of methylation states at a respective one or more genomic regions or sub-regions (e.g., at a specific locus or loci) are contiguous, non-contiguous, in sequence, or out of sequence relative to the set of methylation states in the query methylation pattern.

In some embodiments, scanning the one or more first state interval maps and the one or more second state interval maps identifies a qualifying methylation pattern at a respective genomic region or sub-region that matches a corresponding query methylation pattern, where one or more methylation states in the qualifying methylation pattern differs from a respective one or more methylation states in the query methylation pattern. In some such embodiments, at least 1, at least 2, at least 3, at least 4, at least 5, at least 6, at least 7, at least 8, at least 9, at least 10, or more than 10 methylation states in the qualifying methylation pattern differs from the query methylation pattern.

In some embodiments, the at least 1, at least 2, at least 3, at least 4, at least 5, at least 6, at least 7, at least 8, at least 9, at least 10, or more than 10 methylation states in the qualifying methylation pattern that differs from the query methylation pattern is located at the start or end position of the query methylation pattern (e.g., wiggle). In some embodiments, the at least 1, at least 2, at least 3, at least 4, at least 5, at least 6, at least 7, at least 8, at least 9, at least 10, or more than 10 methylation states in the qualifying methylation pattern that differs from the query methylation pattern is located at a specific position in the query sequence (e.g., wildcard). For example, the specific position can be predetermined in the query methylation pattern using a symbol (e.g., "*", "/"). In some embodiments, one or more specific CpG sites (e.g., one or more unreliable CpG sites) are removed from a sequence of CpG sites in a query methylation pattern. In some embodiments, one or more specific CpG sites are bypassed in a sequence of CpG sites in a query methylation pattern by inserting a placeholder or substitute representation in the sequence of methylation states in the respective query methylation pattern (e.g., "*", "/").

In some embodiments, the plurality of query methylation patterns comprises one or more combinations, concatenations, spatial and/or structural relationships between one or more query methylation patterns. For example, in some such embodiments, scanning the one or more first state interval maps and the one or more second state interval maps searches for one or more query methylation patterns and/or any combinations thereof (e.g., using Boolean searches). In some embodiments, a query methylation pattern comprises regular expressions of query methylation patterns.

In some embodiments, scanning the one or more first state interval maps and the one or more second state interval maps for the plurality of qualifying methylation patterns searches for a plurality of query methylation states comprising all possible combinations of methylation states for a predetermined number of CpG sites (or predetermined CpG site number range). For example, in some embodiments, the predetermined CpG site number range is a single number–CpG length 1, and the plurality of all possible query methylation patterns of length/=3 comprises MMM, MMU, MUM, MUU, UMM, UMU, UMM, and UUU. In some embodiments, the plurality of possible query methylation patterns further comprises combinations of methylation states including representations for methylated, unmethylated, ambiguous, variant, and/or conflicted. In some embodiments, ambiguous, variant, and/or conflicted methylation sites are treated as wildcard sites. That is, if a candidate pattern qualifies but for the ambiguous, variant, and/or conflicted methylation site, the candidate pattern is deemed to qualify.

In some embodiments, the plurality of query methylation patterns comprises a predetermined set of query methylation patterns. In some such embodiments, the plurality of query methylation patterns comprises methylation patterns associated with the first state and/or the second state (e.g., biomarkers for one or more cancer conditions). In some embodiments, the predetermined set of query methylation patterns comprises known methylation patterns obtained from a methylation database (e.g., MethHC, MethHC 2.0, MethDB, PubMeth, IMETHYL, etc.), experimental findings, and/or publications. See, for example, Huang et al., 2021, "MethHC 2.0: information repository of DNA methylation and gene expression in human cancer," Nucleic Acids Research 49 (D1), D1268-D1275; Grunau et al., 2001, "MethDB—a public database for DNA methylation data," Nucleic Acids Research 29 (1), 270-274; Ongenaert et al., "PubMeth: a cancer methylation database combining text-mining and expert annotation," Nucleic Acids Research: doi: 10.1093/nar/gkm788; and Hachiya et al., 2017, "Genome-wide identification of inter-individually variable DNA methylation sites improves the efficacy of epigenetic association studies," NPJ Genom Med. 2017. 2:11, each of which is hereby incorporated by reference. In some embodiments, scanning for the plurality of methylation patterns searches for a predetermined set of methylation states at a specific predetermined locus (e.g., a specific one or more CpG sites indexed to a specific position in a reference genome). In some embodiments, a predetermined set of query methylation patterns and/or a predetermined one or more loci are obtained for each respective test subject and/or each respective biological sample for which a respective one or more interval maps are generated. In some embodiments, a single predetermined set of query methylation patterns and/or predetermined one or more loci are used to scan a plurality of interval maps across a plurality of test subjects and/or biological samples.

In some embodiments, the plurality of query methylation patterns is filtered to remove one or more query methylation patterns that satisfy a similarity threshold to a second one or more query methylation patterns. Such filtering ensures that each pattern has some degree of uniqueness. For instance, in some embodiments such filtering removes a methylation pattern that is 50 percent, 60 percent, 70 percent, 80 percent, 90 percent, or more than 95 percent similar to a second one or more query methylation patterns in the plurality of methylation patterns. For instance, consider the example methylation patterns MMMMM and MMUMM, where the similarity threshold is 70%, meaning that when at least 70% of the methylation sites in the two patterns are the same, the similarity threshold is considered satisfied. In this example, the two methylation patterns have the same methylation values at 5 out of their 6 methylation sites and therefore have a similarity of $5/6$ or 83%. Thus, in this example one of the two methylation patterns is removed from the query methylation patterns.

Referring to blocks 266-270, in some embodiments, each possible methylation pattern of length/methylation sites is sampled by the plurality of queries. In some embodiments, 1 is 3, 4, 5, 6, 7, 8, 9, 10, 11, 12, 13, 14, 15, 16, 17, 18, 19, or 20 CpG sites. In some embodiments, the CpG site number range is/contiguous CpG sites. In some embodiments, 1 is 3, 4, 5, 6, 7, 8, 9, 10, 11, 12, 13, 14, 15, 16, 17, 18, 19, or 20 contiguous CpG sites. In some embodiments, the predetermined CpG number range is between 2 and 100 contiguous CpG sites in a human reference genome.

In some embodiments, the predetermined number of CpG sites is adaptive. In some embodiments, the predetermined number of CpG sites is a range of +/−A from a defined number of CpG sites, where integer (e.g., 1, 2, 3, 4, 5, etc.). Scanning Interval Maps.

In some embodiments, the one or more first interval maps and/or the one or more second interval maps are filtered prior to the scanning to remove corresponding genomic regions and/or sub-regions and thereby reduce the computational burden of the scanning and identifying. In some embodiments, the filtering removes genomic regions that are excluded (e.g., blacklisted regions and/or poorly discriminating regions). In some embodiments, the filtering removes genomic regions with high noise levels. For example, in some embodiments, regions with high noise can skew results by artificially imposing a lower bound on tumor fraction estimates (see, e.g., Example 4 below for further discussion on calculation and analysis of noise in methylation state intervals).

Referring to block 272, in some embodiments, the corresponding independent plurality of nodes of each respective interval map in the one or more first interval maps is arranged as a corresponding tree (e.g., a one-dimensional version of a Kd tree with a randomized surface-area heuristic as described in Wald, 2007, "On Fast Construction of SAH-based Bounding Volume Hierarchies," IEEE, doi: 10.1109/RT.2007.4342588, a tree that is created using Match Tree as described in Lee et al., 2013, "MatchTree: Flexible, scalable, and fault-tolerant wide-area resource discovery with distributed matchmaking and aggregation," Fut Gen Comp Sys 29, 1596-1610; doi: 10.1016/j.future.2012.08.009, etc.) that represents a corresponding region in the one or more corresponding genomic regions. Each respective node in the corresponding independent plurality of nodes for the respective interval map represents a sub-region of the corresponding genomic region.

Figure 2F:
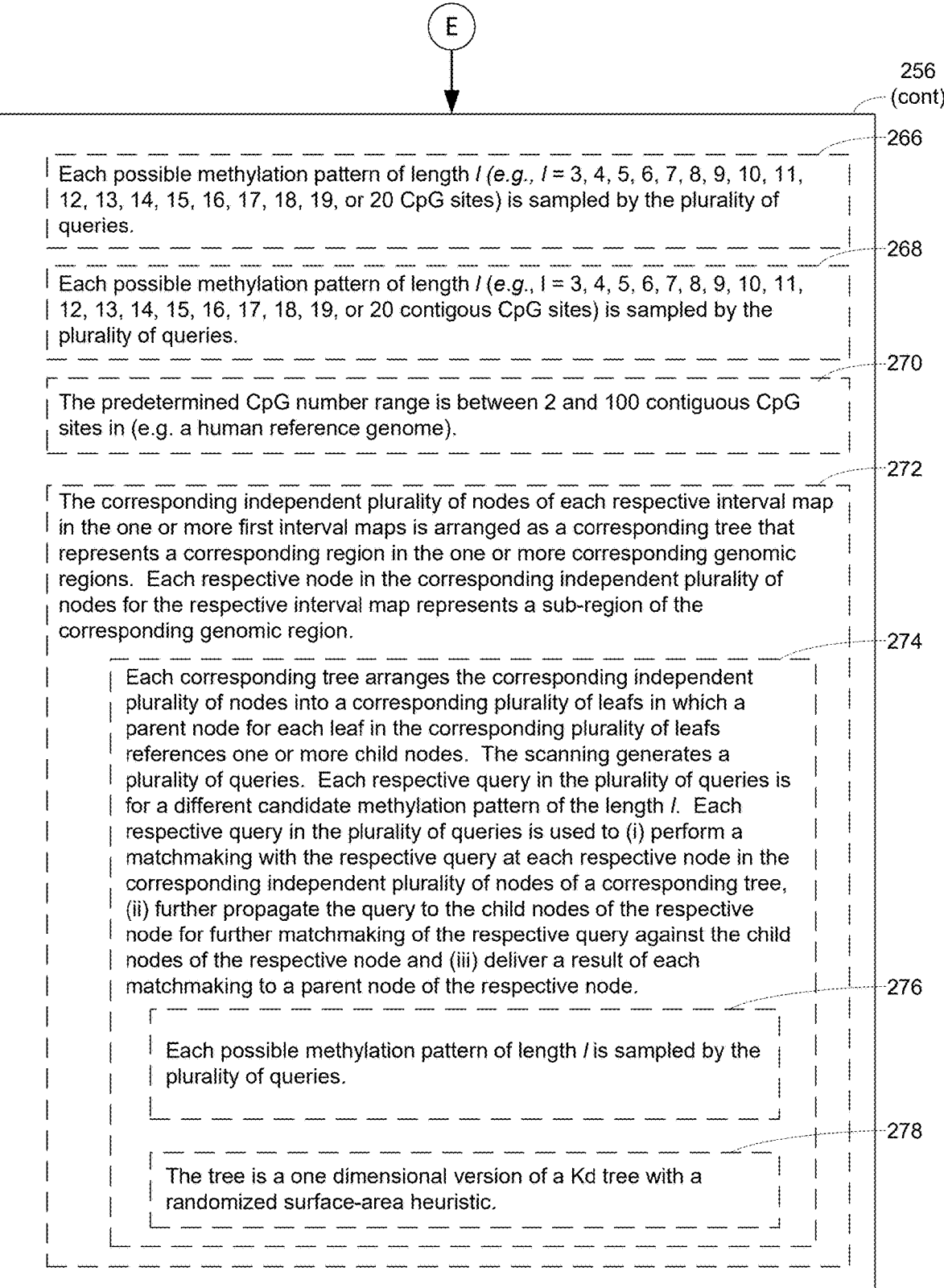

Referring to block 274 of FIG. 2F, in some such embodiments, each corresponding tree arranges the corresponding independent plurality of nodes into a corresponding plurality of leaves in which a parent node for each leaf in the corresponding plurality of leaves references one or more child nodes. The scanning the one or more first interval maps and the one or more second interval maps generates a plurality of queries, where each respective query in the plurality of queries is for a different candidate methylation pattern of the length 1. Additionally, each respective query in the plurality of queries is used to (i) perform a matchmaking with the respective query at each respective node in the corresponding independent plurality of nodes of a corresponding tree, (ii) further propagate the query to the child nodes of the respective node for further matchmaking of the respective query against the child nodes of the respective node and (iii) deliver a result of each matchmaking to a parent node of the respective node.

For example, referring to FIG. 12, scanning the interval map for a query methylation pattern comprising the sequence of methylation states "UMM" at CpG site positions 0, 1, 2 (e.g., [0,3)) returns all nodes comprising one or more fragments that comprise the query methylation pattern. Thus, the query performs a matchmaking at each node and propagates the results (e.g., returning Nodes 1 and 2). The frequency of the queried methylation pattern is calculated from the propagated results using the count of the fragments in each respective node whose fragment methylation patterns comprise the query methylation pattern. For example, the frequency of the methylation pattern UMM at CpG sites positions 0, 1, 2 in Nodes 1 and 2 is computed as 75% (2 counts of UMM at Node 1, 1 count of UMM at node 2, and 1 count of UMU at node 2 for positions 0, 1, and 2, for a total of 3 counts of UMM out of the 4 patterns counted at positions 0, 1, and 2 across nodes 1 and 2 as illustrated in FIG. 12).

In some embodiments, scanning the interval map for a query methylation pattern scans each respective node for the query methylation pattern at any possible starting methylation location within the node. For example, in some such embodiments, a query returns a node even when the query methylation pattern does not start at the first methylation site of the node. For instance, referring to FIG. 12, in node 1, in some embodiments when the search query is MMU, nodes 1 and 2 will both be identified even though the pattern does not begin at the first methylation site of respective nodes 1 and 2. Similarly, in some embodiments, scanning the interval map for a query methylation pattern scans the beginning, middle, and/or ends of a node. In some embodiments, scanning the interval map for a query methylation pattern scans each respective node for query methylation patterns comprising methylated, unmethylated, ambiguous, variant, and/or conflicted states.

Referring to block 276, in some embodiments, each possible methylation pattern of length/within a node is sampled by the plurality of queries. Thus, for example, consider the case of fragment UMMU of node 1 of FIG. 12 and a search query of UM (and where the search does not require the pattern to begin at the first methylation site of the node). In this example, the search query will examine positions 1 and 2 of UMMU for a match to the search query UM, positions 2 and 3 of UMMU for a match to the search query UM, and positions 3 and 4 of UMMU for a match to the search query.

Referring to block 278, in some preferred embodiments, the tree is a one-dimensional version of a K-dimensional tree with a randomized surface-area heuristic. See, e.g., Wald, 2007, "On Fast Construction of SAH-based Bounding Volume Hierarchies," IEEE, doi: 10.1109/RT.2007.4342588, which is hereby incorporated herein by reference in its entirety. In some alternative embodiments, the tree is a self-organizing recursive-partitioning multicast tree. In some such embodiments, scanning the interval map is performed using Match Tree.

In some such embodiments, delivering a result of the matchmaking to a parent node in the corresponding tree occurs recursively, thereby aggregating the results from all child nodes to the parent node. In some such embodiments, the query to be matched is obtained by the Match Tree algorithm as a resource requirement. In some implementations, additional parameters required for returning a result (e.g., best-fit, exact match, coverage depth, minimum or maximum VAF, start position, end position, and/or other values determining sorting or filtering) are obtained as rank criteria. Nodes that satisfy the resource requirement are ranked by the rank criteria, and, given a specified desired number k of results (e.g., nodes), MatchTree returns the top k nodes as ranked by the rank criteria.

In some embodiments, queries are modified using heuristics to define query response time and/or set limits on the amount of generated responses by estimating the number of response nodes included in the tree, in order to reduce computational burden. For example, in some such embodiments, cached result distributions from previous implementations of the scanning are used to predict likely results (e.g., nodes) comprising the desired resources (e.g., methylation patterns).

In some embodiments, queries comprise using timeout values (e.g., dynamic timeout with aggregation progress, autonomic timeout, and/or static timeout with user input) and/or redundant topology to avoid network failure and provide consistent performance. For example, in some such embodiments, first-fit resource discovery improves latency by returning aggregated results from child nodes to parent nodes when a threshold desired number k of results is met, rather than after all possible results are aggregated. Additionally, in some embodiments, redundant topology is used to propagate queries and aggregate results in both forward and reverse directions, in order to ensure query completeness in the event of node failure.

See, e.g., Lee et al., 2013, "MatchTree: Flexible, scalable, and fault-tolerant wide-area resource discovery with distributed matchmaking and aggregation," Fut Gen Comp Sys 29, 1596-1610; doi: 10.1016/j.future.2012.08.009, and Wang et al., 2015, "Syntax-based Deep Matching of Short Texts," arXiv: 1503.02427v6 [cs.CL], each of which is hereby incorporated herein by reference in its entirety.

In some alternative embodiments, a method other than an interval map is used to identify a plurality of qualifying methylation patterns that discriminates or indicates a cancer condition. In some embodiments, identifying a plurality of qualifying methylation patterns is performed using any of the methods and embodiments described herein (e.g., scanning interval maps), or any modifications, substitutions, alternatives or combinations thereof as will be apparent to one skilled in the art.

Discriminating Cancer Conditions.

In some embodiments, the scanning identifies a plurality of qualifying methylation patterns discriminating a first cancer condition (e.g., cancer/non-cancer, cancer subtype, stage of cancer, and/or tissue-of-origin) from a second cancer condition that is different from the first cancer condition. For example, in some embodiments, the plurality of qualifying methylation patterns includes a library of methylation patterns that discriminate cancer from non-cancer (e.g., healthy control), cancer subtypes and/or tissue-of-origin (e.g., lung cancer-specific biomarkers), and/or stages of cancer. In some embodiments, the plurality of qualifying methylation patterns is used to perform a positive verification of the presence/absence of a specific cancer condition (e.g., cancer/non-cancer, cancer subtype, stage of cancer, and/or tissue-of-origin).

In some embodiments, the plurality of qualifying methylation patterns is identified using tissue samples and/or blood samples (e.g., cfDNA). In some embodiments, for a respective one or more test subjects, the plurality of qualifying methylation patterns identified using tissue samples and the plurality of qualifying methylation patterns identified using blood samples are the same. In some embodiments, the plurality of qualifying methylation patterns is identified using blood samples, and the tumor fraction estimate is calculated based on a positive correlation between tumor frequency and tumor-derived cfDNA. See, for example, Example 4 below for further discussion on the concordance between tumor fraction estimates performed using cfDNA and tissue samples.

In some embodiments, the plurality of qualifying methylation patterns is identified using a first and second dataset obtained from one or more biological samples from a single respective test subject. For example, in some such embodiments, a first plurality of qualifying methylation patterns discriminates between tumor and healthy tissue for a first test subject, and a second plurality of qualifying methylation patterns discriminates between tumor and healthy tissue for a second test subject, where the first plurality of qualifying methylation patterns and the second plurality of qualifying methylations patterns are different. In some such embodiments, a respective plurality of qualifying methylation patterns is used to monitor tumor fraction before and after cancer treatment (e.g., for minimal residual disease and/or recurrence monitoring) for a respective test subject over a specified period of time.

In some embodiments, the plurality of qualifying methylation patterns is identified using a first dataset obtained from one or more biological samples from a single respective test subject, and a second dataset obtained from one or more biological samples from one or more control test subjects (e.g., a control healthy cohort).

In some embodiments, the plurality of qualifying methylation patterns is identified using a first dataset obtained from one or more biological samples from one or more test subjects (e.g., a test cohort), and a second dataset obtained from one or more biological samples from one or more control test subjects (e.g., a control healthy cohort).

In some embodiments, the plurality of qualifying methylation patterns is identified using a first dataset obtained from one or more biological samples from a first one or more test subjects (e.g., a first test cohort), and a second dataset obtained from one or more biological samples from a second one or more test subjects (e.g., a second test cohort). In some such embodiments, qualifying methylation patterns identified using a first and second test cohort is used to provide information on commonalities between patients or within large study groups, or can be used to identify stratifying features of qualifying methylation patterns that discriminate between two or more cancer conditions.

In some embodiments, the plurality of qualifying methylation patterns is identified using a first interval map constructed from a first dataset obtained from one or more biological samples from a first one or more test subjects (e.g., a test cohort), and a representation of a second interval map that denotes regions of the second interval map that satisfy the selection criterion. In some such embodiments, the plurality of methylation patterns is identified without using a second dataset obtained from a respective biological sample from a corresponding subject in a first set of subjects. Rather, in some such embodiments, the selection criteria can be satisfied by scanning only the first interval map using a plurality of query methylation patterns that is known or estimated to satisfy the selection criteria. For example, a panel of methylation state intervals that are known or estimated to be poorly represented in a second cancer condition (e.g., through experimentation or prior knowledge) can be used to scan a first interval map comprising the fragment methylation patterns, counts (e.g., frequencies) and coverage depth of a first dataset, without the requirement of scanning a second interval map. Alternatively, in some embodiments, a selection criterion is defined that assumes the presence of outlier fragment methylation patterns in a first cancer condition compared to a second cancer condition (e.g., where variant alleles are assumed to be enriched in tumor samples over non-cancer samples). For example, in some such embodiments, a selection criterion may be defined as a methylation pattern frequency (e.g., sometimes also referred to as a variant allele frequency) above a predefined threshold (e.g., greater than 0.5) in the first (e.g., tumor) cancer condition. In some embodiments, the predefined threshold is determined by experimental findings or prior knowledge. In some embodiments, the predefined threshold is set by a user or practitioner.

In some embodiments, the plurality of qualifying methylation patterns is 2 or more methylation patterns at two or more distinct regions of the genome. In some embodiments the plurality of qualifying methylation patterns is 3, 4, 5, 6, 7, 8, 9, 10, 11, 12, 13, 14, 15, 16, 17, 18, 19, 20, or more than 20 methylation patterns, where each such methylation patten maps to a unique portion of a reference genome and thus represents a unique set of methylation sites. In some embodiments, the plurality of qualifying methylation patterns is more than 30, 40, 50, 60, 70, 80, 90, 100, 110, 120, 130, 140, 150, 160, 170, 180, 190, 200, or more methylation patterns, where each such methylation patten maps to a unique portion of a reference genome and thus represents a unique set of methylation sites. In some embodiments, each of the methylation patterns maps to a genomic region described in International Patent Publication No. WO2020154682A3, entitled "Detecting Cancer, Cancer Tissue or Origin, or Cancer Type," which is hereby incorporated by reference, including the Sequence Listing referenced therein. In some embodiments, some or all of the methylation patterns uniquely map to a genomic region described in International Patent Publication No. WO2020/069350A1, entitled "Methylated Markers and Targeted Methylation Probe Panel," which is hereby incorporated by reference, including the Sequence Listing referenced therein. In some embodiments, some or all of the methylation patterns uniquely map to a genomic region described in International Patent Publication No. WO2019/195268A2, entitled "Methylated Markers and Targeted Methylation Probe Panels," which is hereby incorporated by reference, including the Sequence Listing referenced therein.

In some embodiments, the plurality of qualifying methylation patterns is filtered to remove methylation patterns identified by a variant caller algorithm, such as FreeBayes, VarDict, MuTect, MuTect2, MuSE, FreeBayes, VarDict, and/or MuTect (see Bian, 2018, "Comparing the performance of selected variant callers using synthetic data and genome segmentation," BMC Bioinformatics 19:429, which is hereby incorporated by reference) identifies the methylation pattern as a germline variant.

In some embodiments, the plurality of qualifying methylation patterns is filtered to remove methylation patterns that appear at least twice (e.g., in two different fragments) in a reference in the methylation sequencing of biological samples obtained from a cohort of subjects (e.g., a cohort of healthy subjects). In some embodiments each subject in the cohort of subjects is represented by the first dataset. In some embodiments each subject in the cohort of subjects is represented by the second dataset. In some embodiments each subject in the cohort of subjects is not represented by the first or second dataset.

In some embodiments, the plurality of qualifying methylation patterns is filtered to remove methylation patterns that appear with greater than a minimum frequency across the unique test fragments of a reference cohort of subjects (e.g., a cohort of healthy subjects). For instance, in some embodiments a respective qualifying methylation pattern occurring in at least 20% of the nucleic acid fragments mapping to the genomic region associated with the respective qualifying methylation pattern from the cohort of subjects (e.g., a cohort of healthy subjects) serves as the basis for removing the respective qualifying methylation pattern from the plurality of qualifying methylation patterns. In some embodiments, rather than imposing a threshold of 20%, a condition (threshold) in which at least 3%, at least 5%, at least 10%, at least 15%, at least 25%, at least 30%, at least 35%, at least 40%, at least 45%, or at least 50% of the nucleic acid fragments from the cohort have the respective qualifying methylation pattern (at the genomic region of the qualifying methylation pattern) serves as the basis for removing the respective qualifying methylation pattern from the plurality of qualifying methylation patterns. In some embodiments each subject in the cohort of subjects is represented by the first dataset. In some embodiments each subject in the cohort of subjects is represented by the second dataset. In some embodiments each subject in the cohort of subjects is not represented by the first or second dataset.

In some embodiments, the plurality of qualifying methylation patterns is filtered to remove methylation patterns that appear with less than a minimum frequency across the unique test fragments of a reference cohort of subjects (e.g., a cohort of subjects with a particular cancer condition). For instance, in some embodiments a respective methylation pattern occurring in less than 20% of the nucleic acid fragments mapping to the genomic region associated with the respective qualifying methylation pattern from the cohort of subjects with the particular cancer condition is removed. In some embodiments rather than imposing a threshold of 20%, a condition (threshold) in which less than 8%, less than 15%, less than 20%, less than 30%, less than 40%, less than 50%, less than 60%, less than 70%, or less than 80% of the nucleic acid fragments from the cohort have the respective qualifying methylation pattern (at the genomic region of the qualifying methylation pattern) serves as the basis for removing respective qualifying methylation pattern from the plurality of qualifying methylation patterns. In some embodiments each subject in the cohort of subjects is represented by the first dataset. In some embodiments each subject in the cohort of subjects is represented by the second dataset. In some embodiments each subject in the cohort of subjects is not represented by the first or second dataset.

In some embodiments, the plurality of qualifying methylation patterns is filtered to remove alleles (methylation patterns) found in public databases such as the gnomAD and dbDNP datasets. For information on such datasets, see Karczewski et al., 2019, "Variation across 141,456 human exomes and genomes reveals the spectrum of loss-of-function intolerance across human protein-coding genes," bioRxiv doi.org/10.1101/531210 and Sherry et al., 2011, "dbSNP: the NCBI database of genetic variation" Nuc. Acids. Res. 29, 308-311.

Methods of Use.

In some embodiments, the method provided in the present disclosure is used to identify qualifying methylation patterns discriminating or indicating a cancer condition for input into downstream applications. Uses for qualifying methylation patterns include, but are not limited to, estimating tumor fraction, probing classifier behavior, investigating alternative features, classifying disease (e.g., cancer conditions), and/or determining minimal residual disease.

Classifiers.

In some embodiments, the method further comprises training a classifier to discriminate or indicate a state of the cancer condition using at least methylation pattern information associated with the plurality of qualifying methylation patterns identified using the first and second datasets.

For example, in some embodiments, an untrained classifier is trained on a training set comprising one or more qualifying methylation patterns that discriminate or indicate a cancer condition identified using the method of generating and scanning interval maps disclosed herein. In some embodiments, an untrained classifier is trained on a training set comprising one or more qualifying methylation patterns that discriminate or indicate a cancer condition identified using any alternative method other than interval mapping.

In some embodiments, the classifier is logistic regression. In some embodiments, the classifier is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

Classifiers are described in further detail in, e.g., U.S. patent application Ser. No. 17/119,606, entitled "Cancer classification using patch convolutional neural networks," filed Dec. 11, 2020, and United States Patent Publication No. 2020-0385813 A1, entitled "Systems and Methods for Estimating Cell Source Fractions Using Methylation Information," filed Dec. 18, 2019, each of which is hereby incorporated herein by reference in its entirety.

In some embodiments, a trained classifier trained on one or more qualifying methylation patterns that discriminate or indicate the cancer condition is used to validate the training by classifying a state of a cancer condition of the first and/or second datasets. In some alternative embodiments, a trained classifier trained on one or more qualifying methylation patterns that discriminate or indicate the cancer condition is further used to classify a state of a cancer condition of a third dataset (e.g., of an unknown sample or test subject) by assessing the methylation states of the third dataset in the respective genomic regions or sub-regions at which the qualifying methylation patterns were identified.

Thus, in some embodiments, a third dataset is obtained, in electronic form, where the third dataset comprises a corresponding fragment methylation pattern of each respective fragment in a third plurality of fragments. The corresponding fragment methylation pattern of each respective fragment (i) is determined by a methylation sequencing of nucleic acids from a biological sample obtained from a test subject and (ii) comprises a methylation state of each CpG site in a corresponding plurality of CpG sites in the respective fragment. The method further comprises applying the fragment methylation pattern of each respective fragment in the third plurality of fragments in the third dataset that encompasses or corresponds to a qualifying methylation pattern in the plurality of qualifying methylation patterns to the classifier to thereby determine the state of the cancer condition in the test subject. Thus, for example, consider the case where the plurality of qualifying methylation patterns is a set of 20 particular methylation patterns mapping to 20 different genomic regions. In this instance, the methylation pattern exhibited by the test subject at these 20 different genomic regions from the methylation sequencing of nucleic acids from a biological sample is inputted into the classifier in such embodiments to ascertain the state of the cancer condition of the test subject. It will be appreciated that the methylation pattern at these 20 different genomic regions may not be a homogenous pattern. In fact, sequencing data for the test subject may indicate that there are several different methylation patterns at the 20 different genomic regions associated with the 20 qualifying methylation patterns. In some such embodiments, methylation patterns observed for the test subject at the 20 different genomic regions is inputted into the classifier. For instance, consider a nonlimiting example where, for the genomic region associated with the first qualifying methylation pattern in the plurality of qualifying methylation patterns, the methylation sequencing for the test subject produces 35 fragments mapping to the genomic region with methylation pattern A and 70 fragments mapping to the genomic region with methylation pattern B. In this example, an indication of both methylation patterns A and B is inputted to the classifier along with an indication that methylation pattern A was observed among 35/105 of the fragments mapping to the first genomic position and that methylation pattern B was observed among 70/105 of the fragments mapping to the first genomic position. In other embodiments, the classifier does not consider proportions of patterns at the genomic regions that the plurality of qualifying methylation patterns map to, but rather, just a binary indication as to whether a threshold number of fragments with the methylation pattern have been found at the genomic position (e.g., at least two fragments, etc.). In other embodiments, the classifier does not consider proportions of patterns at the genomic regions that the plurality of qualifying methylation patterns map to, but rather, just a binary indication as to whether a threshold number of fragments, each sequenced with a threshold coverage, with the methylation pattern have been found at the genomic position (e.g., at least two fragments each having a threshold coverage of at least 20, etc.).

In some embodiments, the third dataset is obtained using any of the methods disclosed herein (e.g., using any of the methods and/or embodiments described for the first and second datasets).

In some embodiments, the biological sample and/or the test subject is obtained using any of the methods disclosed herein (e.g., using any of the methods and/or embodiments described for the first and second datasets).

In some embodiments, the biological sample obtained from the test subject is a liquid biological sample (e.g., blood and/or cfDNA). In some embodiments, the biological sample is a tissue biological sample (e.g., tumor sample).

In some embodiments, the third plurality of fragments is cell-free nucleic acids. For example, in some preferred embodiments, the obtaining the third dataset to determine the state of the cancer condition in the test subject does not require obtaining tissue samples (e.g., biopsy samples). In some embodiments, the third plurality of fragments from the test subject comprises 100 or more cell-free nucleic acid fragments, 1000 or more cell-free nucleic acid fragments, 10,000 or more cell-free nucleic acid fragments, 100,000 or more cell-free nucleic acid fragments, 1,000,000 or more cell-free nucleic acid fragments, or 10,000,000 or more nucleic acid fragments.

In some such embodiments, the method further comprises obtaining a plurality of datasets, in addition to the first and second datasets, where each respective dataset in the plurality of datasets comprises a corresponding fragment methylation pattern of each respective fragment in a respective plurality of fragments. The corresponding fragment methylation pattern of each respective fragment (i) is determined by a methylation sequencing of nucleic acids from a biological sample obtained from a test subject and (ii) comprises a methylation state of each CpG site in a corresponding plurality of CpG sites in the respective fragment. The method further comprises applying the fragment methylation pattern of each respective fragment in the respective plurality of fragments in the respective dataset that encompasses or corresponds to a qualifying methylation pattern in the plurality of qualifying methylation patterns to the classifier to thereby determine the state of the cancer condition in the test subject.

In some such embodiments, each respective dataset in the plurality of datasets is obtained sequentially from a single test subject over a period of time. In some embodiments, each respective plurality of fragments are cell-free nucleic acids. For example, in some preferred embodiments, the obtaining each respective dataset in the plurality of datasets to determine the state of the cancer condition in the test subject does not require obtaining tissue samples (e.g., biopsy samples).

In some embodiments, the state of the cancer condition is absence or presence of a cancer. In some embodiments, the state of the cancer condition is a stage of cancer. In some embodiments, the state of the cancer condition is a cancer subtype or a tissue-of-origin for a cancer. For example, in some embodiments, the cancer is adrenal cancer, biliary track cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

Tumor Fraction Estimation.

Figure 15A:
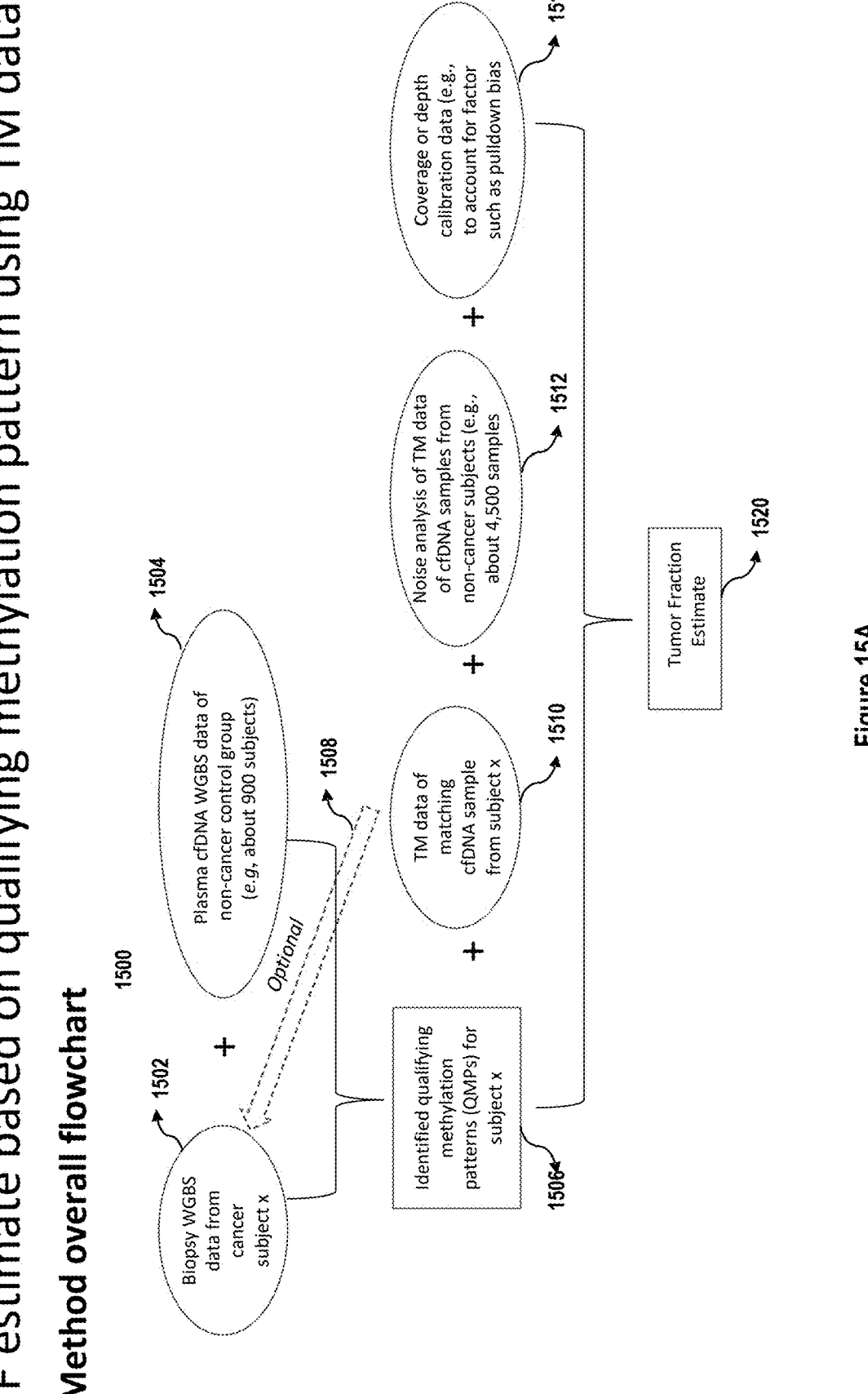
Figure 16:
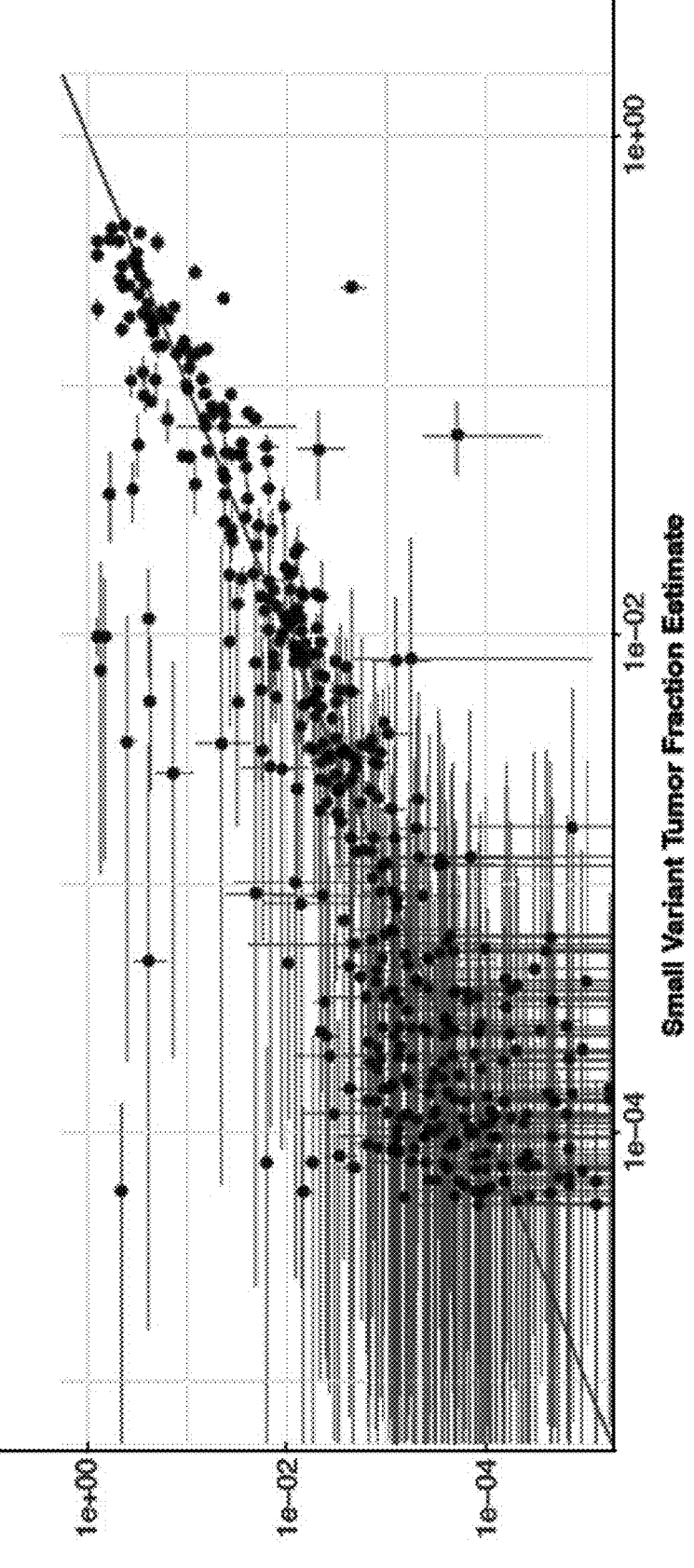
FIG. 16 illustrates estimated cfDNA tumor fraction against matched tumor biopsy in accordance with an embodiment of the present disclosure.

In some embodiments, the state of cancer condition is tumor fraction. For example, tumor fraction estimates are calculated in some embodiments based on the assumption that one or more methylation state patterns in blood (e.g., cfDNA and/or plasma) are tumor-derived, and that the frequency of such tumor-derived variant alleles are directly proportional to the fraction of cancer cells to normal cells (e.g., the tumor fraction). In some embodiments, the method for tumor fraction estimation is performed using sequencing data from WGBS, targeted methylation sequencing (TM sequencing), WGS, and/or targeted sequencing (e.g., using small variants). FIGS. 13A and 13B illustrate a few approaches based on the small variants. FIGS. 14 and 15 illustrate two examples showing alternative methods to these small variant-based methods. In these embodiments, instead of small variants, selected methylation patterns (e.g., qualifying methylation patterns or QMPs) are used as basis for estimating tumor fractions based on methylation sequencing data, especially when small variant identification is compromised by factors such as bisulfite conversion. The QMP-based methods can be applied to both WGBS (e.g., FIGS. 14A and 14B) and TM sequencing data (e.g., FIGS. 15A and 15B).

In some embodiments, the state of cancer condition is tumor fraction, the first state of the cancer condition is a first range of tumor fraction, and the second state of the cancer condition is a second range of tumor fraction.

For example, in some embodiments, the first range is greater than 0.001 and the second range is less than 0.001.

In some embodiments, the tumor fraction estimate is used to plot a probability of cancer (e.g., using a classifier).

In some embodiments, the probability of cancer is used to determine the limit of detection. In some such embodiments, the limit of detection is 0.1%.

In some embodiments, tumor fraction is calculated from a plurality of qualifying methylation patterns (QMPs; see, for example the disclosure for FIGS. 14 and 15). In an example embodiment, posterior tumor fraction estimates are generated using counts of fragments that comprise the qualifying methylation pattern and counts of fragments that do not comprise the qualifying methylation pattern at the respective genomic region corresponding to each respective qualifying methylation pattern (e.g., variant-matched and non-matched fragments covering each variant site).

In some such embodiments, where targeted methylation sequencing has been used, a Poisson likelihood model per site (e.g., per genomic site corresponding to the respective qualifying methylation pattern "QMP genomic site") is employed. In some embodiments, this Poisson likelihood model calculates a rate constant as a function of the tumor fraction, the pull-down bias (to correct for pull-down bias introduced through the use of probes with particular allelic patterns represented to the exclusion of alternate allelic patterns at the QMP genomic site), the estimated total sequencing depth, and the background noise rate.

For example, in some embodiments, the tumor fraction estimate is calculated from the posterior likelihood calculation:

$$Prob(tf | \text{data}) \sim \prod_{i=1}^{n} Pois(x_i; \lambda_i) * Prob(tf) \qquad \text{(Equation 1)}$$

where:
$x_i$=abnormal counts at QMP genomic site i in cfDNA,
$t_f$=tumor fraction,
$\lambda_i$=Poisson lambda for QMP genomic site $$\lambda_i = [tf * Qf_i + (1 - tf) * \widehat{noise}_i * \widehat{depth}_i],$$

$Qf_i$=QMP fraction for QMP genomic site i in the biopsy sample,
$\widehat{noise}_i$ =estimated site specific noise rate in cfDNA, and where depth is adjusted based on a depth function:
$\widehat{depth}_i$..

In some embodiments, pull-down bias is estimated per QMP genomic site i (bias$_i$), where (bias$_i$) is the pull-down bias at the QMP genomic site i as follows:

$pc1$ = psuedocount to smooth pull-down bias estimate $$alpha = \frac{75^{th} \text{ quantile } WGBS \text{ control } (WGBS \text{ count}) \text{ abnormal counts}}{75^{th} \text{ quantile } TM \text{ control } (TM \text{ count}) \text{ abnormal counts}},$$

bias$_i$ = pull-down bias at $QMP$ genomic site i, and bias$_i$ = alpha * $(x_{i,TMct} + pc1)/(x_{i,WGBSct} + pc1)$.

This above-described pull-down bias corrects for pull-down bias in targeted methylation sequencing at a QMP genomic site i using WGBS control data as well as TM control data. In particular, such control data is used to compute alpha. That is, to compute alpha, the abnormal counts at each site in a plurality of QMP genomic sites (under study) from a WGBS control are obtained ("control (WGBS count) abnormal counts"). As such, there are a plurality of WGBS abnormal counts, each for a different QMP genomic site obtained using the WGBS control. There is no particular requirement on the cancer state of this WGBS control. In other words, the WGBS control can have a particular cancer state or not have a particular cancer state. In some embodiments, the WGBS control is an engineered cell line that has a predetermined known percentage of methylated genomic DNA that is sequenced using WGBS. In some embodiments the WGBS control is a mixture of 0% methylated and 100% methylated genomic DNA at predetermined compositions (e.g., 50/50 or 40/60 or 30/70 mixture of 0% and 100% methylated genomic DNAs). Further, the abnormal counts at each site in a plurality of QMP genomic sites from a targeted methylation sequencing are obtained ("TM control (TM count) abnormal counts"). In typical embodiments the source of DNA for the TM control is the same as for the WGBS control, the only difference being that, for the TM control, the control DNA is sequenced using targeted sequencing with the pull-down probes used in the TM rather than by WGBS. The quantity alpha in such embodiments, represents a slope of a line fitted to a scatterplot of control (WGBS count) abnormal counts/TM control (TM count) abnormal counts. Each respective point in the scatterplot is for a different QMP genomic site j in the plurality of QMP genomic sites under study, where the x coordinate for the respective point is (WGBS count) abnormal counts at genomic site j and the y coordinate for respective point is (TM count) abnormal counts at genomic site j. Moreover, as indicated in the equation for alpha, in typical embodiments only data from the $75^{th}$ quantile of the WGBS control (WGBS count) abnormal counts and only data from the $75^{th}$ quantile of the TM control (TM count) are used in the scatterplot from which alpha is computed. The quantity alpha, is the slope of a line fitted to the scatterplot data. It will be appreciated that use of the $75^{th}$ quantile is exemplary and that it can be adjusted upwards (e.g., $85^{th}$ quantile) or downwards (e.g., $65^{th}$ quantile) in an application dependent matter. For instance, it can be treated as a hyperparameter that is optimized as part of the optimization of a downstream classifier. Moreover, rather than doing a quantile cut, other methods for removing outliers can be used instead, prior to using the scatterplot to compute alpha.

Moreover, the above approach requires calculation of the estimated noise rate at the given QMP genomic site i of the QMP ($x_{i,TMct}$) in the second dataset (which has the second state of the cancer condition (e.g., non-cancer). In some embodiments, $x_{i,TMct}$ is estimated as follows:

$\hat{x}_{i,TMNC}$ = estimated total abnormal counts in $TM$ second state, $\hat{x}_{i,TMNC} = x_{i,TMNC}/\text{bias}_i$, $$\text{beta} = \frac{75^{\text{th}} \text{ quantile } TM \text{ second state } (TM\ SS) \text{ not abnormal counts}}{75^{\text{th}} \text{ quantile } WGBS \text{ second state } (WGBS\ SS) \text{ not abnormal counts}},$$

$pc2$ = psuedocount to smooth noise estimate, $\hat{y}_{i,TMNC}$ = estimated reference (not abnormal) counts in $TM\ SS$, $\hat{y}_{i,TMNC} = \text{beta} * y_{i,WGBSNC}$, $\widehat{noise}_i$ = estimated site specific noise rate in cf$DNA$, and $\widehat{noise}_i = (\hat{x}_{i,TMNC} + pc2)/(\hat{x}_{i,TMNC} + \hat{y}_{i,TMNC} + 2 * pc2)$ To compute beta, the not abnormal counts at each site in a plurality of QMP genomic sites (under study) in one or more subjects that have the second cancer state are obtained ("WGBS second state (WGBS SS) not abnormal counts"). As such, there are a plurality of WGBS not abnormal counts, each for a different QMP genomic site obtained using the second dataset. Further, the not abnormal counts at each site in a plurality of QMP genomic sites from a targeted methylation sequencing are obtained ("TM second state (TM SS) not abnormal counts"). In typical embodiments the source of DNA for the TM second state is the same as for the WGBS control (and is typically from the subject that contribute to the second dataset and/or have the second cancer condition), the only difference being that, for the TM SS, the DNA is sequenced using targeted sequencing with the pull-down probes used in the TM rather than by WGBS. The quantity beta, in such embodiments, represents a slope of a line fitted to a scatterplot of "TM second state (TM SS) not abnormal counts"/"WGBS second state (WGBS SS) not abnormal counts." Each respective point in the scatterplot is for a different QMP genomic site j in the plurality of QMP genomic sites under study, where the x coordinate for the respective point is TM second state (TM SS) not abnormal counts at genomic site j and the y coordinate for respective point is WGBS SS (WGBS NC) not abnormal counts at genomic site j. Moreover, as indicated in the equation for beta, in typical embodiments only data from the $75^{th}$ quantile of the TM second state (TM SS) not abnormal counts and only data from the $75^{th}$ quantile of the WGBS second state (WGBS SS) not abnormal counts are used in the scatterplot from which beta is computed. The quantity beta is the slope of a line fitted to this scatterplot data. It will be appreciated that use of the $75^{th}$ quantile, as in the case of alpha, is exemplary and that it can be adjusted upwards (e.g., $85^{th}$ quantile) or downwards (e.g., $65^{th}$ quantile) in an application dependent matter. For instance, it can be treated as a hyperparameter that is optimized as part of the optimization of a downstream classifier. Moreover, rather than doing a quantile cut, other methods for removing outliers can be used instead, prior to using the scatterplot to compute beta.

In some embodiments, estimated depth $((\widehat{depth}_i))$ is calculated as:

$$\text{gamma} = \frac{75^{\text{th}} \text{ quantile } TM \text{ first state } (TM\ FS) \text{ not abnormal counts}}{75^{\text{th}} \text{ quantile } WGBS \text{ second state } (WGBS\ SS) \text{ not abnormal counts}},$$

$\hat{y}_i$ = not abnormal counts of site $i$ in cf$DNA$, $\hat{y}_i$ = gamma * $y_{i,WGBSNC}$, $\widehat{depth}_i$ = estimated depth of site $i$ in the cf$DNA$, and $\widehat{depth}_i = (\hat{y}_i + x_i/\text{bias}_i) * \text{bias}_i$.

To compute gamma, the not abnormal counts at each site in a plurality of QMP genomic sites (under study) in one or more subjects that have the second cancer state are obtained ("WGBS second state (WGBS SS) not abnormal counts"). As such, there are a plurality of WGBS not abnormal counts, each for a different QMP genomic site obtained using the second dataset. Further, the not abnormal counts at each site in a plurality of QMP genomic sites from a targeted methylation sequencing are obtained ("TM first state (TM FS) not abnormal counts"). In typical embodiments the source of DNA for the TM FS is from one or more subjects that contribute to the first dataset and/or have the first cancer condition. In typical embodiments the source of DNA for the WGBS SS is from one or more subjects that contribute to the second dataset and/or have the second cancer condition. The quantity gamma, in such embodiments, represents a slope of a line fitted to a scatterplot of "TM first state (TM FS) not abnormal counts"/"WGBS second state (WGBS SS) not abnormal counts." Each respective point in the scatterplot is for a different QMP genomic site j in the plurality of QMP genomic sites under study, where the x coordinate for the respective point is TM first state (TM FS) not abnormal counts at genomic site j and the y coordinate for respective point is WGBS second state (WGBS SS) not abnormal counts at genomic site j. Moreover, as indicated in the equation for gamma, in typical embodiments only data from the $75^{th}$ quantile of the TM first state (TM FS) not abnormal counts and only data from the $75^{th}$ quantile of the WGBS second state (WGBS SS) not abnormal counts are used in the scatterplot from which gamma is computed. The quantity gamma is the slope of a line fitted to this scatterplot data. It will be appreciated that use of the $75^{th}$ quantile, as in the case of alpha, is exemplary and that it can be adjusted upwards (e.g., $85^{th}$ quantile) or downwards (e.g., $65^{th}$ quantile) in an application dependent matter. For instance, it can be treated as a hyperparameter that is optimized as part of the optimization of a downstream classifier. Moreover, rather than doing a quantile cut, other methods for removing outliers can be used instead, prior to using the scatterplot to compute gamma.

In some embodiments, various noise or bias models can be generated to account for factors such as non-cancer noise rate, bias between assay types (e.g., WGBS vs TM): because, in a TM sequencing assay, abnormally methylated fragments are enriched by probes and hence tumor fraction computed based on QMPs within such fragments is likely biased. In some embodiments, the plurality of qualifying methylation patterns are filtered prior to tumor fraction estimation to include those with methylation patterns having 0% or 100% methylated CpG sites. In some alternative embodiments, the plurality of qualifying methylation patterns are filtered prior to tumor fraction estimation to include those that were effectively pulled down by a targeted methylation assay in control experiments with a mixture of 0% methylated and 100% methylated genomic DNA at predetermined compositions (e.g., 50/50 or 40/60 or 30/70 mixture of 0% and 100% methylated genomic DNAs). For example, mixtures of 50/50 of 0% and 100% methylated genomic DNAs can be subject to parallel WGBS and TM analysis to assess the effects of enrichment probes on perceived sequencing depth. In some alternative embodiments, the plurality of qualifying methylation patterns are filtered prior to tumor fraction estimation to include those that formed a non-overlapping set of qualifying methylation patterns, thereby mitigating double-counting.

In some such embodiments, the posterior tumor fraction estimates are further optimized and validated using synthetic dilutions. In some embodiments, the posterior tumor fraction estimates are further optimized using comparisons to estimates produced from matched samples (e.g., tumor fraction estimates from tumor biopsy WGBS samples are compared to tumor fraction estimates from patient-matched cfDNA WGBS samples).

Alternative methods and embodiments for calculation of tumor fraction estimates are described in detail in, e.g., United States Patent Publication No. 2020-0385813 A1, entitled "Systems and Methods for Estimating Cell Source Fractions Using Methylation Information," filed Dec. 18, 2019, which is hereby incorporated by reference, and in Example 4 below.

Monitoring Minimal Residual Disease and Other Applications.

In some embodiments, the state of cancer condition is tumor fraction, and the obtaining the third dataset and applying the fragment methylation patterns of the third dataset to the classifier is repeated on a recurring basis over time. For example, in some embodiments, the applying on a recurring basis is performed for minimal residual disease and recurrence monitoring. In some such embodiments, the obtaining and applying using the third dataset is performed before and after a cancer treatment to assess the efficacy of the cancer treatment (e.g., where the third dataset is obtained from a biological sample from a test subject before and after a cancer treatment).

In some such embodiments, the determination of tumor fraction is performed from a first sample obtained before and a second sample obtained after a cancer treatment to assess the efficacy of the cancer treatment for a subject.

In some embodiments, the method repeats the estimating the tumor fraction estimate for a test subject at each respective time point in a plurality of time points across an epoch, thus obtaining a corresponding tumor fraction estimate, in a plurality of tumor fraction estimates, for the test subject at each respective time point. In some embodiments this plurality of tumor fraction estimates is used to determine a state or progression of a disease condition in the test subject during the epoch in the form of an increase or decrease of tumor fraction over the epoch.

In some embodiments, each epoch is a period of months and each time point in the plurality of time points is a different time point in the period of months. In some embodiments, the period of months is less than four months. In some embodiments, each epoch is one month long. In some embodiments, each epoch is two months long. In some embodiments, each epoch is three months long. In some embodiments, each epoch is four months long. In some embodiments, each epoch is five, six, seven, eight, nine, ten, eleven, twelve, thirteen, fourteen, fifteen, sixteen, seventeen, eighteen, nineteen, twenty, twenty-one, twenty-two, twenty-three or twenty-four months long.

In some embodiments, the epoch is a period of years and each time point in the plurality of time points is a different time point in the period of years. In some embodiments, the period of years is between one year and ten years. In some embodiments, the period of years is one year, two years, three years, four years, five years, six years, seven years, eight years, nine years, or ten years. In some embodiments the epoch is between one and thirty years. In some embodiments, the epoch is a period of hours and each time point in the plurality of time points is a different time point in the period of hours. In some embodiments, the period of hours is between one hour and twenty-four hours. In some embodiments, the period of hours is 1, 2, 3, 4, 5, 6, 7, 8, 9, 10, 11, 12, 13, 14, 15, 16, 17, 18, 19, 20, 21, 22, 23, or 24 hours.

In some embodiments, the method further comprises changing a diagnosis of the test subject when the tumor fraction estimate (or clonal expansion estimate) of the subject is observed to change by a threshold amount across the epoch. For instance, in some embodiments, the diagnosis is changed from having cancer to being in remission.

As another example, in some embodiments, the diagnosis is changed from not having cancer to having cancer. As another example, in some embodiments, the diagnosis is changed from having a first stage of a cancer to having a second stage of a cancer. As another example, in some embodiments, the diagnosis is changed from having a second stage of a cancer to having a third stage of a cancer. As still another example, in some embodiments, the diagnosis is changed from having a third stage of a cancer to having a fourth stage of a cancer. As still another example, in some embodiments, the diagnosis is changed from having a cancer that has not metastasized to having a cancer that has metastasized.

In some embodiments, a prognosis of the test subject is changed when the tumor fraction estimate of the subject is observed to change by a threshold amount across the epoch. For example, in some embodiments, the prognosis involves life expectancy and the prognosis is changed from a first life expectancy to a second life expectancy, where the first and second life expectancy differ in their duration in some embodiments. In some embodiments, the change in prognosis increases the life expectancy of the subject. In some embodiments, the change in prognosis decreases the life expectancy of the subject.

In some embodiments, a treatment of the test subject is changed when the tumor fraction estimate of the subject is observed to change by a threshold amount across the epoch. In some embodiments, the changing of the treatment comprises initiating a cancer medication, increasing the dosage of a cancer medication, stopping a cancer medication, or decreasing the dosage of the cancer medication. In some embodiments, the changing of the treatment comprises initiating or terminating treatment of the subject with Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof. In some embodiments, the changing of the treatment comprises increasing or decreasing a dosage of Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof administered to the subject. In some embodiments, the threshold is greater than ten percent, greater than twenty percent, greater than thirty percent, greater than forty percent, greater than fifty percent, greater than two-fold, greater than three-fold, or greater than five-fold.

In some embodiments, the tumor fraction estimate for the test subject is between 0.003 and 1.0. In some embodiments, the tumor fraction estimate for the test subject is between 0.005 and 0.80. In some embodiments, the tumor fraction estimate for the test subject is between 0.01 and 0.70. In some embodiments, the tumor fraction estimate for the test subject is between 0.05 and 0.60.

In some embodiments, the method further comprises applying a treatment regimen to the test subject based at least in part, on a value of the tumor fraction estimate (or clonal expansion estimate) for the test subject. In some embodiments, the treatment regimen comprises applying an agent for cancer to the test subject. In some embodiments, the agent for cancer is a hormone, an immune therapy, radiography, or a cancer drug. In some embodiments, the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof.

In some embodiments, the test subject has been treated with an agent for cancer and the method further comprises using the tumor fraction estimate for the test subject to evaluate a response of the subject to the agent for cancer. In some embodiments, the agent for cancer is a hormone, an immune therapy, radiography, or a cancer drug. In some embodiments, the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof.

In some embodiments, the test subject has been treated with an agent for cancer and the tumor fraction estimate for the test subject is used to determine whether to intensify or discontinue the agent for cancer in the test subject. For instance, in some embodiments, observation of at least a tumor fraction estimate (e.g., greater than 0.05, 0.10, 0.15, 0.20, 0.25, or 0.30, etc.) is used as a basis for intensifying (e.g., increasing the dosage, increasing radiation level in radiation treatment) of the agent for cancer in the test subject. In some embodiments, observation of less than a threshold tumor fraction estimate (e.g., less than 0.05, 0.10, 0.15, 0.20, 0.25, or 0.30, etc.) is used as a basis for discontinuing use of the agent for cancer in the test subject.

In some embodiments, the test subject has been subjected to a surgical intervention to address the cancer and the method further comprises using the tumor fraction estimate for the test subject to evaluate a condition of the test subject in response to the surgical intervention. In some embodiments the condition is a metric based upon the tumor fraction estimate using the methods provided in the present disclosure.

In some embodiments, methylation patterns discriminating or indicating a cancer condition are used to label fragments obtained from cfDNA. For example, in some such embodiments, one or more fragments comprising one or more methylation patterns matching the identified methylation patterns associated with a cancer condition (e.g., a tumor) are isolated and examined for other characterizing features. In some such embodiments, investigation of such alternative features can provide additional uses, such as further insight into characteristics that define and/or are associated with tumor-derived nucleic acid fragments.

In some embodiments, the accuracy of a tumor fraction estimate is validated using one or more synthetic dilutions. For example, in some embodiments, a sample comprising a high tumor fraction is synthetically diluted into non-cancer cfDNA. A tumor fraction estimate is calculated for each sequential dilution and compared with the expected tumor fraction estimate for concordance.

In some embodiments, dilutions are performed by diluting cancer signals (e.g., sequencing read-out data) into non-cancer signals in silico. In some embodiments, wet-lab dilutions are performed by diluting cancer cfDNA samples into non-cancer cfDNA samples. In some embodiments, dilutions are performed by diluting cancer cfDNA samples from a first test subject into non-cancer cfDNA from a second test subject prior to sequencing.

In some embodiments, dilutions are performed using pooled test subjects. In some embodiments, dilutions are performed by diluting samples obtained from a first cancer condition (e.g., cancer/non-cancer, cancer type/subtype, stage, and/or tissue-of-origin) into samples obtained from a second cancer condition that is different from the first cancer condition.

In some embodiments, validation by synthetic dilution of tumor fraction estimates (e.g., calculated using methylation patterns) can be performed to assess classifier performance and/or to probe the behavior of the classifier.

Other Aspects of the Disclosure

Another aspect of the present disclosure provides a computer system for identifying a plurality of methylation patterns that discriminate or indicate a cancer condition. In this aspect, the computer system comprises at least one processor and a memory storing at least one program for execution by the at least one processor. In some embodiments, the at least one program comprises instructions for performing any of the methods and embodiments described herein and/or any combinations or alternatives thereof as will be apparent to one skilled in the art.

Another aspect of the present disclosure provides a non-transitory computer-readable storage medium storing program code instructions that, when executed by a processor, cause the processor to perform a method for identifying a plurality of methylation patterns that discriminate or indicate a cancer condition. In some embodiments, the program code instructions cause the processor to perform any of the methods and embodiments described herein and/or any combinations or alternatives thereof as will be apparent to one skilled in the art.

EXAMPLES

Example 1—the Cell-Free Genome Atlas Study (CCGA)

Subjects from the CCGA [NCT02889978] were used in the Examples of the present disclosure.

CCGA is a prospective, multi-center, observational cfDNA-based early cancer detection study that has enrolled 15,254 demographically-balanced participants at 141 sites. Blood samples were collected from the 15,254 enrolled participants (56% cancer, 44% non-cancer) from subjects with newly diagnosed therapy-naive cancer (C, case) and participants without a diagnosis of cancer (noncancer [NC], control) as defined at enrollment.

In a first cohort (pre-specified substudy) (CCGA1), plasma cfDNA extractions were obtained from 3,583 CCGA and STRIVE participants (CCGA: 1,530 cancer participants and 884 non-cancer participants; STRIVE 1,169 non-cancer participants). STRIVE is a multi-center, prospective, cohort study enrolling women undergoing screening mammography (99,259 participants enrolled). Blood was collected (n=1,785) from 984 CCGA participants with newly diagnosed, untreated cancer (20 tumor types, all stages) and 749 participants with no cancer diagnosis (controls) for plasma cfDNA extraction. This preplanned substudy included 878 cases, 580 controls, and 169 assay controls (n=1627) across twenty tumor types and all clinical stages.

Three sequencing assays were performed on the blood drawn from each participant: 1) paired cfDNA and white blood cell (WBC)—targeted sequencing (60,000×, 507 gene panel) for single nucleotide variants/indels (the ART sequencing assay); a joint caller removed WBC-derived somatic variants and residual technical noise; 2) paired cfDNA and WBC whole-genome sequencing (WGS; 35×) for copy number variation; a novel machine learning algorithm generated cancer-related signal scores; joint analysis identified shared events; and 3) cfDNA whole-genome bisulfite sequencing (WGBS; 34×) for methylation; normalized scores were generated using abnormally methylated fragments. In addition, tissue samples were obtained from participants with cancer only, such that 4) whole-genome sequencing (WGS; 30×) was performed on paired tumor and WBC gDNA for identification of tumor variants for comparison.

Within the context of the CCGA-1 study, several methods were developed for estimating tumor fraction of a cfDNA sample. See, International Patent Publication No. WO/2019/204360, entitled "SYSTEMS AND METHODS FOR DETERMINING TUMOR FRACTION IN CELL-FREE NUCLEIC ACID"; International Patent Publication No. WO 2020/132148, entitled "SYSTEMS AND METHODS FOR ESTIMATING CELL SOURCE FRACTIONS USING METHYLATION INFORMATION"; and United States Patent Publication Number US 2020-0340064 A1, entitled "SYSTEMS AND METHODS FOR TUMOR FRACTION ESTIMATION FROM SMALL VARIANTS" each of which is hereby incorporated by reference. For example, one of the approaches was illustrated as method 1300 in FIG. 13A. In this approach, nucleic acid samples from formalin-fixed, paraffin-embedded (FFPE) tumor tissues (e.g., 1304) and nucleic acid samples from white blood cells (WBC) from the matching patient (e.g., 1306) were sequenced by whole-genome sequencing (WGS). Somatic variants identified based on the sequencing data (e.g., 1308) were analyzed against matching cfDNA sequencing data from the same patient (e.g., 1310) were used to determine a tumor fraction estimate (e.g., 1312).

In a second pre-specified substudy (CCGA-2), a targeted, rather than whole-genome, bisulfite sequencing assay was used to develop a classifier of cancer versus non-cancer and tissue-of-origin based on a targeted methylation (TM) sequencing approach. For CCGA2, 3,133 training participants and 1,354 validation samples (775 having cancer; 579 not having cancer as determined at enrollment, prior to confirmation of cancer versus non-cancer status) were used. Plasma cfDNA was subjected to a bisulfite sequencing assay (the COMPASS assay) targeting the most informative regions of the methylome, as identified from a unique methylation database and prior prototype whole-genome and targeted sequencing assays, to identify cancer and tissue-defining methylation signal. Of the original 3,133 samples reserved for training, only 1,308 samples were deemed clinically evaluable and analyzable. Analysis was performed on a primary analysis population n=927 (654 cancer and 273 non-cancer) and a secondary analysis population n=1,027 (659 cancer and 373 non-cancer). Finally, genomic DNA from formalin-fixed, paraffin-embedded (FFPE) tumor tissues and isolated cells from tumors was subjected to whole-genome bisulfite sequencing (WGBS) to generate a large database of cancer-defining methylation signals for use in panel design and in training to optimize performance.

See, e.g., Klein et al., 2018, "Development of a comprehensive cell-free DNA (cfDNA) assay for early detection of multiple tumor types: The Circulating Cell-free Genome Atlas (CCGA) study," J. Clin. Oncology 36 (15), 12021-12021, and Liu et al., 2019, "Genome-wide cell-free DNA (cfDNA) methylation signatures and effect on tissue of origin (TOO) performance," J. Clin. Oncology 37 (15), 3049-3049, each of which is hereby incorporated herein by reference in its entirety.

Example 2—Obtaining a Plurality of Sequence Reads

FIG. 7 is a flowchart of method 700 for preparing a nucleic acid sample for sequencing according to one embodiment. The method 700 includes, but is not limited to, the following steps. For example, any step of method 700 may comprise a quantitation sub-step for quality control or other laboratory assay procedures known to one skilled in the art.

In block 702, a nucleic acid sample (DNA or RNA) is extracted from a subject. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has a cancer or disease, ctDNA in an extracted sample may be present at a detectable level for diagnosis.

In block 704, a sequencing library is prepared. During library preparation, unique molecular identifiers (UMI) are added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment. This provides a way to identify sequence reads that came from the same original fragment in downstream analysis.

In block 706, targeted DNA sequences are enriched from the library. During enrichment, hybridization probes (also referred to herein as "probes") are used to target and pull down nucleic acid fragments informative for the presence or absence of cancer (or disease), cancer status, or a cancer classification (e.g., cancer class or tissue of origin). For a given workflow, the probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. In one embodiment, the probes are designed based on a methylation site panel. In one embodiment, the probes are designed based on a panel of targeted genes to analyze particular mutations or target regions of the genome (e.g., of the human or another organism) that are suspected to correspond to certain cancers or other types of diseases. Moreover, the probes may cover overlapping portions of a target region. In Block 708, these probes are used to general sequence reads of the nucleic acid sample.

Figure 8:
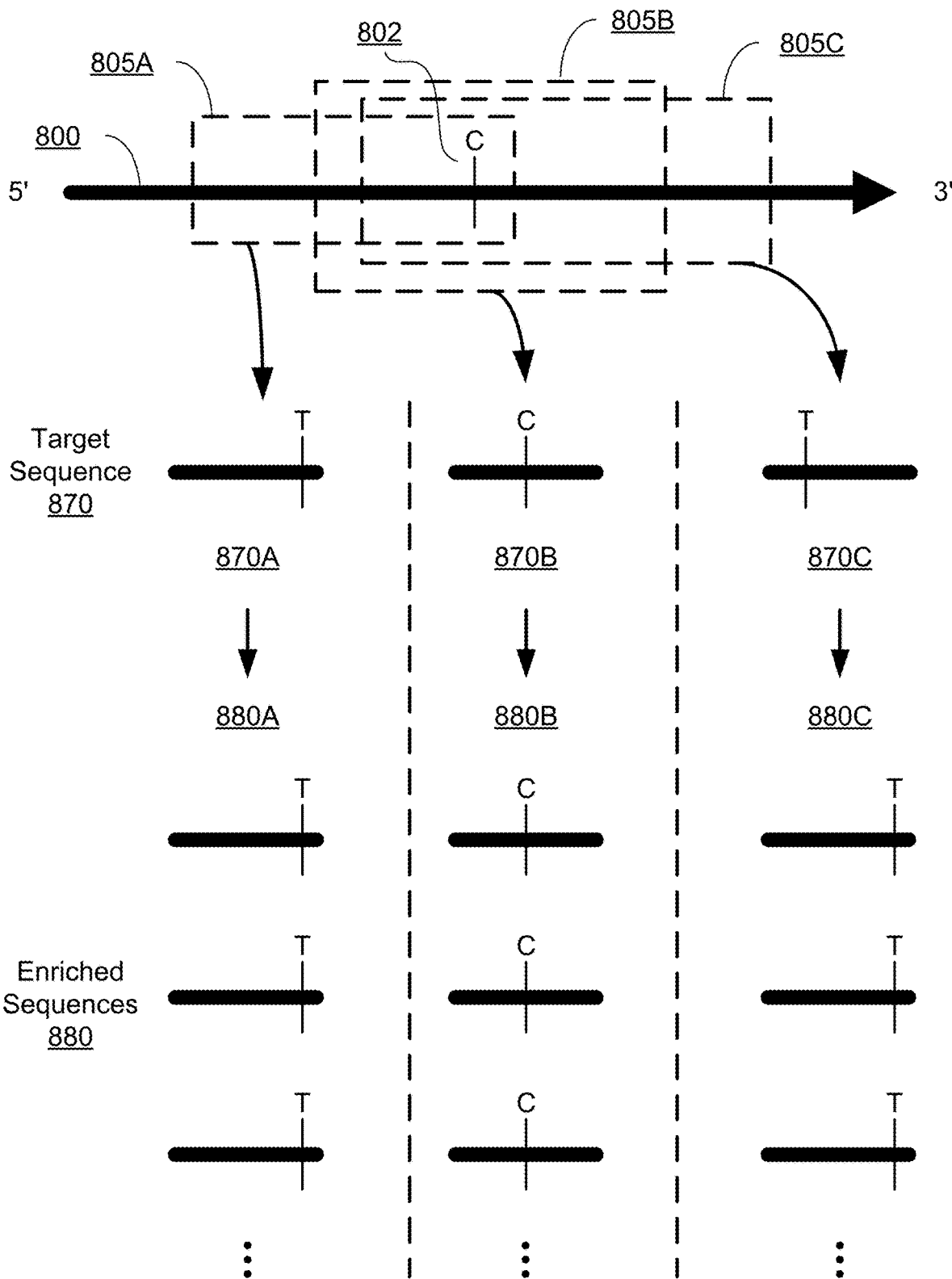
FIG. 8 illustrates a graphical representation of the process for obtaining nucleic acid fragments in accordance with some embodiments of the present disclosure.
Figure 10A:
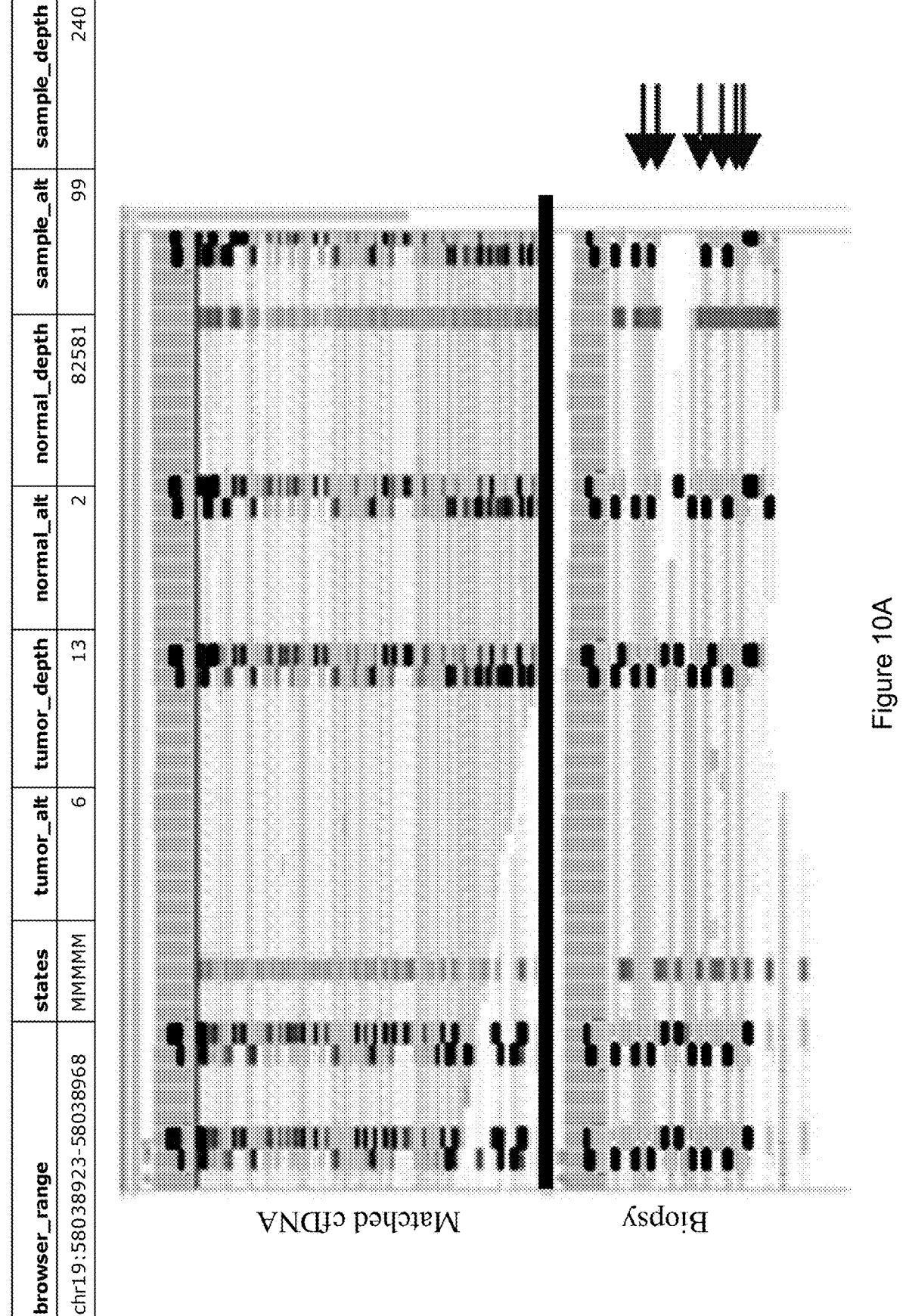
FIGS. 10A, 10B, 10C, 10D, and 10E illustrate visualizations of methylation states at CpG sites in selected intervals for non-cancer cfDNA samples, tumor biopsy samples, and matched cfDNA samples using an Integrative Genomics Viewer (IGV), in accordance with some embodiments of the present disclosure.
Figure 10B:
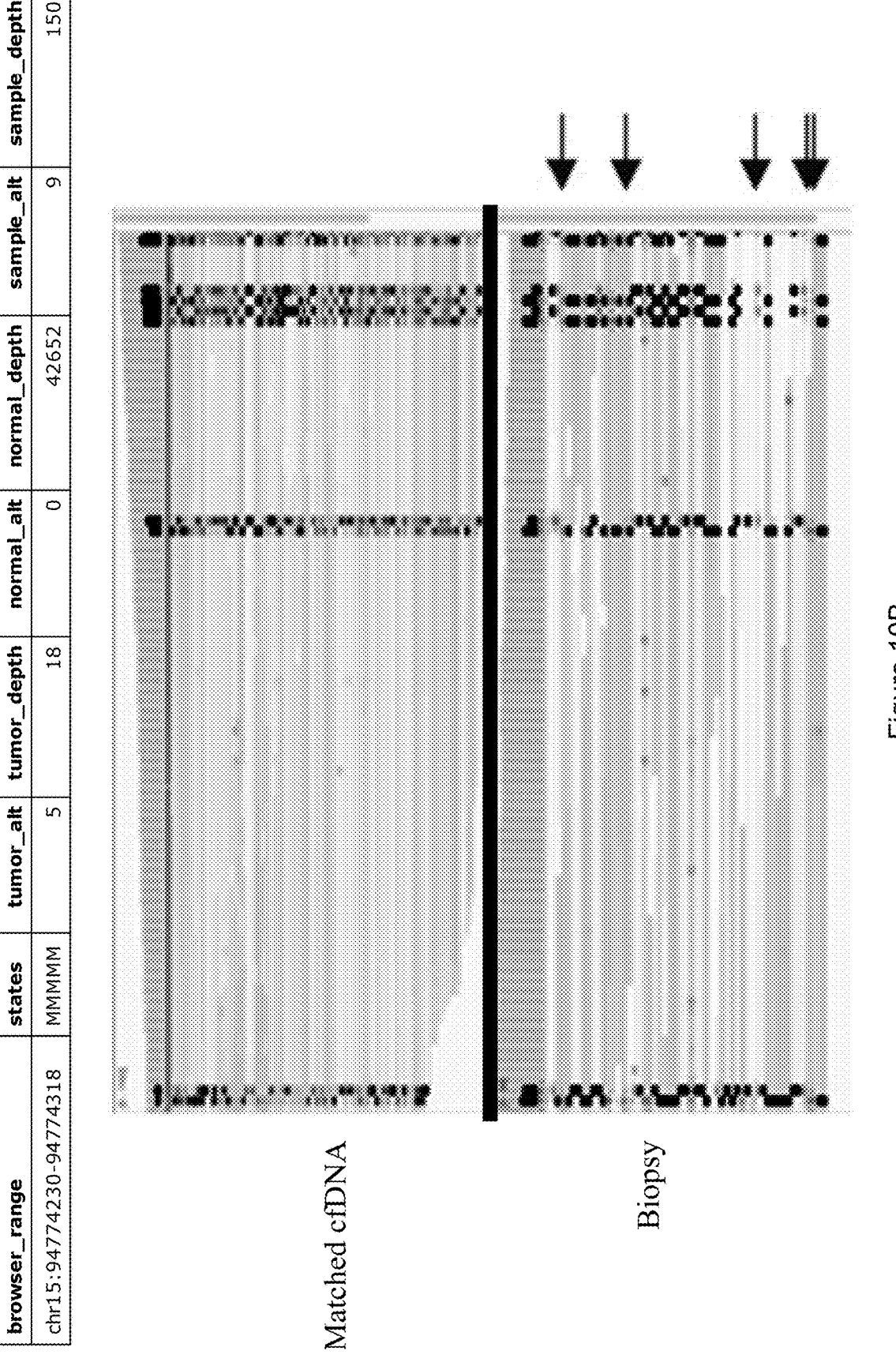
Figure 10C:
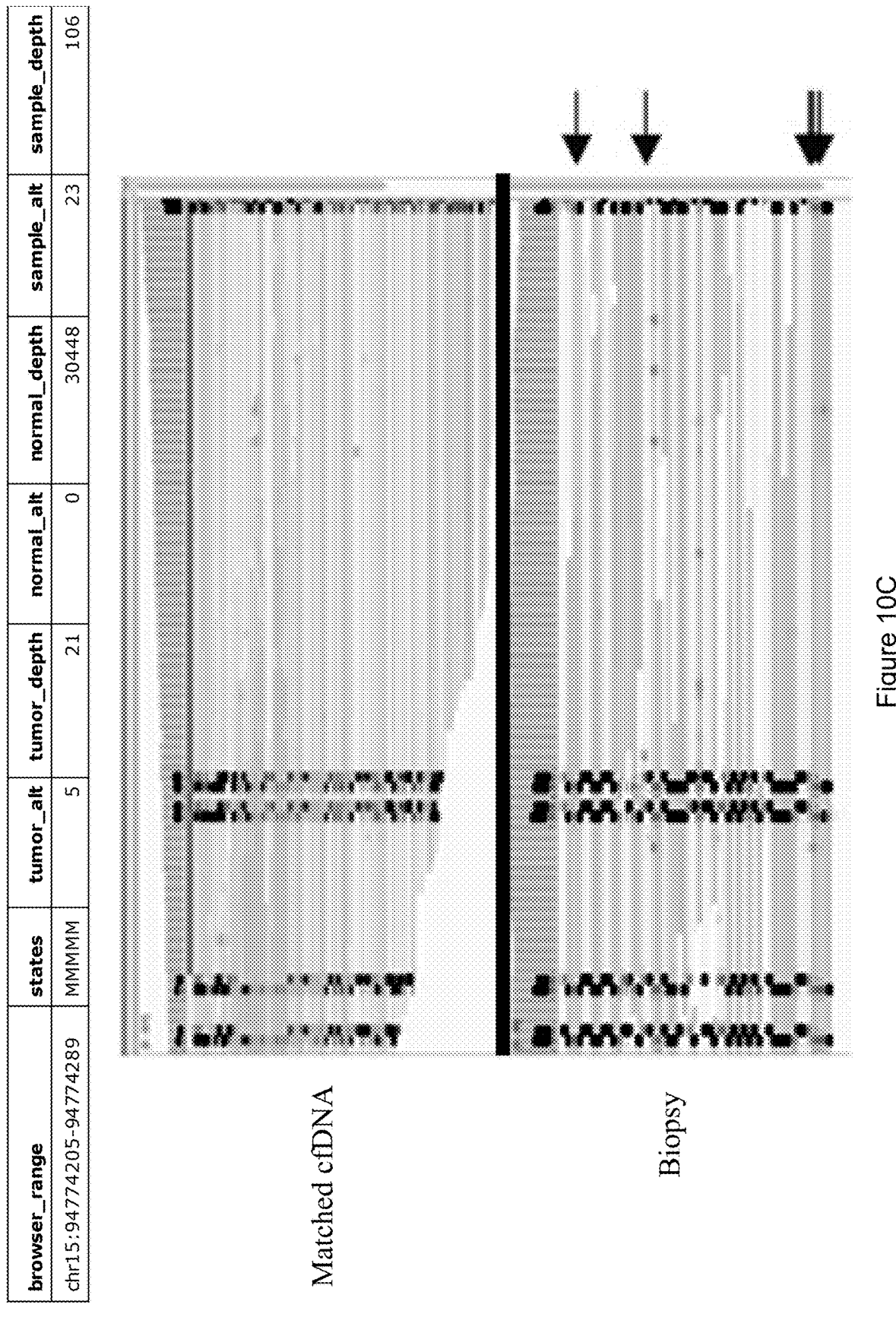
Figure 10D:
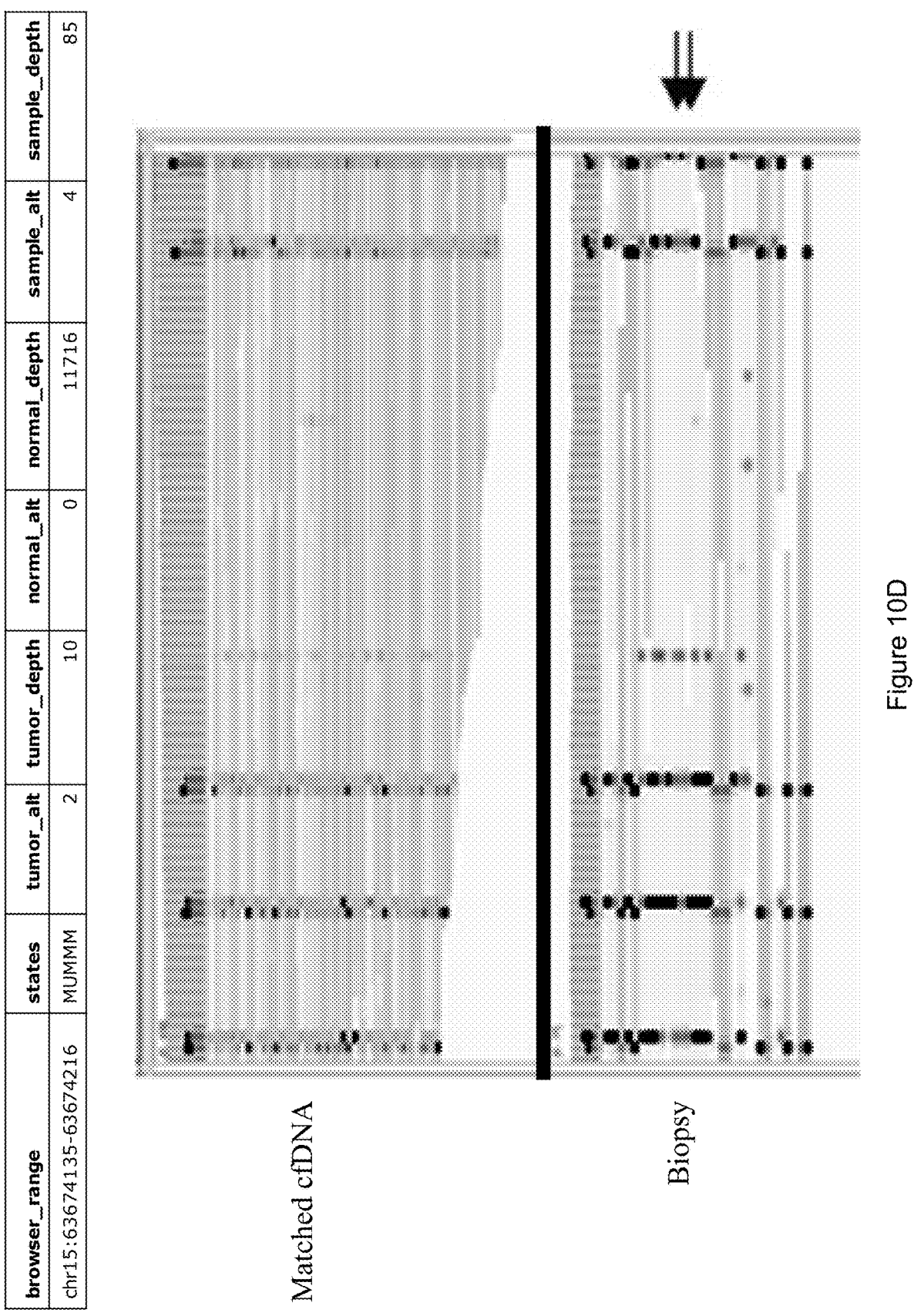
Figure 10E:
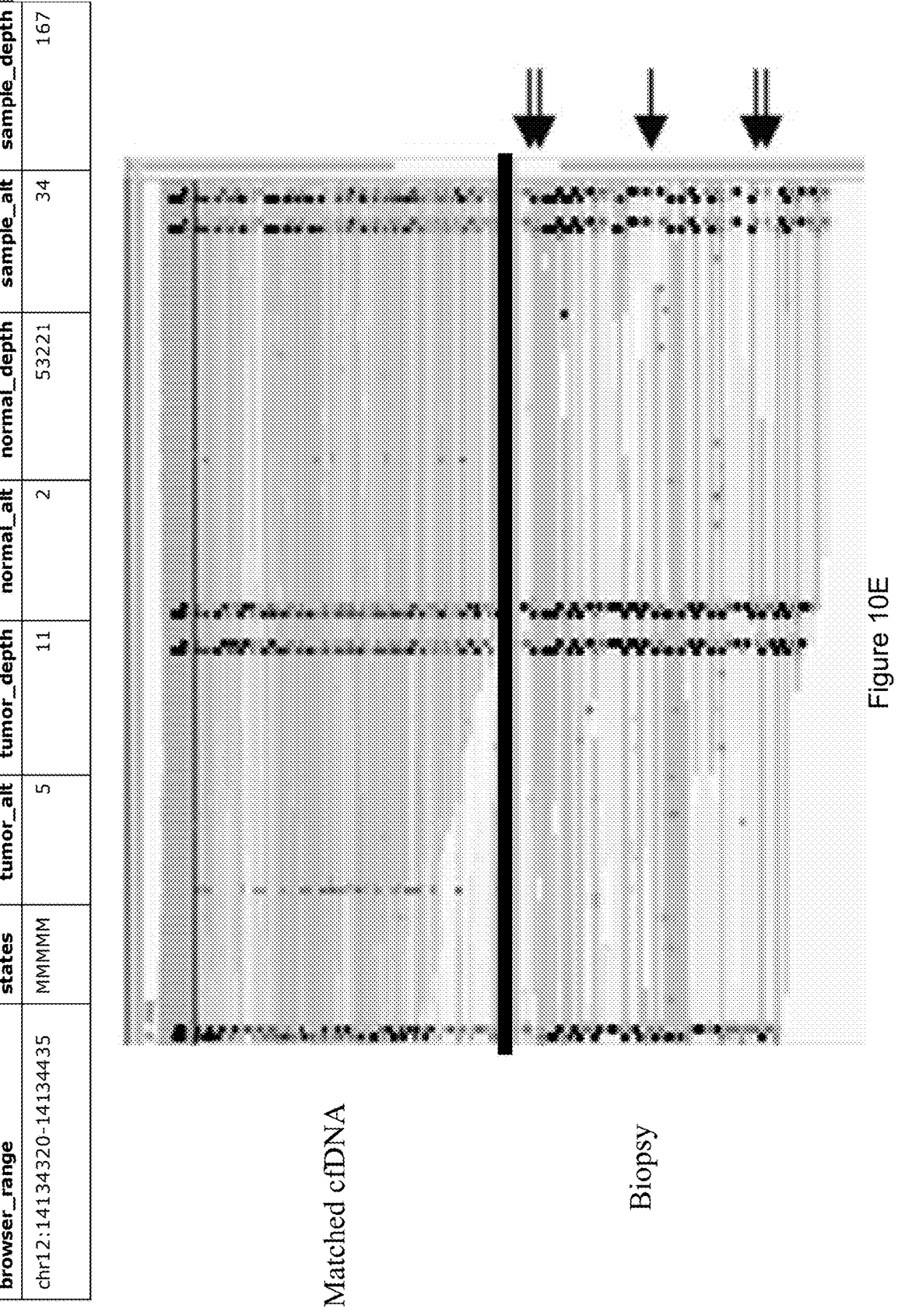

FIG. 8 is a graphical representation of the process for obtaining sequence reads according to one embodiment. FIG. 8 depicts one example of a nucleic acid segment 800 from the sample. The nucleic acid segment 800 can be a single-stranded nucleic acid segment. In some embodiments, the nucleic acid segment 800 is a double-stranded cfDNA segment. The illustrated example depicts three regions 805A, 805B, and 805C of the nucleic acid segment that can be targeted by different probes. Specifically, each of the three regions 805A, 805B, and 805C includes an overlapping position on the nucleic acid segment 800. An example overlapping position is depicted in FIG. 8 as the cytosine ("C") nucleotide base 802. The cytosine nucleotide base 802 is located near a first edge of region 805A, at the center of region 805B, and near a second edge of region 805C.

In some embodiments, one or more (or all) of the probes are designed based on a gene panel or methylation site panel to analyze particular mutations or target regions of the genome (e.g., of the human or another organism) that are suspected to correspond to certain cancers or other types of diseases. By using a targeted gene panel or methylation site panel rather than sequencing all expressed genes of a genome, also known as "whole-exome sequencing," the method 800 may be used to increase sequencing depth of the target regions, where depth refers to the count of the number of times a given target sequence within the sample has been sequenced. Increasing sequencing depth reduces the required input amounts of the nucleic acid sample.

Hybridization of the nucleic acid sample 800 using one or more probes results in an understanding of a target sequence 870. As shown in FIG. 8, the target sequence 870 is the nucleotide base sequence of the region 805 that is targeted by a hybridization probe. The target sequence 870 can also be referred to as a hybridized nucleic acid fragment. For example, target sequence 870A corresponds to region 805A targeted by a first hybridization probe, target sequence 870B corresponds to region 805B targeted by a second hybridization probe, and target sequence 870C corresponds to region 805C targeted by a third hybridization probe. Given that the cytosine nucleotide base 802 is located at different locations within each region 805A-C targeted by a hybridization probe, each target sequence 870 includes a nucleotide base that corresponds to the cytosine nucleotide base 802 at a particular location on the target sequence 870.

After a hybridization step, the hybridized nucleic acid fragments are captured and may also be amplified using PCR. For example, the target sequences 870 can be enriched to obtain enriched sequences 880 that can be subsequently sequenced. In some embodiments, each enriched sequence 880 is replicated from a target sequence 870. Enriched sequences 880A and 880C that are amplified from target sequences 870A and 870C, respectively, also include the thymine nucleotide base located near the edge of each sequence read 880A or 880C. As used hereafter, the mutated nucleotide base (e.g., thymine nucleotide base) in the enriched sequence 880 that is mutated in relation to the reference allele (e.g., cytosine nucleotide base 802) is considered as the alternative allele. Additionally, each enriched sequence 880B amplified from target sequence 870B includes the cytosine nucleotide base located near or at the center of each enriched sequence 880B.

In Block 708, sequence reads are generated from the enriched DNA sequences, e.g., enriched sequences 880 shown in FIG. 8. Sequencing data may be acquired from the enriched DNA sequences by known means in the art. For example, the method 800 may include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLID sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome can represent the likely location within the reference genome to which the nucleic acid fragment corresponds. An output file having SAM (sequence alignment map) format or BAM (binary) format may be generated and output for further analysis such as methylation state determination.

Example 3—Generation of Methylation State Vector

FIG. 9 is a flowchart describing a process 900 of sequencing a fragment of cfDNA to obtain a methylation state vector, according to an embodiment in accordance with the present disclosure.

Referring to step 902, the cfDNA fragments are obtained from the biological sample (e.g., as discussed above in conjunction with Example 2). Referring to step 920, the cfDNA fragments are treated to convert unmethylated cytosines to uracils. In one embodiment, the DNA is subjected to a bisulfite treatment that converts the unmethylated cytosines of the fragment of cfDNA to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA))

is used for the bisulfite conversion in some embodiments. In other embodiments, the conversion of unmethylated cytosines to uracils is accomplished using an enzymatic reaction. For example, the conversion can use a commercially available kit for converting unmethylated cytosines to uracils, such as APOBEC-Seq (NEBiolabs, Ipswich, MA).

From the converted cfDNA fragments, a sequencing library is prepared (step 930). Optionally, the sequencing library is enriched 935 for cfDNA fragments, or genomic regions, that are informative for cancer status using a plurality of hybridization probes. The hybridization probes are short oligonucleotides capable of hybridizing to particularly specified cfDNA fragments, or targeted regions, and enriching for those fragments or regions for subsequent sequencing and analysis. Hybridization probes may be used to perform a targeted, high-depth analysis of a set of specified CpG sites of interest to the researcher. Once prepared, the sequencing library or a portion thereof can be sequenced to obtain a plurality of sequence reads (940). The sequence reads may be in a computer-readable, digital format for processing and interpretation by computer software.

From the sequence reads, a location and methylation state for each CpG site is determined based on the alignment of the sequence reads to a reference genome (950). A methylation state vector for each fragment specifying a location of the fragment in the reference genome (e.g., as specified by the position of the first CpG site in each fragment, or another similar metric), a number of CpG sites in the fragment, and the methylation state of each CpG site in the fragment (960).

For details regarding WGBS, see, e.g., United States Patent Publication No. US 2019-0287652 A1, entitled "Anomalous Fragment Detection and Classification," and United States Patent Publication No. 2020-0385813 A1, entitled "Systems and Methods for Estimating Cell Source Fractions Using Methylation Information," each of which is hereby incorporated by reference.

Example 4—Test Case with High Tumor Fraction

A test case was obtained from the CCGA study using a sample with high tumor fraction (targeted sequencing (ART) estimated tumor fraction: 15%; participant ID 2737). For proof-of-concept purposes, the high tumor fraction provided a relatively high number of nucleic acid fragments in both tissue (e.g., tumor) samples and cfDNA samples that were tumor-derived. In addition, the test case comprised targeted methylation data from cfDNA. The control non-cancer dataset was selected from CCGA data using all fragments classified as non-cancer with a specificity threshold of 99%. See, Liu et al., 2019, "Genome-wide cell-free DNA (cfDNA) methylation signatures and effect on tissue of origin (TOO) performance," J. Clin. Oncology 37 (15), 3049-3049, which is hereby incorporated herein by reference in its entirety. Fragments were filtered for minimum mapping quality (MAPQ), as well as for duplicate, uncalled, and unconverted fragments. Fragments were not p-value filtered. Identification of differential methylation state intervals was performed for tumor samples from participant 2737 and the control non-cancer dataset, using an exemplary embodiment of the disclosed method with the following parameters: minimum depth of coverage for tumor samples=10, minimum variant allele fraction (VAF) of tumor samples=0.2, minimum depth of coverage for non-cancer sample=0, maximum VAF of non-cancer sample=0.001, number of CpGs in the interval=5. As disclosed herein, the VAF can refer to a fraction of one or more qualifying methylation patterns (QMPs) over the total number of fragment methylation patterns observed at the corresponding locus (or loci) for the qualifying methylation patterns.

Characteristics of Differential Methylation State Intervals.

Figure 3:
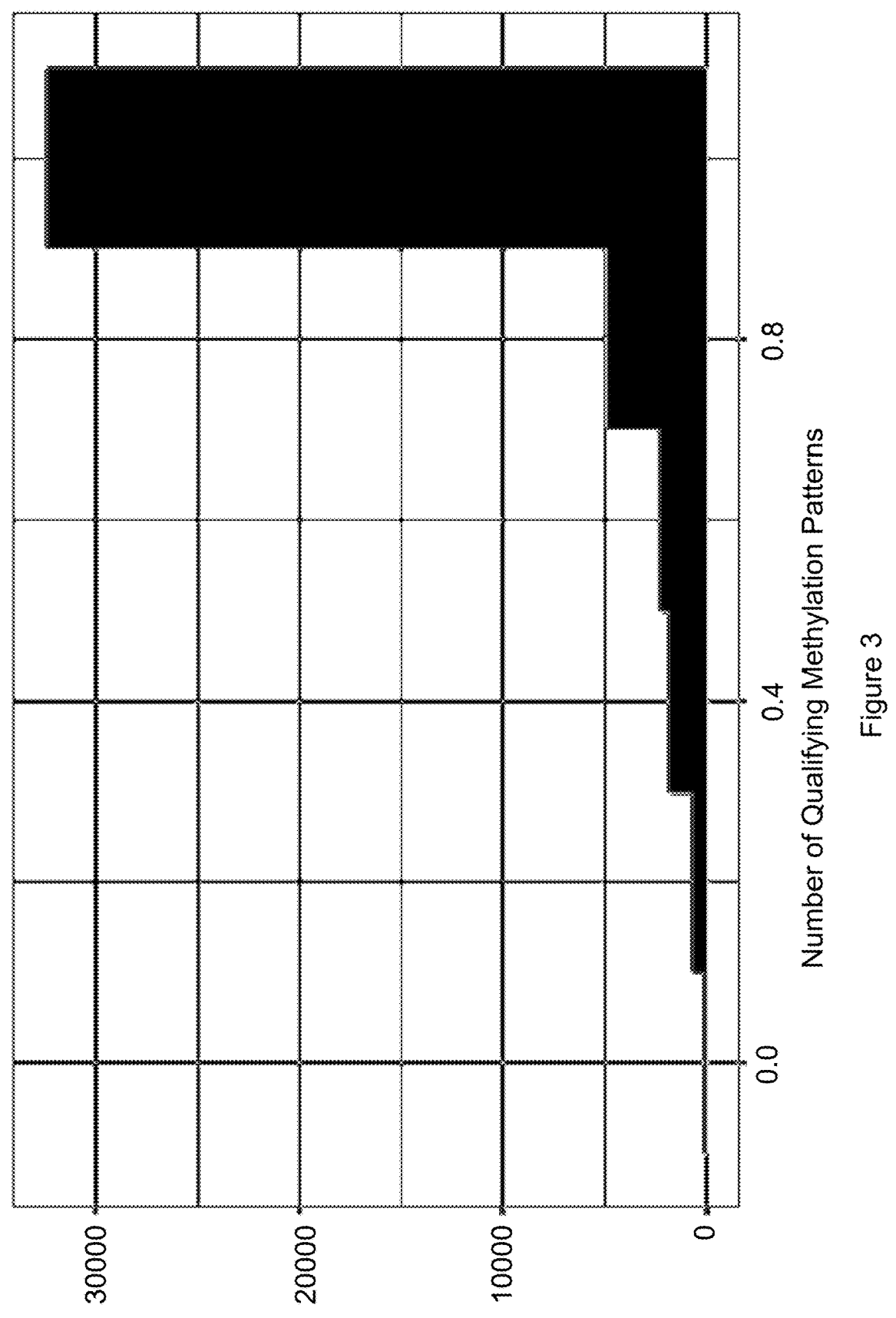
FIG. 3 illustrates a plot showing the number of fragment methylation patterns (e.g., those containing 5 CpG sites) versus the extent of a particular fragment methylation pattern for a single example participant in accordance with some embodiments of the present disclosure.

Possible qualifying methylation patterns (QMP) based on sequencing data obtained from the high tumor fraction test case sample was evaluated based on the extent at which each possible qualifying methylation pattern was methylated (FIG. 3). Here, the possible QMPs are defined as sequences of methylation state for five contiguous CpG sites that are supported by methylation sequencing data of the test case sample. The figure shows that there are few possible QMPs with low methylation fractions (e.g., the majority of possible QMPs in the test case are highly methylated), highlighting the high potential functionality of methylation patterns for the identification of QMPs.

Figure 4:
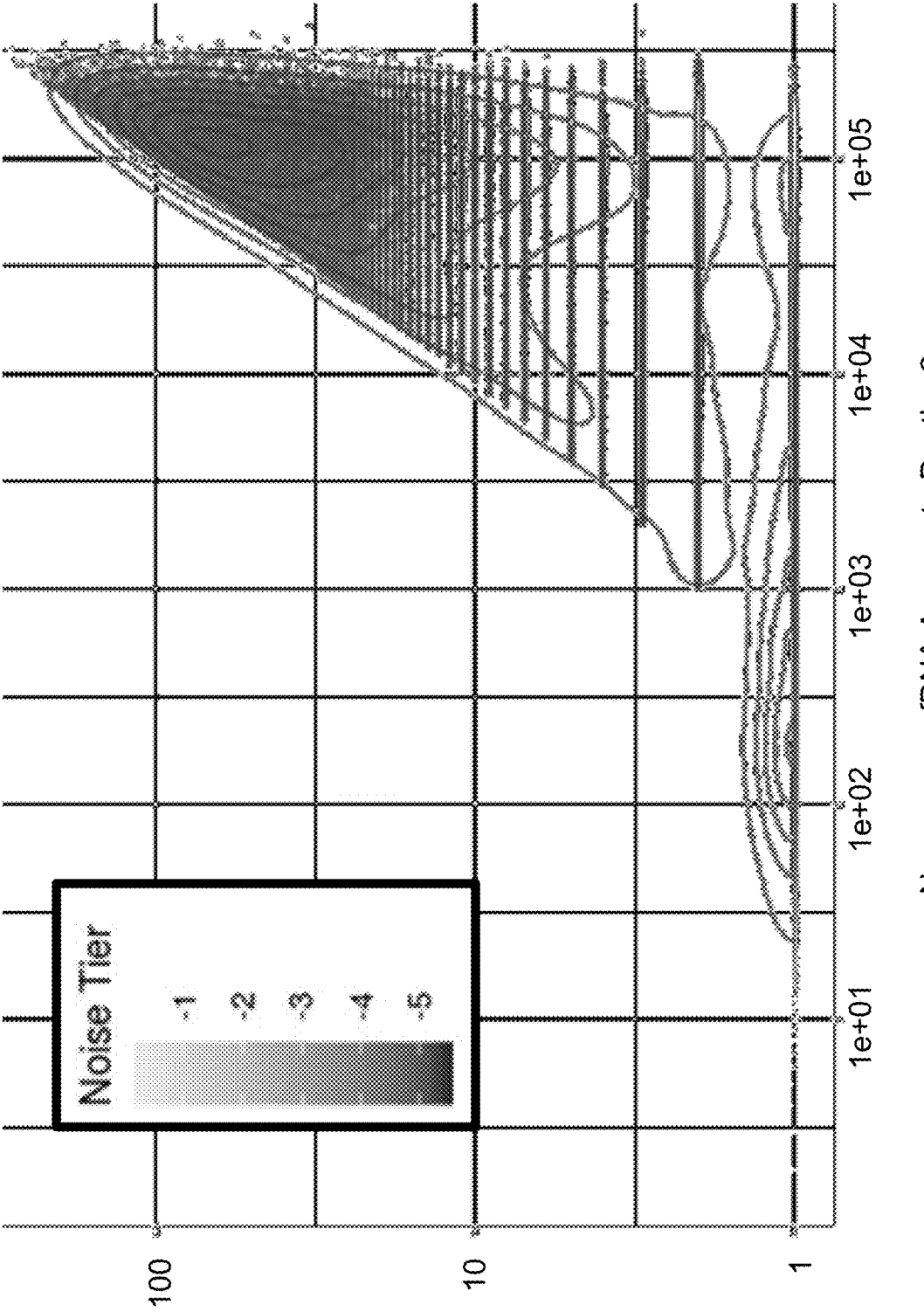
FIG. 4 illustrates a density plot of noise levels at a plurality of methylation sites as a function of non-cancer cfDNA aggregate alt counts (variant counts)+1 versus non-cancer cfDNA aggregate depth+2 in accordance with some embodiments of the present disclosure.

The non-cancer sample was assessed to identify suitable intervals (e.g., comprising 5 CpG sites) for further analysis. For example, FIG. 4 illustrates a density plot of all intervals included in non-cancer nucleic acid fragments derived from cfDNA, from a non-cancer subject showing aggregate QMP counts ("Non-cancer cfDNA Aggregate Alt Count+1") against the depth of coverage ("Non-cancer cfDNA Aggregate Depth+2") at each respective candidate interval. Density shows the number of intervals at each region of intersection between variant count and depth of coverage, while the level of noise at each candidate interval is represented by the color legend (e.g., light gray: high noise; black: low noise). Noise is calculated as a frequency based on the control non-cancer dataset, using the formula: $\text{Noise}=(\text{alt\_counts}+1)/(\text{depth\_coverage}+2)$, where "alt_counts" is the number of fragments that have a variant methylation pattern at the interval, and "depth_coverage" is the number of fragments that cover the interval. Using the parameters for identification of differential methylation patterns defined above, preferred intervals for further analysis in the test case include those having high depth values and low alt (variant) count values. For example, for intervals with high stability in the control condition, variation in the test condition will be readily apparent (x: cpg spans the QMP sites and y represents the fragments that contain the patterns matching the final QMPs).

Figure 5:
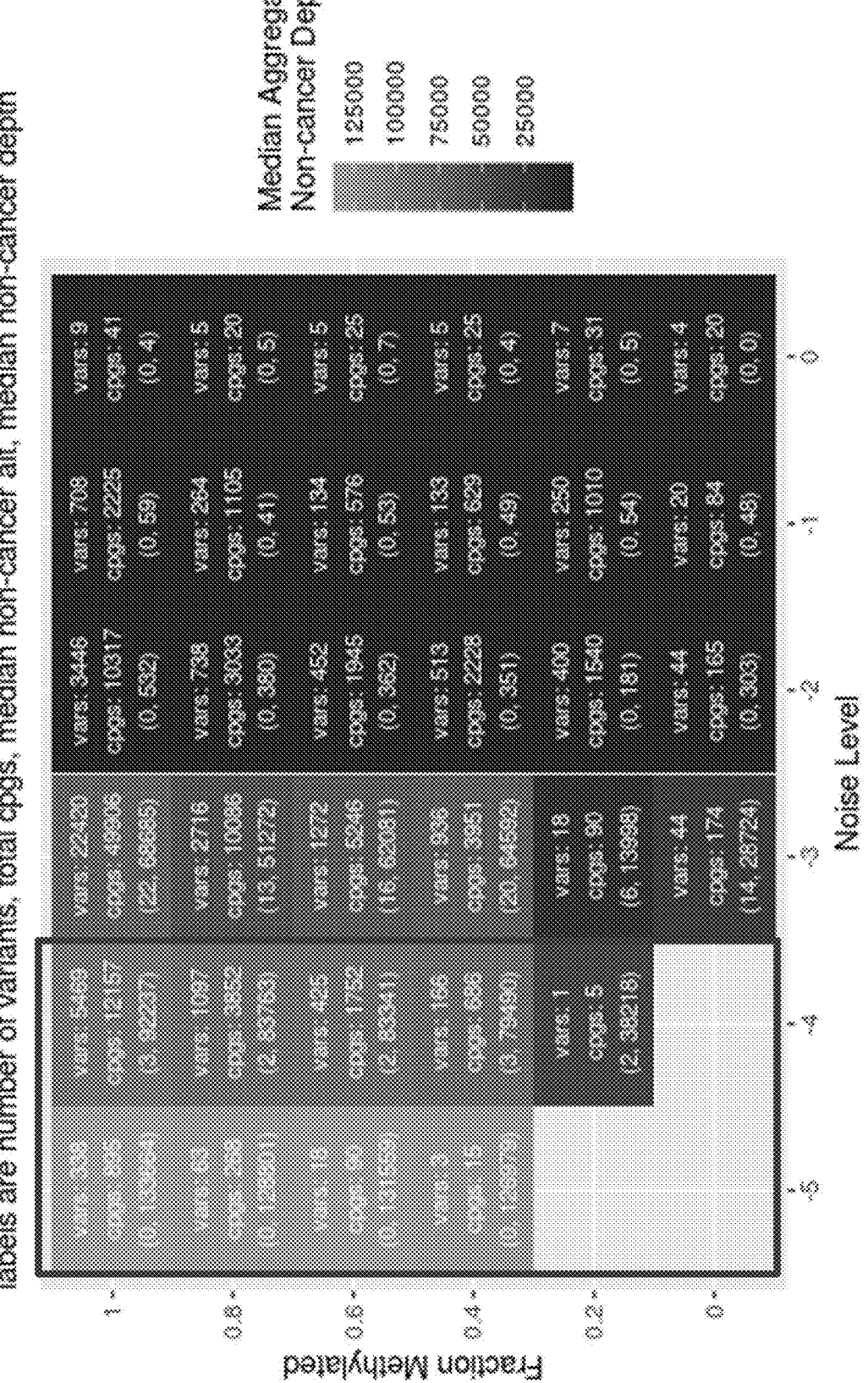
FIG. 5 illustrates a plot showing statistics of fragments (e.g., number of variants, total CpG sites, median non-cancer alt counts, median non-cancer depth) as a function of noise level and fraction methylated, in accordance with some embodiments of the present disclosure.

Test case samples were assessed to validate the suitability of component intervals as identifiers of differential methylation (e.g., biomarkers). For example, FIG. 5 illustrates the test case alleles plotted by fraction methylated versus noise level. In addition, statistics for test case data and control data were compared for component intervals at each intersecting region. Depth of coverage in the non-cancer control dataset for each candidate interval is represented as shading (light gray: high coverage; black: low coverage), while additional statistics presented for each group of intervals include: variant allele counts for the test case sample ("vars"), total number of CpGs ("cpgs"), median variant allele counts in the non-cancer control sample, and median depth of coverage in the non-cancer control sample (represented numerically in the parentheses in each grid). FIG. 5 highlights selected intervals with low noise and high depth of coverage in the non-cancer control samples, and high fraction of methylation in the test case samples.

Notably, the method for noise level calculation results in the assignment of high noise values to some intervals despite the lack of variant alleles in the control dataset, due to low depth of coverage. Thus, in some embodiments, the depth of coverage of certain specific CpG sites provides a greater indication of suitability over noise level for identifying methylation patterns. In some embodiments, the depth of coverage is determined by the type of sequencing probe used during the obtaining of sequence reads. For example, probes designed for binary sequencing (e.g., amplification of both methylated and unmethylated CpG sites) can exhibit lower noise, less bias, and greater depth of coverage than probes designed for semi-binary sequencing (e.g., amplification of either methylated or unmethylated CpG sites).

QMP Fractions Between cfD) NA and Biopsy Tissues are Correlated.

Figure 6:
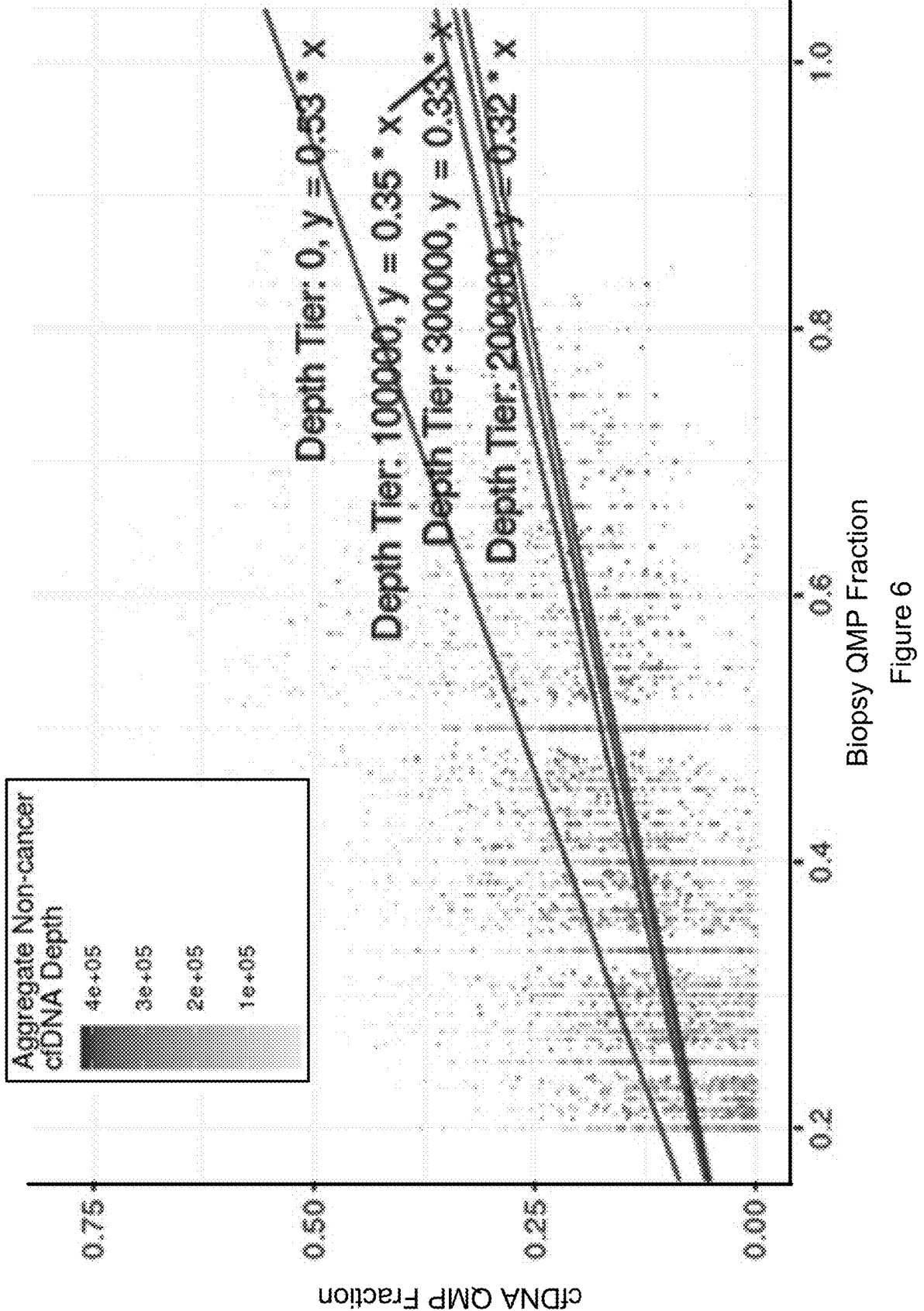
FIG. 6 illustrates a plot showing correlation between the QMP fraction of biopsy samples and the variant allele fraction of cfDNA samples, in accordance with some embodiments of the present disclosure.

FIG. 6 illustrates a comparison of fractions of QMPs calculated using either cfDNA-derived nucleic acid fragments or tissue biopsy (e.g., tumor)—derived nucleic acid fragments from test case samples. Each point on the graph represents a differentially methylated interval under investigation. Intervals were pre-filtered for noise rate $<10^{-4}$ and depth tiers were determined as pmin (floor (normal_depth/ 100000)*100000, 300000). The x-axis denotes the biopsy QMP fraction (QMP count over depth coverage), while the y-axis denotes cfDNA QMP fraction. Correlation between the two sample types is exhibited as a linear relationship between the points in the graph. For example, differentially methylated regions that are frequently observed in the tumor are observed at correlated frequencies in cfDNA where some proportion of cfDNA is tumor-derived. The slope (equal to the tumor fraction in this context) stabilizes with linear fits utilizing intervals having higher depth of coverage and low noise in the non-cancer control samples (e.g., regions amplified by binary probes).

The observation that cfDNA QMP fraction scales with tumor biopsy QMP fraction provides evidence that cfDNA-derived nucleic acid samples can be used to determine variant allele fractions (and subsequently support downstream applications such as e.g., calculating tumor fraction estimates, monitoring disease progression, and/or determining minimal residual disease). This provides a less invasive avenue for detection, diagnosis, and/or treatment of diseases such as cancer. Calculation of tumor fraction estimates is described in detail in, e.g., United States Patent Publication No. 2020-0385813 A1, entitled "Systems and Methods for Estimating Cell Source Fractions Using Methylation Information,"; International Patent Publication No. WO/2019/ 204360, entitled "SYSTEMS AND METHODS FOR DETERMINING TUMOR FRACTION IN CELL-FREE NUCLEIC ACID"; International Patent Publication No. WO 2020/132148, entitled "SYSTEMS AND METHODS FOR ESTIMATING CELL SOURCE FRACTIONS USING METHYLATION INFORMATION,"; and United States Patent Publication Number US 2020-0340064 A1, entitled "SYSTEMS AND METHODS FOR TUMOR FRACTION ESTIMATION FROM SMALL VARIANTS" each of which is hereby incorporated by reference.

Validation of Differential Methylation States.

FIGS. 10A, 10B, 10C, 10D, and 10E illustrate differential methylation at a number of CpG sites in nucleic acid fragments obtained from the high tumor fraction test case sample compared to control non-cancer samples. Differential methylation state intervals were determined using the parameters defined above: minimum depth of coverage for tumor samples=10, minimum variant allele fraction (VAF) of tumor samples=0.2, minimum depth of coverage for non-cancer sample=0, maximum VAF of non-cancer sample=0.001, and number of CpGs in the interval=5. As disclosed herein, VAF is used as a shorthand to refer to fraction values of qualifying methylation patterns (QMPs).

Differential methylation states were compared using the control non-cancer sample (including targeted methylation (COMPASS) samples), a test case tumor biopsy sample, and a test case cfDNA sample matched to the tumor biopsy sample. The summary table lists statistics for each interval, including: a start and end location for the interval ("browser_ range"), the defined methylation state ("states", e.g., MMMMM, MUMMM, etc.), the variant allele count for the tissue biopsy sample at the respective interval ("tumor_alt"), the depth of coverage for the tissue biopsy sample at the respective interval ("tumor_depth"), the variant allele count for the control non-cancer sample at the respective interval ("normal_alt"), the depth of coverage for the control non-cancer sample at the respective interval ("normal_depth"), the variant allele count for the matched test case cfDNA sample ("sample_alt"), and the depth of coverage for the matched test case cfDNA sample ("sample_depth"). For example, in FIG. 10A, the tissue biopsy sample comprises 6 instances of the defined methylation state MMMMM and 7 instances of an alternate methylation state out of a possible 13 instances, while the control non-cancer sample comprises 2 instances of the defined methylation state out of a possible 82,581 instances. The variant allele fraction for the biopsy sample is thus substantially higher relative to the variant allele fraction for the control non-cancer sample.

The Interactive Genomics Viewer (IGV) provides a tool for viewing genomic data (e.g., BAM files), including, but not limited to, methylation patterns. For example, each panel in FIG. 10A corresponds to a genomic region, comprising 5 contiguous CpG sites, from the test case tumor biopsy sample ("Biopsy") or the test case cfDNA sample ("Matched cfDNA"). Each row represents a read pair (e.g., forward and reverse strands) for a nucleic acid fragment. Each column, such as those represented by aggregate bars at the top of each panel, is a nucleotide base in a genome. Nucleic acid sequences are presented from left to right in the forward strand orientation, such that CpG sites are read as C-G for forward strands, and G-C for reverse strands in each panel. Grey and black lines denote methylated and unmethylated cytosines, respectively, for each strand in a read pair. Gray lines denote non-cytosine (e.g., non-applicable) bases, while brown lines denote single nucleotide polymorphisms (SNPs). The aggregate bars at the top of each panel represent the sum of all calls (e.g., methylated cytosines, unmethylated cytosines, and other/non-applicable) for all reads in all fragments. Notably, depending on coverage depth, the aggregate representation of a given nucleotide can include one, two or three calls due to the presence of methylated and/or unmethylated cytosines between multiple nucleic acid fragments, as well as the presence of complementary guanines in alternate reads.

The IGV panels illustrated in FIGS. 10A, 10B, 10C, 10D, and 10E reveal variant methylation patterns for various CpG intervals, where both the test case tumor biopsy and the matched test case cfDNA are similarly distinct from the non-cancer cfDNA control sample. These examples indicate that the CpG intervals identified using the disclosed method, in accordance with some embodiments, comprise differential methylation states between test and control samples, which can be further used for downstream identification and/or classification purposes.

Example 5 Comparing Methylation and ART Tumor Fraction Estimates

Targeted sequencing data for tissue and white blood cell samples (ART) and whole-genome bisulfite sequencing data for tissue and cfDNA (Methylation) were obtained from a plurality of participant samples from the CCGA study. ART sequencing data was used to identify small variants, which were in turn used to calculate tumor fraction estimates. Due to its characteristic high coverage depth (e.g., up to 2000-3000× at each small variant), ART tumor fraction estimates were used to establish a baseline for subsequent comparison.

Methylation data was similarly used to calculate tumor fraction estimates for each respective participant, using a median posterior estimate with 95% credible interval. Specifically, tissue WGBS data was used to identify and call differentially methylated sites, while cfDNA WGBS data was used to evaluate the methylation states at each site and determine the tumor fraction estimates.

Systems and methods for the calculation of tumor fraction estimates is described in detail in, e.g., United States Patent Publication No. 2020-0385813, entitled "Systems and Methods for Estimating Cell Source Fractions Using Methylation Information", which is hereby incorporated by reference. In brief, tumor fraction estimates are calculated from the observed variant frequency in the obtained sequence reads for a respective sample. The variant count data across all variant sites in the sample is modeled to provide a posterior estimate of the tumor fraction.

Figure 11:
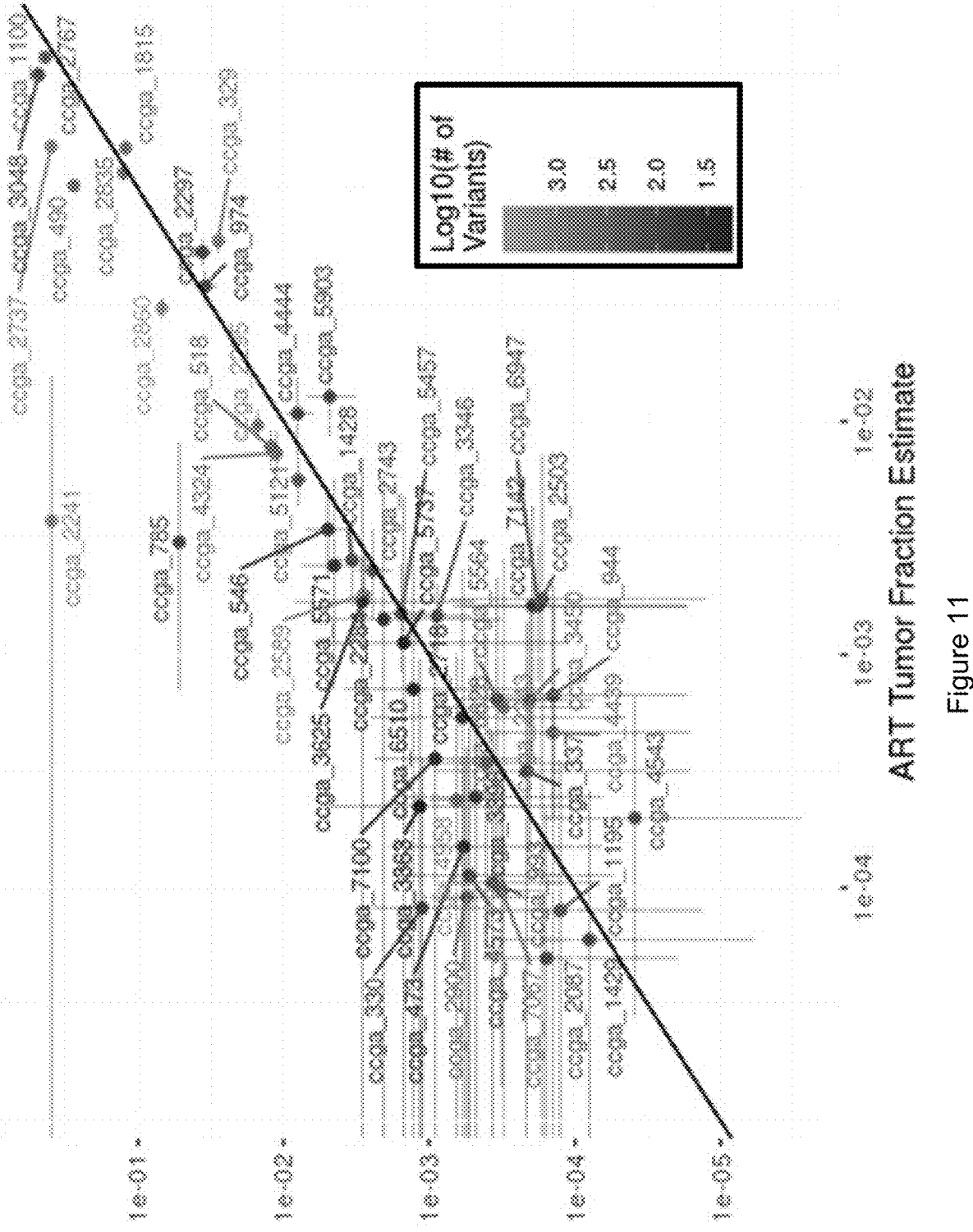
FIG. 11 illustrates a comparison of methylation tumor fraction estimates calculated using methylation (e.g., bisulfite) sequencing with tumor fraction estimates calculated using targeted and whole-genome sequencing of cfDNA and tumor samples, in accordance with some embodiments of the present disclosure.

FIG. 11 illustrates the plot of methylation tumor fraction estimates (y-axis) against ART tumor fraction estimates (x-axis), where individual participant samples are denoted by each point in the plot, and the tumor fraction estimate for each individual participant was determined using all variant sites included in the respective participant sample, as described above. Only participants exhibiting read evidence of small variants in the targeted (ART) sequencing assay were included in the plot. This limitation was included to confirm truthfulness of the tumor fraction estimate and to exclude participants where the tumor fraction estimate was nevertheless determined by posterior distribution despite a lack of evidence for small variants.

The plot exhibits a linear relationship between the two estimates, revealing a concordance between the tumor fraction estimation when using data from either method of targeted sequencing or methylation sequencing. This concordance was observed for estimated tumor fractions as low as 10-4, suggesting that the correlation is robust. It can be concluded, therefore, that methylation sequencing provides as accurate and reliable a foundation for tumor fraction estimation and any subsequent downstream applications as targeted sequencing for small variants.

Example 6—Ability to Detect Cancer as a Function of cfDNA Fraction

The A score classifier, described herein is a classifier of tumor mutational burden based on targeted sequencing analysis of nonsynonymous mutations. For example, a classification score (e.g., "A score") can be computed using logistic regression on tumor mutational burden data, where an estimate of tumor mutational burden for each individual is obtained from the targeted cfDNA assay. In some embodiments, a tumor mutational burden can be estimated as the total number of variants per individual that are: called as candidate variants in the cfDNA, passed noise-modeling and joint-calling, and/or found as nonsynonymous in any gene annotation overlapping the variants. The tumor mutational burden numbers of a training set can be fed into a penalized logistic regression classifier to determine cutoffs at which 95% specificity is achieved using cross-validation. Additional details on A score can be found, for example, in Chaudhary et al., 2017, Journal of Clinical Oncology, 35 (5), suppl.e14529, pre-print online publication, which is hereby incorporated by reference herein in its entirety.

The B score classifier is described in United States Patent Publication Number US 2019-0287649 A1, entitled "Method and System for Selecting, Managing, and Analyzing Data of High Dimensionality," which is hereby incorporated by reference. In accordance with the B score method, a first set of sequence reads of nucleic acid samples from healthy subjects in a reference group of healthy subjects are analyzed for regions of low variability. Accordingly, each sequence read in the first set of sequence reads of nucleic acid samples from each healthy subject can be aligned to a region in the reference genome. From this, a training set of sequence reads from sequence reads of nucleic acid samples from subjects in a training group can be selected. Each sequence read in the training set aligns to a region in the regions of low variability in the reference genome identified from the reference set. The training set includes sequence reads of nucleic acid samples from healthy subjects as well as sequence reads of nucleic acid samples from diseased subjects who are known to have the cancer. The nucleic acid samples from the training group are of a type that is the same as or similar to that of the nucleic acid samples from the reference group of healthy subjects. From this it is determined, using quantities derived from sequence reads of the training set, one or more parameters that reflect differences between sequence reads of nucleic acid samples from the healthy subjects and sequence reads of nucleic acid samples from the diseased subjects within the training group. Then, a test set of sequence reads associated with nucleic acid samples comprising cfDNA fragments from a test subject whose status with respect to the cancer is unknown is received, and the likelihood of the test subject having the cancer is determined based on the one or more parameters.

The M score classifier is described in United States Patent Publication No. US 2019-0287652 A1, entitled "Methylation Fragment Anomaly Detection," filed Mar. 13, 2019, and in United States Patent Publication No. 2020-0385813 A1, entitled "Systems and Methods for Estimating Cell Source Fractions Using Methylation Information," each of which is hereby incorporated by reference.

Example 7—Example Methods for Estimating Tumor Fractions

For non-methylation sequencing data, several methods were developed for estimating tumor fraction of a cfDNA sample. See, International Patent Publication No. WO/2019/204360, entitled "SYSTEMS AND METHODS FOR DETERMINING TUMOR FRACTION IN CELL-FREE NUCLEIC ACID," International Patent Publication No. WO 2020/132148, entitled "SYSTEMS AND METHODS FOR ESTIMATING CELL SOURCE FRACTIONS USING METHYLATION INFORMATION," United States Patent Publication Number US 2020-0340064 A1, entitled "SYSTEMS AND METHODS FOR TUMOR FRACTION ESTIMATION FROM SMALL VARIANTS, each of which is hereby incorporated by reference. For example, one of the approaches was illustrated as method 1300 in FIG. 13A. In this approach, nucleic acid samples from formalin-fixed, paraffin-embedded (FFPE) tumor tissues (e.g., 1304) and nucleic acid samples from white blood cells (WBC) from the matching patient (e.g., 1306) were sequenced by whole-genome sequencing (WGS). Somatic variants identified based on the sequencing data (e.g., 1308) were analyzed against matching cfDNA sequencing data from the same patient (e.g., 1310) were used to determine a tumor fraction estimate (e.g., 1312).

For methylation sequencing data, multiple methods were developed for estimating tumor fraction of a cfDNA sample based on methylation data (obtained by targeted methylation or WGBS. See International Patent Publication No. WO 2020/132148, entitled "SYSTEMS AND METHODS FOR ESTIMATING CELL SOURCE FRACTIONS USING METHYLATION INFORMATION"; United States Patent Publication Number US 2020-0340064 A1, entitled "SYSTEMS AND METHODS FOR TUMOR FRACTION ESTIMATION FROM SMALL VARIANTS", each of which is hereby incorporated by reference. For example, one of the approaches was illustrated as method 1302 in FIG. 13B. In this approach, nucleic acid samples from formalin-fixed, paraffin-embedded (FFPE) tumor tissues (e.g., 1314) were analyzed by whole-genome bisulfite sequencing (WGBS). Somatic variants identified based on the sequencing data (e.g., 1316) were analyzed against matching cfDNA WGBS sequencing data from the same patient (e.g., 1318) were used to determine a tumor fraction estimate (e.g., 1320).

A procedure like bisulfite conversion makes variant identification based on methylation sequencing data more challenging. As such, alternatives to variant-based methods are needed for estimating tumor fractions based on methylation sequencing data. Examples of tumor fraction analysis based on WGBS sequencing data are detailed in this example.

FIGS. 14 and 15 illustrates two ways of using qualifying methylation patterns (QMPs). In these examples, QMPs are used to quantify tumor derived nucleic acid in lieu of traditional variant mutations such as SNPs and/or SNVs.

In these two examples, CCGA data were leveraged to examine the relationship between cfDNA containing tumor DNA methylation patterns, TF, and cancer classification performance. The CCGA classifier was trained on whole-genome bisulfite sequencing (WGBS) and targeted methylation (TM) sequencing data to detect cancer versus noncancer. 822 samples had biopsy WGBS performed; of those, 231 also had cfDNA targeted methylation (TM) and cfDNA whole-genome sequencing (WGS). Biopsy WGBS identified somatic single nucleotide variants (SNV) and qualifying methylation patterns (QMP; defined as methylation patterns in sequenced DNA fragments observed commonly in biopsy but rarely [<1/10,000] in the cfDNA of non-cancer controls [n=898]). In certain instances in the current disclosure, the QMPs were also referred to as "methylation variant" or MV. Observed tumor fragment counts (SNV in WGS; QMPs in TM) were modeled as a Poisson process with rate dependent on TF. TF and classifier limits of detection (LOD) were each assessed using Bayesian logistic regression.

Results. Across biopsy samples, a median of 2,635 QMPs were distributed across the genome, with a median of 86.8% shared with ≥1 participant, and a median of 69.3% targeted by the TM assay. TF LOD from QMPs was 0.00050 (95% credible interval [CI]: 0.00041-0.00061); QMPs and SNV estimates were concordant (Spearman's Rho: 0.820). QMPs TF estimates explained classifier performance (Spearman's Rho: 0.856) and allowed determination of the classifier LOD (0.00082 [95% CI: 0.00057-0.00115]).

Conclusions. These data demonstrate the existence of methylation patterns in tumor-derived cfDNA fragments that are rarely found in individuals without cancer; their abundance directly measured TF, and was a major factor influencing classification performance. Finally, the low classifier LOD (~0.1%) motivates further clinical development of a methylation-based assay for cancer detection.

FIG. 14A illustrates an example process 1400 of using QMPs to estimate an abundance level of tumor derived nucleic acids based on, for example, WGBS sequencing data. In this diagram and in FIG. 15A, data are represented by oval blocks (e.g., 1402, 1404, and 1410) while analytic results are represented in rectangular blocks (e.g., 1406 and 1420). In particular, a biopsy nucleic acid sample (e.g., from formalin-fixed, paraffin-embedded (FFPE) tumor tissues) from a cancer subject x is sequenced using whole genome bisulfite sequencing (WGBS). The sequencing data is compared with a reference dataset (e.g., 1404, WGBS data of plasma cfDNA samples from a group of non-cancer control group) to identify a set of QMPs (e.g., 1406). In this particular example, the dataset at 1404 included 898 non-cancer samples. In some alternative embodiments, rather than WGBS data, 1404 can be targeted methylation data of plasma cfDNA of a non-cancer control group. In some embodiments, at step 1410, another sample from the same cancer subject x (e.g., a cfDNA sample) is used to generate a new WGBS dataset. In some embodiments, the sample of 1410 is collected from the subject at a later time relative to the sample of step 1402, for instance after treating the subject with a treatment for their cancer condition. The abundance level of each of the previously identified QMPs is determined based on this new WGBS dataset. In some embodiments, the abundance levels can be used to compute a tumor fraction estimate. In some alternative embodiments, the same cancer sample is used at both steps 1402 and 1410.

In some embodiments illustrated as optional 1408, the WGBS dataset from 1410 can be used in combination with the WGBS data from 1402 to facilitate QMP identification at 1406.

FIG. 14B illustrates an example method 1430 for qualifying abundance level of each of a set of identified QMPs. At step 1440, a plurality of fragment methylation patterns (FMP) is obtained based on methylation sequencing data (e.g., based on WGBS) from a biopsy sample of a cancer subject (e.g., from formalin-fixed, paraffin-embedded (FFPE) tumor tissues). In some embodiments, an FMP represents the methylation status of the CpG sites in a full nucleic acid fragment or a portion thereof. For example, the FMP of a nucleic acid fragment containing 7 CpG sites (e.g., a predetermined length of the FMP) can be MUMUMUU where each M denotes a methylated CpG site and U denotes an unmethylated CpG site, and each CpG denoted by M or U has a corresponding genomic coordinate. In some embodiments, the predetermined length of the FMP can be shorter than the total number of CpG sites in the nucleic acid fragment and can be changed to six or five. As such, the nucleic acid fragments can correspond to multiple FMPs. When the predetermined length is six, the nucleic acid fragments can correspond to MUMUMU (corresponding to CpG sites 1-6 in the fragment) or UMUMUU (corresponding to CpG sites 2-7 in the fragment). When the predetermined length is five, the nucleic acid fragments can correspond to MUMUM (corresponding to CpG sites 1-5 in the fragment), UMUMU (corresponding to CpG sites 2-6 in the fragment), or MUMUU (corresponding to CpG sites 3-7 in the fragment). It is to be noted that, when the total number of CpG sites in a fragment is much larger than the predetermined length of a FMP, it is possible to derive multiple "apparently identical" FMPs based on a single nucleic acid fragment. This is true, for example, for a fragment containing 11 CpG sites: MMUMMUMMUMM. When a predetermined length of an FMP is five, it is possible to have at least three apparently-identical: MMUMM (corresponding to CpG sites 1-5 in the fragment), MMUMM (corresponding to CpG sites 4-8 in the fragment), and MMUMM (corresponding to CpG sites 7-11 in the fragment). While the sequence of methylation status of these three different sets of CpG sites is identical, they can represent three different FMP because the CpG sites encompassed in each correspond to different genomic coordinates. In some embodiments, for a predetermined length, a collection of FMPs can be identified for all nucleic acid fragments based on a methylation sequencing dataset for the cancer subject. In some embodiments, multiple collections of FMPs can be identified, each for a predetermined length.

In some embodiments, the collection of FMPs is derived from WGBS data.

At step 1445, qualifying methylation patterns (QMPs) for the cancer subject are identified based on the FMPs identified at the previously step, using a reference dataset (e.g., based on WGBS sequencing data from a group of non-cancer subjects; e.g., the negative controls). Methods for identifying QMPs can be those as described in FIG. 2.

In some embodiments, QMPs are identified as those FMPs that are only present in the cancer subject and not the control non-cancer subjects. In some embodiments (such as those described in FIG. 2), FMPs from multiple cancer subjects can be compared to methylation sequencing data of non-caner controls in order to identify a set of AMPs for the multiple cancer subjects. In some embodiments, cfDNAs from non-cancer patients are used to establish the reference WGBS methylation data of 1404.

At step 1450, additional methylation sequencing data (e.g., WGBS data 1410 of matching cfDNA sample from the same cancer subject) can be used to estimate tumor fraction.

At optional step 1452, the additional methylation sequencing data (e.g., WGBS data 1410 of matching cfDNA sample from the same cancer subject) can be used in combination with the matching biopsy methylation sequencing data from step 1430 to facilitate identification of QMPs for the cancer subject.

Once a set of QMPs is identified for the cancer subject, abundance level of each identified QMP can be determined based on the methylation sequencing data from step 1450. For example, the number of unique nucleic acid fragments that harbor a particular QMP can be counted as an indicator of its abundance level. In some embodiments, the abundance level of each QMP in the identified QMP set can be used to estimate a tumor fraction for the cancer subject based on applicable methods including but not limited to a method using equation (1).

In some embodiments, the process illustrated in FIGS. 14A and 14B can be applied to a group of cancer subjects. In some embodiments, the group of cancer subjects can be sub-divided based on specific cancer types. Features extracted from these sub-divided groups can be combined in an overall model for computing tumor fractions across a different cancer types. Alternatively, separate tumor fraction models can be determined for different cancer types.

FIGS. 15A and 15B depict QMP-based methods for estimating tumor fraction using targeted methylation (TM) data. As illustrated in FIG. 15A, the overall set up 1500 is general similar to those illustrated in FIG. 14A (see, e.g., 1502, 1504, and 1506). In addition, additional steps are needed to address impacts from targeted methylation sequencing: for example, i) TM sequencing data from a cancer subject are used (e.g., 1510), ii) additional TM sequencing data from non-cancer samples are used (e.g., 1512), and iii) selected regions are enriched affecting coverage or sequencing depth. As such, sequencing depths for TM sequencing data must be calibrated accordingly (e.g., based on 1515) before they are used for estimating tumor fraction (e.g., 1520). For example, mixtures of 50/50 of 0% and 100% methylated genomic DNAs can be subject to parallel WGBS and TM analysis to assess the effects of enrichment probes on perceived sequencing depth.

FIG. 15B illustrates the method steps corresponding to FIG. 15A. The overall methodology is similar to those illustrated in FIG. 14B. For example, at step 1540, similar to step 1440, FMPs are obtained based on biopsy WGBS data of a nucleic acid sample derived from a tumor tissue of a cancer subject.

At step 1545, a set of QMPs are identified based on the biopsy WGBS data obtained at the previous step and WGBS cfDNA data from non-cancer subjects. Here, the sequencing data of the non-cancer subjects are used as negative controls; for example, to exclude or blacklist certain fragment methylation patterns or FMPs. In addition, FMPs that are relatively abundant in WGBS data from biopsy-derived nucleic acids and cfDNA samples tend to be less useful for cancer classification, in particular, for tissue-of-origin analysis; thus, these can excluded as well in some embodiments.

At step 1550, QMPs identified in the previous step can be further refined and calibrated before being used in a number of applications, including but not limited to, tumor fraction estimate, assessment of cancer or tissue-of-origin classification, and more. In some embodiments, at step 1550-1, targeted methylation (TM) sequencing data are obtained from a matching cfDNA sample from the same subject. For example, a bisulfite preparation of cfDNA sample from step 1545 can be divided into two portions: one can be used in WGBS sequencing and the other undergoes targeted enrichment (e.g., by one or more rounds of hybridization to nucleic acid probes) before the enriched sample is washed, eluted, amplified by PCR, normalized, pooled, and subject to methylation sequencing analysis. The dataset from 1550-1 will be used as basis, for example, for estimating TF. In some embodiments, illustrated as 1550-2, another TM sequencing dataset of cfDNA samples from non-cancer subjects can be used to exclude or blacklist FMPs from the final set of QMPs. After step 1550, a refined set of QMPs can be obtained for subsequent analysis.

Because certain regions of the genome are enriched, the coverage or depth of the enriched regions would be larger than their actual values, and thus should be calibrated (e.g., 1550-3). In some embodiments, known calibration samples can be sequenced with and without enrichment. For example, a starting material can be created by mixing completely methylated nucleic acids with completely unmethylated nucleic acids. Two samples are subsequently created whose nucleic acid content is calibrated with each other; for example, the first sample is the same as the starting material and the second sample has been enriched using probes designed for the TM sequencing assay. Both samples are then subject to methylation sequencing analysis. Coverage and depth of certain CpG sites are then compared using sequencing data of the two samples in order to reduce pulldown bias.

At step 1555, abundance level of each QMP in the refined set of QMPs can be assess based on the TM methylation data from 1550-1 before they are used to estimate tumor fraction.

Example 8—Targeted Methylation Fraction Estimates Based on QMPs cfDNA tumor fraction as estimated from the rate of tumor biopsy feature shedding for methylation variants (y-axis, see below for more details) versus short genetic variants is disclosed in this example. For 231 training set participants, variants were identified from 30× whole genome bisulfite sequencing of FFPE tumor biopsy samples after modelling sequencing error and population variation (see Supplementary Methods). Participant cfDNA tumor fraction estimates are represented by black circles; 95% credible intervals are indicated by horizontal or vertical gray lines. The diagonal gray line represents perfect agreement between the two methods.

Tumor fraction was also calculated from methylation patterns as follows. A methylation variant was defined as a set of 5 contiguous CpGs and their methylation states (e.g., $CpG_{10}$-$CpG_{14}$ MMMMM) that occurred in a tumor biopsy WGBS data sample ($\geq 0.2$ variant allele fraction, $\geq 10\times$ total depth of fragments spanning the site), and that occurred infrequently in aggregated non-cancer cfDNA WGBS data ($\leq 0.001$ variant allele fraction). Methylation variants identified in matched biopsy samples were filtered to those (1) with 0% or 100% methylated CpGs, (2) that were effectively pulled down by our targeted methylation assay in control experiments with a mixture of 0% methylated and 100% methylated genomic DNA at a predetermined composition (e.g., at 50/50, 40/60, 30/70, 20/80, or 10/90 ratios), and (3) that formed a non-overlapping set (to mitigate double counting). Pull-down bias was estimated per site using various control data. Posterior tumor fractions estimates were generated using counts of variant matched and non-matched fragments covering each variant site. A Poisson likelihood model per site was employed where the rate constant was calculated as a function of the tumor fraction, the pull-down bias, the estimated total sequencing depth, and the background noise rate. This method was rigorously developed and validated using synthetic dilutions and comparison to estimates produced from patient matched WGBS of cfDNA (manuscript in preparation).

Tumor fraction was estimated from the observed counts of fragments with tumor features in cfDNA. Genetic small nucleotide variant and methylation variant tumor features were determined from WGBS of tumor tissue biopsies. A subset of 231 participants had matched tumor biopsy and cfDNA sequencing in the training set and were used in the tumor fraction estimations. This set of participants excluded those whose biopsies were used in target selection.

More specifically, to calculate the tumor-fraction from SNVs, a joint analysis of WGBS of tumor tissue and WGS of cfDNA was performed to identify tumor-associated somatic small nucleotide variants. See, for example, U.S. Provisional Patent Application No. 62/983,404, entitled, "Systems and Methods for Calling Variants Using Methylation Sequencing Data," filed Feb. 28, 2020, which is hereby incorporated by reference. This process started with calling SNVs within WGBS tissue using a custom variant caller that accounted for the effects of bisulfite conversion (unmethylated C-to-T conversion) by using strand-specific pileups and a Bayesian genotype model. Once a candidate list of SNVs was generated, a series of filtering steps were undertaken in order to enrich for somatic variants, since filtering using a matched-normal reference for these individuals was not available. These filters included the minimum and maximum variant allele frequencies (VAFs), minimum depth, a custom blacklist of known noisy sites, the removal of germline-variants private to an individual as marked by freebayes within sample-matched WGS cfDNA, and blacklisting of known germline variants using gnomAD and dbSNP. Counts of fragments supporting and not supporting each variant were generated from matched WGS sequencing of corresponding cfDNA samples. Posterior tumor fraction estimates were calculated using a grid search over tumor fractions and employing a per variant likelihood defined as a mixture of binomial likelihoods. The mixture components accounted for (1) observing fragments due to tumor shedding as well as (2) various error modes including germline variants and falsely called variants. Median and 95% credible intervals were calculated for each participant's tumor fraction.

Example 9—Example Cell Sources

In some embodiments, a cell source of any embodiment of the present disclosure (a respective biological sample obtained from a corresponding subject in a first, second, or third set of subjects, or a target subject) is a first cancer of a common primary site of origin. In some embodiments, the first cancer is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, gastric cancer, or a combination thereof.

In some embodiments, a cell source of any embodiment of the present disclosure is a tumor of a certain cancer type, or a fraction thereof. In some embodiments, the tumor is an adrenocortical carcinoma, a childhood adrenocortical carcinoma, a tumor of an AIDS-related cancer, kaposi sarcoma, a tumor associated with anal cancer, a tumor associated with an appendix cancer, an astrocytoma, a childhood (brain cancer) tumor, an atypical teratoid/rhabdoid tumor, a central nervous system (brain cancer) tumor, a basal cell carcinoma of the skin, a tumor associated with bile duct cancer, a bladder cancer tumor, a childhood bladder cancer tumor, a bone cancer (e.g., ewing sarcoma and osteosarcoma and malignant fibrous histiocytoma) tissue, a brain tumor, breast cancer tissue, childhood breast cancer tissue, a childhood bronchial tumor, burkitt lymphoma tissue, a carcinoid tumor (gastrointestinal), a childhood carcinoid tumor, a carcinoma of unknown primary, a childhood carcinoma of unknown primary, a childhood cardiac (heart) tumor, a central nervous system (e.g., brain cancer such as childhood atypical teratoid/rhabdoid) tumor, a childhood embryonal tumor, a childhood germ cell tumor, cervical cancer tissue, childhood cervical cancer tissue, cholangiocarcinoma tissue, childhood chordoma tissue, a chronic myeloproliferative neoplasm, a colorectal cancer tumor, a childhood colorectal cancer tumor, childhood craniopharyngioma tissue, a ductal carcinoma in situ (DCIS), a childhood embryonal tumor, endometrial cancer (uterine cancer) tissue, childhood ependymoma tissue, esophageal cancer tissue, childhood esophageal cancer tissue, esthesioneuroblastoma (head and neck cancer) tissue, a childhood extracranial germ cell tumor, an extragonadal germ cell tumor, eye cancer tissue, an intraocular melanoma, a retinoblastoma, fallopian tube cancer tissue, gallbladder cancer tissue, gastric (stomach) cancer tissue, childhood gastric (stomach) cancer tissue, a gastrointestinal carcinoid tumor, a gastrointestinal stromal tumor (GIST), a childhood gastrointestinal stromal tumor, a germ cell tumor (e.g., a childhood central nervous system germ cell tumor, a childhood extracranial germ cell tumor, an extragonadal germ cell tumor, an ovarian germ cell tumor, or testicular cancer tissue), head and neck cancer tissue, a childhood heart tumor, hepatocellular cancer (HCC) tissue, an islet cell tumor (pancreatic neuroendocrine tumors), kidney or renal cell cancer (RCC) tissue, laryngeal cancer tissue, leukemia, liver cancer tissue, lung cancer (non-small cell and small cell) tissue, childhood lung cancer tissue, male breast cancer tissue, a malignant fibrous histiocytoma of bone and osteosarcoma, a melanoma, a childhood melanoma, an intraocular melanoma, a childhood intraocular melanoma, a merkel cell carcinoma, a malignant mesothelioma, a childhood mesothelioma, metastatic cancer tissue, metastatic squamous neck cancer with occult primary tissue, a midline tract carcinoma with NUT gene changes, mouth cancer (head and neck cancer) tissue, multiple endocrine neoplasia syndrome tissue, a multiple myeloma/plasma cell neoplasm, myelodysplastic syndrome tissue, a myelodysplastic/myeloproliferative neoplasm, a chronic myeloproliferative neoplasm, nasal cavity and paranasal sinus cancer tissue, nasopharyngeal cancer (NPC) tissue, neuroblastoma tissue, non-small cell lung cancer tissue, oral cancer tissue, lip and oral cavity cancer and oropharyngeal cancer tissue, osteosarcoma and malignant fibrous histiocytoma of bone tissue, ovarian cancer tissue, childhood ovarian cancer tissue, pancreatic cancer tissue, childhood pancreatic cancer tissue, papillomatosis (childhood laryngeal) tissue, paraganglioma tissue, childhood paraganglioma tissue, paranasal sinus and nasal cavity cancer tissue, parathyroid cancer tissue, penile cancer tissue, pharyngeal cancer tissue, pheochromocytoma tissue, childhood pheochromocytoma tissue, a pituitary tumor, a plasma cell neoplasm/multiple myeloma, a pleuropulmonary blastoma, a primary central nervous system (CNS) lymphoma, primary peritoneal cancer tissue, prostate cancer tissue, rectal cancer tissue, a retinoblastoma, a childhood rhabdomyosarcoma, salivary gland cancer tissue, a sarcoma (e.g., a childhood vascular tumor, osteosarcoma, uterine sarcoma, etc.), Sézary syndrome (lymphoma) tissue, skin cancer tissue, childhood skin cancer tissue, small cell lung cancer tissue, small intestine cancer tissue, a squamous cell carcinoma of the skin, a squamous neck cancer with occult primary, a cutaneous t-cell lymphoma, testicular cancer tissue, childhood testicular cancer tissue, throat cancer (e.g., nasopharyngeal cancer, oropharyngeal cancer, hypopharyngeal cancer) tissue, a thymoma or thymic carcinoma, thyroid cancer tissue, transitional cell cancer of the renal pelvis and ureter tissue, unknown primary carcinoma tissue, ureter or renal pelvis tissue, transitional cell cancer (kidney (renal cell) cancer tissue, urethral cancer tissue, endometrial uterine cancer tissue, uterine sarcoma tissue, vaginal cancer tissue, childhood vaginal cancer tissue, a vascular tumor, vulvar cancer tissue, a Wilms tumor or other childhood kidney tumor.

In some embodiments, a cell source of any embodiment of the present disclosure is a first cancer. In some such embodiments, the first cancer is a stage of a breast cancer, a stage of a lung cancer, a stage of a prostate cancer, a stage of a colorectal cancer, a stage of a renal cancer, a stage of a uterine cancer, a stage of a pancreatic cancer, a stage of a cancer of the esophagus, a stage of a lymphoma, a stage of a head/neck cancer, a stage of a ovarian cancer, a stage of a hepatobiliary cancer, a stage of a melanoma, a stage of a cervical cancer, a stage of a multiple myeloma, a stage of a leukemia, a stage of a thyroid cancer, a stage of a bladder cancer, or a stage of a gastric cancer.

In some embodiments, a cell source of any embodiment of the present disclosure is a predetermined stage of a breast cancer, a predetermined stage of a lung cancer, a predetermined stage of a prostate cancer, a predetermined stage of a colorectal cancer, a predetermined stage of a renal cancer, a predetermined stage of a uterine cancer, a predetermined stage of a pancreatic cancer, a predetermined stage of a cancer of the esophagus, a predetermined stage of a lymphoma, a predetermined stage of a head/neck cancer, a predetermined stage of a ovarian cancer, a predetermined stage of a hepatobiliary cancer, a predetermined stage of a melanoma, a predetermined stage of a cervical cancer, a predetermined stage of a multiple myeloma, a predetermined stage of a leukemia, a predetermined stage of a thyroid cancer, a predetermined stage of a bladder cancer, or a predetermined stage of a gastric cancer.

In some embodiments, a cell source of any embodiment of the present disclosure is from a non-cancerous tissue. In some embodiments, a cell source of any embodiment of the present disclosure is from cells that derive from healthy tissue. In some embodiments, a cell source of any embodiment of the present disclosure is from a healthy tissue such as breast, lung, prostate, colorectal, renal, uterine, pancreatic, esophageal, lymph, ovarian, cervical, epidermal, thyroid, bladder, gastric, or a combination thereof.

In some embodiments, a cell source of any embodiment of the present disclosure is derived from one tissue type. In some embodiments, a cell source of any embodiment of the present disclosure is derived from two or more tissue types. In some embodiments, a tissue type includes one or more cell types (e.g., a combination of healthy, non-cancerous cells and cancerous cells). In some embodiments, a tissue type includes one cell type (e.g., one of either cancerous or healthy, non-cancerous cells).

In some embodiments, a cell source of any embodiment of the present disclosure constitutes one cell type, two cell types, three cell types, four cell types, five cell types, six cell types, seven cell types, eight cell types, nine cell types, ten cell types, or more than ten cell types.

In some embodiments, a cell source of any embodiment of the present disclosure is liver cells. In some such embodiments, the cell source is hepatocytes, hepatic stellate fat storing cells (ITO cells), Kupffer cells, sinusoidal endothelial cells, or any combination thereof.

In some embodiments, a cell source of any embodiment of the present disclosure is stomach cells. In some such embodiments, the first cell source is parietal cells.

In some embodiments, a cell source of any embodiment of the present disclosure is one or more types of human cells. In some such embodiments, the cell source is adaptive NK cells, adipocytes, alveolar cells, Alzheimer type II astrocytes, amacrine cells, ameloblasts, astrocytes, B cells, basophils, basophil activation cells, basophilia cells, Betz cells, bistratified cells, Boettcher cells, cardiac muscle cells, CD4+ T cells, cementoblasts, cerebellar granule cells, cholangiocytes, cholecystocytes, chromaffin cells, cigar cells, club cells, orticotropic cells, cytotoxic T cells, dendritic cells, enterochromaffin cells, enterochromaffin-like cells, eosinophils, extraglomerular mesangial cells, faggot cells, fat pad cells, gastric chief cells, goblet cells, gonadotropic cells, hepatic stellate cells, hepatocytes, hypersegmented neutrophils, intraglomerular mesangial cells, juxtaglomerular cells, keratinocytes, kidney proximal tubule brush border cells, Kupffer cells, lactotropic cells, Leydig cells, macrophages, macula densa cells, mast cells, megakaryocytes, melanocytes, microfold cells, monocytes, natural killer cells, natural killer T cells, glitter cells, neutrophils, osteoblasts, osteoclasts, osteocytes, oxyphil cells (parathyroid), paneth cells, parafollicular cells, parasol cells, parathyroid chief cells, parietal cells, parvocellular neurosecretory cells, peg cells, pericytes, peritubular myoid cells, platelets, podocytes, regulatory T cell, reticulocytes, retina bipolar cells retina horizontal cells, retinal ganglion cells, retinal precursor cells, sentinel cells, sertoli cells, somatomammotrophic cells, somatotropic cells, stellate cells, sustentacular cells, T cells, T helper cells, telocytes, tendon cells, thyrotropic cells, transitional B cells, trichocytes (human), tuft cells, unipolar brush cells, white blood cells, zellballens, or any combination thereof. In some such embodiments, such cells of the first cell source are healthy. In alternative embodiments, such cells of the first cell source are afflicted with cancer.

In some embodiments, a cell source of any embodiment of the present disclosure is any combination of cell types provided that such cell types originated from a single organ. In some such embodiments, this single organ is breast, lung, prostate, colon/rectum, kidney, uterus, pancreas, esophagus, blood, head/neck, ovary, liver, cervix, thyroid, bladder, or stomach. In some embodiments this single organ is healthy. In alternative embodiments, this single organ is afflicted with cancer that originated in the single organ. In still further alternative embodiments, this single organ is afflicted with cancer that originated in an organ other than the single organ and metastasized to the single organ.

In some embodiments, a cell source of any embodiment of the present disclosure is any combination of cell types provided that such cell types originated from a predetermined set of organs. In some such embodiments, this predetermined set of organs is any two organs in the set breast, lung, prostate, colon/rectum, kidney, uterus, pancreas, esophagus, blood, head/neck, ovary, liver, cervix, thyroid, bladder, and stomach. In some embodiments this predetermined set of organs is healthy. In alternative embodiments, this predetermined set of organs is afflicted with cancer that originated in one of the organs in the predetermined set of organs. In still further alternative embodiments, the predetermined set of organs is afflicted with cancer that originated in an organ other than the predetermined set of organs and metastasized to the predetermined set of organs.

In some embodiments, a cell source of any embodiment of the present disclosure is any combination of cell types provided that such cell types originated from a predetermined set of organs. In some such embodiments, this predetermined set of organs is any three organs in the set breast, lung, prostate, colon/rectum, kidney, uterus, pancreas, esophagus, blood, head/neck, ovary, liver, cervix, thyroid, bladder, and stomach. In some embodiments this predetermined set of organs is healthy. In alternative embodiments, this predetermined set of organs is afflicted with cancer that originated in one of the organs in the predetermined set of organs. In still further alternative embodiments, the predetermined set of organs is afflicted with cancer that originated in an organ other than the predetermined set of organs and metastasized to the predetermined set of organs.

In some embodiments, a cell source of any embodiment of the present disclosure is any combination of cell types provided that such cell types originated from a predetermined set of organs. In some such embodiments, this predetermined set of organs is any four organs, five organs, six organs, or seven organs in the set breast, lung, prostate, colon/rectum, kidney, uterus, pancreas, esophagus, blood, head/neck, ovary, liver, cervix, thyroid, bladder, and stomach. In some embodiments this predetermined set of organs is healthy. In alternative embodiments, this predetermined set of organs is afflicted with cancer that originated in one of the organs in the predetermined set of organs. In still further alternative embodiments, the predetermined set of organs is afflicted with cancer that originated in an organ other than the predetermined set of organs and metastasized to the predetermined set of organs.

In some specific embodiments, a cell source of any embodiment of the present disclosure is white blood cells. In some such embodiments, the cell source is neutrophils, eosinophils, basophils, lymphocytes, B lymphocytes, T lymphocytes, cytotoxic T cells, monocytes, or any combination thereof.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation (s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures, and techniques have not been shown in detail.

The foregoing description, for purpose of explanation, has been described with reference to specific implementations.

However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A computer-implemented method of identifying a plurality of qualifying methylation patterns that discriminate or indicate a cancer condition, the method comprising:

A) obtaining, at a computer system, a first dataset, in electronic form, wherein the first dataset comprises a corresponding fragment methylation pattern of each respective fragment in a first plurality of fragments, wherein the corresponding fragment methylation pattern of each respective fragment (i) is determined by a methylation sequencing of nucleic acids from a respective biological sample obtained from a corresponding subject in a first set of subjects and (ii) comprises a methylation state of each CpG site in a corresponding plurality of CpG sites in the respective fragment, and wherein the first plurality of fragments comprises more than 1000 fragments;

B) obtaining, at the computer system, a second dataset, in electronic form, wherein the second dataset comprises a corresponding fragment methylation pattern of each respective fragment in a second plurality of fragments, wherein the corresponding fragment methylation pattern of each respective fragment (i) is determined by a methylation sequencing of nucleic acids from a respective biological sample obtained from a corresponding subject in a second set of subjects and (ii) comprises a methylation state of each CpG site in a corresponding plurality of CpG sites in the respective fragment, wherein each subject in the first set of subjects has a first state of the cancer condition and each subject in the second set of subjects has a second state of the cancer condition, and wherein the second plurality of fragments comprises more than 1000 fragments;

C) generating, using one or more processors associated with the computer system, one or more first state interval maps for one or more corresponding genomic regions using the first dataset, wherein:

each first state interval map in the one or more first state interval maps comprises a corresponding independent plurality of nodes, wherein the corresponding independent plurality of nodes comprises more than 50 nodes, each first state interval map is represented as a hierarchical tree structure, wherein each node in the hierarchical tree structure corresponds to a genomic region, nodes at shallower depths represent larger genomic regions, nodes at deeper depths represent smaller genomic regions, and the hierarchical tree structure is constructed recursively by partitioning the genomic regions into sub-regions, and each respective node in each corresponding independent plurality of nodes in the one or more first state interval maps is characterized by (1) corresponding start methylation site, (2) corresponding end methylation site and, (3) each different fragment methylation pattern observed across the first plurality of fragments in the first dataset between the corresponding start methylation site and the corresponding end methylation site of the respective node, (i) a representation of the different fragment methylation pattern and (ii) a count of fragments in the first dataset whose fragment methylation pattern begins at the corresponding start methylation site and ends at the corresponding end methylation site and has the different fragment methylation pattern;

D) generating, using the one or more processors, one or more second state interval maps for one or more corresponding genomic regions using the second dataset, wherein:

each second state interval map in the one or more second state interval maps comprises a corresponding independent plurality of nodes, wherein the corresponding independent plurality of nodes comprises more than 50 nodes, and each respective node in each corresponding independent plurality of nodes in the one or more second state interval maps is characterized by a corresponding start methylation site, a corresponding end methylation site and, for each different fragment methylation pattern observed across the second plurality of fragments in the second dataset between the corresponding start methylation site and the corresponding end methylation site of the respective node, (i) a representation of the different fragment methylation pattern and (ii) a count of fragments in the second dataset whose fragment methylation pattern begins at the corresponding start methylation site and ends at the corresponding end methylation site and has the different fragment methylation pattern;

E) filtering, using the one or more processors, the one or more first state interval maps and the one or more second state interval maps to remove one or more nodes or corresponding genomic sub-regions that satisfy one or more exclusion criteria, wherein the one or more exclusion criteria comprises:

i) belonging to a blacklisted region of a genome;

ii) having a noise level greater than a threshold across non-cancer control samples; or iii) having a low discriminatory power between cancer and non-cancer states;

F) constructing, using the one or more processors, a filtered data structure comprising the remaining first nodes and second nodes, and fragment methylation pattern representations associated with the remaining first nodes and second nodes, from the filtered one or more first state interval maps and the filtered one or more second state interval maps;

G) scanning, using the one or more processors, the filtered data structure for a plurality of qualifying methylation patterns, wherein each qualifying methylation pattern in the plurality of qualifying methylation patterns:

(i) has a length that is in a predetermined CpG site number range, within the fragment methylation patterns of the one or more first state interval maps and the one or more second state interval maps, (ii) satisfies one or more selection criteria, and (iii) spans a corresponding CpG interval between a corresponding initial CpG site and a corresponding final CpG site, thereby identifying the plurality of qualifying methylation patterns that discriminates or indicates a cancer condition, H) training, using the one or more processors, a classifier for classifying a state of the cancer condition using the plurality of qualifying methylation patterns and the associated filtered data structure, wherein the training comprises constructing a primary training dataset that comprises the plurality of qualifying methylation patterns as canonical sets of methylation state vectors, in conjunction with cell source labels corresponding to the first set of subjects and the second set of subjects, and wherein the classifier comprises a neural network;

I) applying, using the one or more processors, the trained classifier to a third dataset comprising fragment methylation patterns obtained from a biological sample from a test subject; and J) receiving, at the computer system, output from the trained classifier indicating a state of the cancer condition in the test subject.

2. The method of claim 1, wherein the one or more selection criteria specifies that a methylation pattern:

(i) is represented in the one or more first state interval maps with a first frequency that satisfies a first frequency threshold, (ii) is represented in the one or more first state interval maps with a coverage that satisfies a first state depth threshold, and (iii) is represented in the one or more second state interval maps with a second frequency that satisfies a second frequency threshold.

3. The method of claim 2, wherein:

(i) the methylation pattern is represented in the one or more first state interval maps with a first frequency that satisfies a first frequency threshold when the frequency of the methylation pattern in the one or more first state interval maps exceeds the first frequency threshold, (ii) the methylation pattern is represented in the one or more first state interval maps with a coverage that satisfies the first state depth threshold when the coverage of the methylation pattern in the one or more first state interval maps exceeds the first state depth threshold, and (iii) the methylation pattern is represented in the one or more second state interval maps with a second frequency that satisfies the second frequency threshold when the frequency of the methylation pattern in the one or more second state interval maps is less than the second frequency threshold.

4. The method of claim 1, wherein the first and second plurality of fragments are cell-free nucleic acids.

5. The method of claim 1, wherein:

the one or more first state interval maps are a plurality of first state interval maps;

the one or more second state interval maps are a plurality of second state interval maps; the one or more corresponding genomic regions are a plurality of genomic regions; and each respective genomic region in the plurality of genomic regions is represented by a first state interval map in the plurality of first state interval maps and a second state interval map in the plurality of second state interval maps and wherein the plurality of genomic regions is between 10 and 30, or each genomic region in the plurality of genomic regions is a different human chromosome, or the plurality of genomic regions consists of between two and 1000 genomic regions, between 500 and 5,000 genomic regions, between 1,000 and 20,000 genomic regions or between 5,000 and 50,000 genomic regions.

6. The method of claim 5, wherein the methylation sequencing of the A) obtaining and B) obtaining is targeted sequencing using a plurality of probes and each genomic region in the plurality of genomic regions is associated with at least one probe in the plurality of probes.

7. The method of claim 1, wherein the predetermined CpG number range is between 2 and 100 contiguous CpG sites in a human reference genome.

8. The method of claim 1, wherein there are more than 10,000 CpG sites, more than 25,000 CpG sites, more than 50,000 CpG sites, or more than 80,000 CpG sites across the one or more corresponding genomic regions.

9. The method of claim 1, wherein an average sequence read length of a corresponding plurality of sequence reads obtained by the methylation sequencing for a respective fragment is between 140 and 280 nucleotides.

10. The method of claim 1, wherein each genomic region in the one or more corresponding genomic regions represents between 500 base pairs and 10,000 base pairs of a human genome reference sequence.

11. The method of claim 1, wherein the methylation sequencing is i) whole-genome methylation sequencing or ii) targeted DNA methylation sequencing using a plurality of nucleic acid probes.

12. A computer system for identifying a plurality of qualifying methylation patterns that discriminate or indicate a cancer condition, the computer system comprising:

at least one processor; and a memory storing at least one program for execution by the at least one processor, the at least one program comprising instructions for:

A) obtaining a first dataset, in electronic form, wherein the first dataset comprises a corresponding fragment methylation pattern of each respective fragment in a first plurality of fragments, wherein the corresponding fragment methylation pattern of each respective fragment (i) is determined by a methylation sequencing of nucleic acids from a respective biological sample obtained from a corresponding subject in a first set of subjects and (ii) comprises a methylation state of each CpG site in a corresponding plurality of CpG sites in the respective fragment, and wherein the first plurality of fragments comprises more than 1000 fragments;

B) obtaining a second dataset, in electronic form, wherein the second dataset comprises a corresponding fragment methylation pattern of each respective fragment in a second plurality of fragments, wherein the corresponding fragment methylation pattern of each respective fragment (i) is determined by a methylation sequencing of nucleic acids from a respective biological sample obtained from a corresponding subject in a second set of subjects and (ii) comprises a methylation state of each CpG site in a corresponding plurality of CpG sites in the respective fragment, wherein each subject in the first set of subjects has a first state of the cancer condition and each subject in the second set of subjects has a second state of the cancer condition, and wherein the second plurality of fragments comprises more than 1000 fragments;

C) generating one or more first state interval maps for one or more corresponding genomic regions using the first dataset, wherein:

each first state interval map in the one or more first state interval maps comprises a corresponding independent plurality of nodes, wherein the corresponding independent plurality of nodes comprises more than 50 nodes, each first state interval map is represented as a hierarchical tree structure, wherein each node in the hierarchical tree structure corresponds to a genomic region, nodes at shallower depths represent larger genomic regions, nodes at deeper depths represent smaller genomic regions, and the hierarchical tree structure is constructed recursively by partitioning the genomic regions into sub-regions, and each respective node in each corresponding independent plurality of nodes in the one or more first state interval maps is characterized by a corresponding start methylation site, a corresponding end methylation site and, for each different fragment methylation pattern observed across the first plurality of fragments in the first dataset between the corresponding start methylation site and the corresponding end methylation site of the respective node, (i) a representation of the different fragment methylation pattern and (ii) a count of fragments in the first dataset whose fragment methylation pattern begins at the corresponding start methylation site and ends at the corresponding end methylation site and has the different fragment methylation pattern;

D) generating one or more second state interval maps for one or more corresponding genomic regions using the second dataset, wherein:

each second state interval map in the one or more second state interval maps comprises a corresponding independent plurality of nodes, wherein the corresponding independent plurality of nodes comprises more than 50 nodes, and each respective node in each corresponding independent plurality of nodes in the one or more second state interval maps is characterized by a corresponding start methylation site, a corresponding end methylation site and, for each different fragment methylation pattern observed across the second plurality of fragments in the second dataset between the corresponding start methylation site and the corresponding end methylation site of the respective node, (i) a representation of the different fragment methylation pattern and (ii) a count of fragments in the second dataset whose fragment methylation pattern begins at the corresponding start methylation site and ends at the corresponding end methylation site and has the different fragment methylation pattern;

E) filtering the one more first state interval maps and the one or more second state interval maps to remove one or more nodes or corresponding genomic sub-regions that satisfy one or more exclusion criteria, wherein the one or more exclusion criteria comprises:

i) belonging to a blacklisted region of a genome;

ii) having a noise level greater than a threshold across non-cancer control samples; or iii) having a low discriminatory power between cancer and non-cancer states:

F) constructing a filtered data structure comprising the remaining first nodes and second nodes, and fragment methylation pattern representations associated with the remaining first nodes and second nodes, from the filtered one or more first state interval maps and the filtered one or more second state interval maps;

G) scanning the filtered data structure for a plurality of qualifying methylation patterns, wherein each qualifying methylation pattern in the plurality of qualifying methylation patterns:

(i) has a length that is in a predetermined CpG site number range, within the fragment methylation patterns of the one or more first state interval maps and the one or more second state interval maps, (ii) satisfies one or more selection criteria, and (iii) spans a corresponding CpG interval between a corresponding initial CpG site and a corresponding final CpG site, thereby identifying the plurality of qualifying methylation patterns that discriminates or indicates a cancer condition, H) training a classifier for classifying a state of the cancer condition using the plurality of qualifying methylation patterns and the associated filtered data structure, wherein the training comprises constructing a primary training dataset that comprises the plurality of qualifying methylation patterns as canonical sets of methylation state vectors, in conjunction with cell source labels corresponding to the first set of subjects and the second set of subjects, and wherein the classifier comprises a neural network;

I) applying the trained classifier to a third dataset comprising fragment methylation patterns obtained from a biological sample from a test subject; and J) receiving output from the trained classifier indicating a state of the cancer condition in the test subject.

13. A non-transitory computer-readable storage medium having stored thereon program code instructions that, when executed by a processor associated with a computer system, cause the processor to perform a method for identifying a plurality of qualifying methylation patterns that discriminate or indicate a cancer condition, the method comprising:

A) obtaining, at the computer system, a first dataset, in electronic form, wherein the first dataset comprises a corresponding fragment methylation pattern of each respective fragment in a first plurality of fragments, wherein the corresponding fragment methylation pattern of each respective fragment (i) is determined by a methylation sequencing of nucleic acids from a respective biological sample obtained from a corresponding subject in a first set of subjects and (ii) comprises a methylation state of each CpG site in a corresponding plurality of CpG sites in the respective fragment, and wherein the first plurality of fragments comprises more than 1000 fragments;

B) obtaining, at the computer system, a second dataset, in electronic form, wherein the second dataset comprises a corresponding fragment methylation pattern of each respective fragment in a second plurality of fragments, wherein the corresponding fragment methylation pattern of each respective fragment (i) is determined by a methylation sequencing of nucleic acids from a respective biological sample obtained from a corresponding subject in a second set of subjects and (ii) comprises a methylation state of each CpG site in a corresponding plurality of CpG sites in the respective fragment, wherein each subject in the first set of subjects has a first state of the cancer condition and each subject in the second set of subjects has a second state of the cancer condition, and wherein the second plurality of fragments comprises more than 1000 fragments;

C) generating, using the processor, one or more first state interval maps for one or more corresponding genomic regions using the first dataset, wherein:

each first state interval map in the one or more first state interval maps comprises a corresponding independent plurality of nodes, wherein the corresponding independent plurality of nodes comprises more than 50 nodes, each first state interval map is represented as a hierarchical tree structure, wherein each node in the hierarchical tree structure corresponds to a genomic region, nodes at shallower depths represent larger genomic regions, nodes at deeper depths represent smaller genomic regions, and the hierarchical tree structure is constructed recursively by partitioning the genomic regions into sub-regions, and each respective node in each corresponding independent plurality of nodes in the one or more first state interval maps is characterized by (1) a corresponding start methylation site, (2) a corresponding end methylation site and, (3) for each different fragment methylation pattern observed across the first plurality of fragments in the first dataset between the corresponding start methylation site and the corresponding end methylation site of the respective node, (i) a representation of the different fragment methylation pattern and (ii) a count of fragments in the first dataset whose fragment methylation pattern begins at the corresponding start methylation site and ends at the corresponding end methylation site and has the different fragment methylation pattern;

D) generating one or more second state interval maps for one or more corresponding genomic regions using the second dataset, wherein:

each second state interval map in the one or more second state interval maps comprises a corresponding independent plurality of nodes, wherein the corresponding independent plurality of nodes comprises more than 50 nodes, and each respective node in each corresponding independent plurality of nodes in the one or more second state interval maps is characterized by (1) a corresponding start methylation site, (2) a corresponding end methylation site and, (3) for each different fragment methylation pattern observed across the second plurality of fragments in the second dataset between the corresponding start methylation site and the corresponding end methylation site of the respective node, (i) a representation of the different fragment methylation pattern and (ii) a count of fragments in the second dataset whose fragment methylation pattern begins at the corresponding start methylation site and ends at the corresponding end methylation site and has the different fragment methylation pattern;

E) filtering, using the processor, the one more first state interval maps and the one or more second state interval maps to remove one or more nodes or corresponding genomic sub-regions that satisfy one or more exclusion criteria, wherein the one or more exclusion criteria comprises:

i) belonging to a blacklisted region of a genome;

ii) having a noise level greater than a threshold across non-cancer control samples; or iii) having a low discriminatory power between cancer and non-cancer states;

E) constructing, using the processor, a filtered data structure comprising the remaining first nodes and second nodes, and fragment methylation pattern representations associated with the remaining first nodes and second nodes, from the filtered one or more first state interval maps and the filtered one or more second state interval maps:

G) scanning the hierarchical tree structures of the one or more first state interval maps and the one or more second state interval maps for a plurality of qualifying methylation patterns, wherein each qualifying methylation pattern in the plurality of qualifying methylation patterns:

(i) has a length that is in a predetermined CpG site number range, within the fragment methylation patterns of the one or more first state interval maps and the one or more second state interval maps, (ii) satisfies one or more selection criteria, and (iii) spans a corresponding CpG interval between a corresponding initial CpG site and a corresponding final CpG site, thereby identifying the plurality of qualifying methylation patterns that discriminates or indicates a cancer condition, and training a classifier for classifying a state of the cancer condition using the plurality of qualifying methylation patterns, wherein the training comprises constructing a primary training dataset that comprises the plurality of qualifying methylation patterns as canonical sets of methylation state vectors, in conjunction with cell source labels corresponding to the first set of subjects and the second set of subjects, and the classifier comprises a neural network, a logistic regression model, a support vector machine, a Naive Bayes model, a boosted trees model, a random forest model, a decision tree model, a multinomial logistic regression model, a linear model, or a linear regression model.

14. The method of claim 1, wherein the scanning the hierarchical tree structures of the one or more first state interval maps and the one or more second state interval maps for the plurality of qualifying methylation patterns comprises:

generating a query for a qualifying methylation pattern using hierarchical query propagation;

propagating the query down the hierarchical tree structure, with each node processing a corresponding genomic region independently; and aggregating results of the qualifying patterns identified from child nodes at corresponding parent nodes as the query response propagates back up the hierarchical tree structure, wherein the hierarchical query propagation reduces computational overhead by allowing intermediate nodes to aggregate results and discard irrelevant data from corresponding child nodes.

15. The method of claim 1, wherein the training of the classifier further comprises:

incorporating coefficients derived from one or more auxiliary training datasets to supplement the primary training dataset using transfer learning, wherein the coefficients are applied via matrix multiplication to obtain an intermediate classifier that is further trained using the primary training dataset.

* * * * *